(12) United States Patent
Selnick et al.

(10) Patent No.: US 9,611,275 B2
(45) Date of Patent: Apr. 4, 2017

(54) PERMEABLE GLYCOSIDASE INHIBITORS AND USES THEREOF

(71) Applicant: Merck Sharp & Dohme Corp., Rahway, NJ (US)

(72) Inventors: Harold G. Selnick, Harleyville, PA (US); Wenping Li, Lansdale, PA (US); Eric Hostetler, Collegeville, PA (US); Kun Liu, Needham, MA (US); Ernest J. McEachern, British Columbia (CA); Yuanxi Zhou, British Columbia (CA); Zhongyong Wei, Beijing (CN); Changwei Mu, Beijing (CN); Yaode Wang, Beijing (CN); Jiang Chang, Beijing (CN)

(73) Assignees: ALECTOS THERAPEUTICS, INC., Burnaby, British Columbia (CA); MERCK SHARP & DOHME CORP., Rahway, NJ (US)

(*) Notice: Subject to any disclaimer, the term of this patent is extended or adjusted under 35 U.S.C. 154(b) by 87 days.

(21) Appl. No.: 14/399,146

(22) PCT Filed: May 3, 2013

(86) PCT No.: PCT/US2013/039377
§ 371 (c)(1),
(2) Date: Nov. 5, 2014

(87) PCT Pub. No.: WO2013/169576
PCT Pub. Date: Nov. 14, 2013

(65) Prior Publication Data
US 2015/0152127 A1    Jun. 4, 2015

Related U.S. Application Data

(60) Provisional application No. 61/655,641, filed on Jun. 5, 2012.

(30) Foreign Application Priority Data

May 8, 2012  (CN) ................ PCT/CN2012/075185

(51) Int. Cl.
*C07D 513/04* (2006.01)
*C07B 59/00* (2006.01)
*C07H 9/06* (2006.01)

(52) U.S. Cl.
CPC .......... *C07D 513/04* (2013.01); *C07B 59/005* (2013.01); *C07B 2200/05* (2013.01); *C07H 9/06* (2013.01)

(58) Field of Classification Search
CPC .................................................... C07D 513/04
See application file for complete search history.

(56) References Cited

FOREIGN PATENT DOCUMENTS

| CA | WO 2012061972 A1 * | 5/2012 | ........... C07D 513/04 |
|---|---|---|---|
| WO | WO2008025170 A1 | 3/2008 | |
| WO | WO2011140640 A1 | 11/2011 | |
| WO | WO2012062157 | 5/2012 | |
| WO | WO2012064680 A1 | 5/2012 | |
| WO | WO2012159262 | 11/2012 | |
| WO | WO2013025452 | 2/2013 | |

OTHER PUBLICATIONS

Extended European Search Report for EP13787989.6 (PCT/US2013/039377), October 12, 2015.
Yuzwa, et al., A potent mechanism-inspired O-GlcNAcase inhibitor that blocks phosphorylation of tau in vivo, Nature Chemical Biology, 483-490, vol. 4, No. 8, Aug. 2008.

* cited by examiner

*Primary Examiner* — Matthew Coughlin
(74) *Attorney, Agent, or Firm* — J. Eric Thies; John C. Todaro

(57) ABSTRACT

The present invention is directed to compounds and pharmaceutical formulations comprising these compounds which are useful as O-linked N-acetylglucosaminidase (O-GlcNAcase) inhibitors, and thus may be useful for the treatment of certain disorders such as Alzheimer's disease including reducing NFTs and/or hyperphosphorylated tau. The invention is also directed to use of the compounds as O-GlcNAcase imaging agents.

30 Claims, No Drawings

PERMEABLE GLYCOSIDASE INHIBITORS AND USES THEREOF

BACKGROUND OF THE INVENTION

It is well established that Alzheimer's disease and a number of related tauopathies including Downs' syndrome, Pick's disease, Niemann-Pick Type C disease, and Amyotrophic lateral sclerosis are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In Alzheimer's disease patients, however, tau becomes hyperphosphorylated, disrupting its normal functions, forming PHFs and ultimately aggregating to form NFTs. Six isoforms of tau are found in the human brain. In Alzheimer's disease patients, all six isoforms of tau are found in NFTs, and all are markedly hyperphosphorylated (Goedert et al., *Neuron* 1992, 8, 159; and Goedert et al., *Neuron* 1989, 3, 519).

Tau in healthy brain tissue bears only 2 or 3 phosphate groups, whereas those found in the brains of Alzheimer's disease subjects bear, on average, 8 phosphate groups (Kopke et al., *J Biol Chem* 1993, 268, 24374; and Ksiezak-Reding et al., *Brain Res* 1992, 597, 209). A clear parallel between NFT levels in the brains of Alzheimer's disease patients and the severity of dementia strongly supports a key role for tau dysfunction in Alzheimer's disease (Arriagada et al., *Neurology* 1992, 42, 631; Riley et al., *Ann Neurol* 2002, 51, 567; and Alafuzoff et al., *Acta Neuropathol (Berl)* 1987, 74, 209). Accordingly, approaches aimed at reducing NFTs and/or hyperphosphorylated tau represent potential disease modifying treatments for Alzheimer's disease.

It is also well-established that a wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage (Torres et al., *J Biol Chem* 1984, 259, 3308). This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT) (Haltiwanger et al., *J Biol Chem* 1990, 265, 2563; Kreppel et al., *J Biol Chem* 1997, 272, 9308; Lubas et al., *J Biol Chem* 1997, 272, 9316; and Lubas et al., *J Biol Chem* 2000, 275, 10983). A second enzyme, known as O-linked N-acetylglucosamin-dase (O-GlcNAcase) (Dong et al., *J Biol Chem* 1994, 269, 19321; and Gao et al., *J Biol Chem* 2001, 276, 9838) removes this post-translational modification to liberate proteins making the O-GlcNAc-modification a dynamic cycle occurring several times during the lifetime of a protein (Roquemore et al., *Biochemistry* 1996, 35, 3578).

It has recently emerged that phosphate levels of tau are regulated, in part, by the levels of O-Glc-NAc on tau. The presence of O-GlcNAc on tau has stimulated studies that correlate O-GlcNAc levels with tau phosphorylation levels. In this regard, it has been found that increases in phosphorylation levels result in decreased O-GlcNAc levels and conversely, increased O-GlcNAc levels correlate with decreased phosphorylation levels (Griffith et al., *Eur J Biochem* 1999, 262, 824). Hyperphosphorylated tau in human Alzheimer's disease brains has markedly lower levels of O-GlcNAc than are found in healthy human brains (Liu et al., *Proc Natl Acad Sci USA* 2004, 101, 10804).

Very recently, it has been shown that O-GlcNAc levels of soluble tau protein from human brains affected with Alzheimer's disease are markedly lower than those from healthy brain (Liu et al., *Brain*, 2009, 132, 1820).

Recent studies (Yuzwa et al., *Nat Chem Biol* 2008, 4, 483) support the therapeutic potential of small-molecule O-GlcNAcase inhibitors to limit tau hyperphosphorylation for treatment of Alzheimer's disease and related tauopathies. Specifically, the O-GlcNAcase inhibitor thiamet-G has been implicated in the reduction of tau phosphorylation in cultured PC-12 cells at pathologically relevant sites and in the brains of animals after in vivo administration of this inhibitor (Yuzwa et al., supra). Accordingly, O-GlcNAcase inhibitors are widely recognized as a valid therapeutic approach to reduce hyperphosphorylation of tau and formation of NFTs.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion (Bounelis et al., *Shock* 2004, 21 170 Suppl. 2, 58; Fulop et al., *Circulation Research* 2005, 97, E28; Liu et al., *Faseb Journal* 2006, 20, A317; Marchase et al., PCT Int. App. WO 2006016904 2006; Fulop et al., *Journal of Molecular and Cellular Cardiology* 2004, 37, 286; Fulop et al., *Faseb Journal* 2005, 19, A689; and Liu et al., *Journal of Molecular and Cellular Cardiology* 2007, 42, 177), trauma hemorrhage (Not et al., *Faseb Journal* 2006, 20, A1471; Yang et al., *Shock* 2006, 25, 600; and Zou et al., *Faseb Journal* 2005, 19, A1224), hypervolemic shock (Marchase et al., *Circulation* 2004, 110, 1099) and calcium paradox (Bounelis et al., supra; and Liu et al., *Journal of Molecular and Cellular Cardiology* 2006, 40, 303). Moreover, strong evidence indicates that these cardioprotective effects are mediated by elevated levels of protein O-GlcNAc modification (Bounelis et al., supra; Fulop et al., *Circulation Research* 2005, 97, E28; Marchase et al., 2006, supra; Liu et al., 2007, supra; Yang et al., supra; Liu et al., *Journal of Molecular and Cellular Cardiology* 2006, 40, 303; Liu et al., *Faseb Journal* 2005, 19, A691; Nagy et al., *American Journal of Physiology-Cell Physiology* 2006, 290, C57; and Fulop et al., *Cardiovascular Research* 2007, 73, 288). There is also evidence that the O-GlcNAc modification plays a role in a variety of neurodegenerative diseases, including Parkinson's disease and Huntington's disease (Lefebvre et al., *Expert Review of Proteomics* 2005, 2, 265).

Humans have three genes encoding enzymes that cleave terminal β-N-acetylglucosamine residues from glycoconjugates. The first of these encodes the enzyme O-glycoprotein 2-acetamido-2-deoxy-β-D-glucopyranosidase (O-GlcNAcase) as is indicated above. O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/ (Henrissat et al., *Biochem J* 1996, 316 (PT2), 695; and Henrissat et al., 1993, supra). O-GlcNAcase acts to hydrolyse O-GlcNAc off of serine and threonine residues of post-translationally modified proteins (Torres et al., supra; Dong et al., supra; Gao et al., supra; Wells et al., *Science* 2001, 291, 2376; and Hanover, *Faseb Journal* 2001, 15, 1865). Consistent with the presence of O-GlcNAc on many intracellular proteins, the enzyme O-GlcNAcase appears to have a role in the etiology of several diseases including type II diabetes (Volleller et al., *Proc Natl Acad Sci USA* 2002, 99, 5313; and McClain et al., *Proc Natl Acad Sci USA* 2002, 99, 10695), A D (Griffith, *Biochem Biophys Res Commun* 1995, 213, 424; Liu et al., *Proc Natl Acad Sci USA* 2004, 101, 10804; and Yao et al., *J. Neurosci* 1998, 18, 2399) and cancer (Chou et al., *Adv Exp Med Biol* 2001, 491, 413; and Yang et al., *Nature Cell Biology* 2006, 8, 1054). Although O-GlcNAcase was likely isolated earlier on (Braidman et al., *Biochem J* 1974, 143, 295; and Ueno et al., *Biochim Biophys Acta* 1991, 1074, 79), about 20 years elapsed before its biochemical role in acting to cleave O-GlcNAc from serine and threonine residues of proteins was understood (Dong et al., supra). More recently O-GlcNAcase has been cloned (Gao et al., supra), partially characterized (Toleman et al., *J Biol Chem* 2004) and suggested to have additional activity as a histone acetyltransferase (Toleman et al., supra). However, little was known about the catalytic mechanism of this enzyme.

The other two genes, HEXA and HEXB, encode enzymes catalyzing the hydrolytic cleavage of terminal β-N-acetyl-glucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B (Triggs-Raine et al., *Adv Genet*, 2001, 44, 199). These enzymatic deficiencies cause an accumulation of glycolipids and glycoconjugates in the lysosomes resulting in neurological impairment and deformation. The deleterious effects of accumulation of gangliosides at the organismal level are still being uncovered (Zhou et al., *Science* 2004).

As a result of the biological importance of these β-N-acetyl-glucosaminidases, small molecule inhibitors of glycosidases (Legler et al., *Biochim Biophys Acta* 1992, 1080, 89; Horsch et al., *Eur J. Biochem* 1991, 197, 815; Liu et al., *Chem Biol* 2001, 8, 701; and Knapp et al., *J Am Chem Soc* 1996, 118, 6804) have received a great deal of attention (Lillelund et al., *Chem Rev* 2002, 102, 515), both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenyl-carbamate (PUGNAc) (Vosseller et al., supra; Konrad et al., *Biochem J* 2001, 356, 31; Liu et al., *J Neurochem* 2004, 89, 1044; Parker et al., *J Biol Chem* 2004, 279, 20636; and Arias et al., *Diabetes* 2004, 53, 921).

STZ has long been used as a diabetogenic compound because it has a particularly detrimental effect on β-islet cells (Junod et al., *Proc Soc Exp Biol Med* 1967, 126, 201). STZ exerts its cytotoxic effects through both the alkylation of cellular DNA (Junod et al., supra; and Bennett et al., *Cancer Res* 1981, 41, 2786) as well as the generation of radical species including nitric oxide (Kroncke et al., *Biol Chem Hoppe Seyler* 1995, 376, 179). The resulting DNA strand breakage promotes the activation of poly(ADP-ribose) polymerase (PARP) (Yamamoto et al., *Nature* 1981, 294, 284) with the net effect of depleting cellular NAD+ levels and, ultimately, leading to cell death (Yamada et al., *Diabetes* 1982, 31, 749; and Burkart et al., *Nat Med* 1999, 5, 314). Other investigators have proposed instead that STZ toxicity is a consequence of the irreversible inhibition of O-GlcNAcase, which is highly expressed within β-islet cells (Konrad et al., supra; and Roos, *Proc Assoc Am Physicians* 1998, 110, 422). This hypothesis has, however, been brought into question by two independent research groups (Gao et al., *Arch Biochem Biophys* 2000, 383, 296; and Okuyama et al., *Biochem Biophys Res Commun* 2001, 287, 366). Because cellular O-GlcNAc levels on proteins increase in response to many forms of cellular stress (Zachara et al., *J Biol Chem* 2004, 279, 30133) it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase (Hanover et al., *Arch Biochem Biophys* 1999, 362, 38) and although it has been proposed by others that STZ acts to irreversibly inhibit O-GlcNAcase (Liu et al., *Mol Cell Endocrinol* 2002, 194, 135), there has been no clear demonstration of this mode of action. Recently, it has been shown that STZ does not irreversibly inhibit O-GlcNAcase (Macauley et al., *J Biol Chem* 2005, 280, 25313).

NAG-thiazoline has been found to be a potent inhibitor of family 20 hexosaminidases (Knapp et al., supra; and Mark et al., *J Biol Chem* 2001, 276, 10330), and more recently, the family 84 O-GlcNAcases (Macauley et al., supra). Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase (Dong et al., supra; and Haltiwanger et al., *J Biol Chem* 1998, 273, 3611) and the family 20 human β-hexosaminidases (Miller et al., *Development* 1993, 118, 1279). This molecule, developed by Vasella and coworkers, was found to be a potent competitive inhibitor of the β-N-acetyl-glucosaminidases from *Canavalia ensiformis*, *Mucor rouxii*, and the β-hexosaminidase from bovine kidney (Horsch et al., supra). It has been demonstrated that administration of PUGNAc in a rat model of trauma hemorrhage decreases circulating levels of the pro-inflammatory cytokines TNF α and IL-6 (Zou et al., *Shock* 2007, 27, 402). It has also been shown that administration of PUGNAc in a cell-based model of lymphocyte activation decreases production of the cytokine IL-2 (Huang et al., *Cellular Immunology* 2007, 245, 1). Recent studies have indicated that PUGNAc can be used in an animal model to reduce myocardial infarct size after left coronary artery occlusion (U.J.G. Conference, in *US/Japan Gylco 2004 Conference*, Honolulu, Hi., 2004). Of particular significance is the fact that elevation of O-GlcNAc levels by administration of PUGNAc, an inhibitor of O-GlcNAcase, in a rat model of trauma hemorrhage improves cardiac function (Zou et al., *Shock* 2007, 27, 402; and Zou et al., *Faseb Journal* 2006, 20, A1471). In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells (Champattanachai et al., *American Journal of Physiology-Cell Physiology* 2007, 292, C178).

More recently, it has been suggested that the selective O-GlcNAcase inhibitor NButGT exhibits protective activity in cell-based models of ischemia/reperfusion and cellular stresses, including oxidative stress (Champattanachai et al., *American Journal of Physiology-Cell Physiology* 2008, 294, C1509). This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar., 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; and PCT/CA2009/001302, filed 16 Sep. 2009, published under WO 2010/037207 on 8 Apr. 2010, describe selective inhibitors of O-GlcNAcase.

Noninvasive nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, brain regional distribution and function.

For noninvasive in vivo imaging, compounds can be labeled with either positron- or gamma-emitting radionuclides. The most commonly used positron emitting (PET) radionuclides are $^{11}C$, $^{18}F$, $^{15}N$ and $^{13}N$, all of which are accelerator produced, and have half-lives of 20, 110, 2 and 10 minutes, respectively. These short half-lives endow a number of advantages to their use as tracers to probe biological processes in vivo using PET. Since the half-lives of these radionuclides are so short, it is only feasible to use them at institutions that have an accelerator on site or very close by for their production, thus limiting their use.

In a typical PET study, a small amount of radiotracer is administered to the experimental animal, normal human or patient being tested. The radiotracer then circulates in the blood of the subject and may be absorbed in certain tissues. The radiotracer may be preferentially retained in some of these tissues because of specific enzymatic conversion or by specific binding to macromolecular structures such as proteins. Using sophisticated imaging instrumentation to detect positron emission, the amount of radiotracer is then non-invasively assessed in the various tissues in the body. The resulting data are analyzed to provide quantitative spatial information of the in vivo biological process for which the tracer was designed. PET gives pharmaceutical research investigators the capability to assess biochemical changes or metabolic effects of a drug candidate in vivo for extended periods of time, and PET can be used to measure drug distribution, thus allowing the evaluation of the pharmacokinetics and pharmacodynamics of a particular drug candidate under study. Importantly, PET tracers can be designed and used to quantitate the presence of binding sites in tissues. Consequently, interest in PET tracers for drug development has been expanding based on the development of isotopically labeled biochemicals and appropriate detection devices to detect the radioactivity by external imaging.

Noninvasive nuclear imaging techniques such as PET have been particularly important in providing the ability to study neurological diseases and disorders, including stroke, Parkinson's disease, epilepsy, cerebral tumors and Alzheimer's disease Alzheimer's disease is the most common form of dementia. A PET radiotracer specific O-GlcNAcase would provide a powerful tool in demonstrating target engagement and pharmacodynamic activity and determining optimal doses in preclinical evaluation and clinical trials.

Disclosed herein are compounds that selectively inhibit the activity of O-GlcNAcase over the functionally related beta-hexosaminidases A and B, compositions that include the compounds, and methods of their use. Compounds disclosed herein as inhibitors of O-GlcNAcase possess both high potency and high permeability, and thus are useful in the treatment of diseases, disorders, or conditions that would benefit from the inhibition of O-GlcNAcase and reducing NFTs. The invention, also provides compounds which when radiolabeled are useful as PET radiotracers for imaging of O-GlcNAcase in vivo.

SUMMARY OF THE INVENTION

The invention is directed to compounds which are useful as inhibitors of O-GlcNAcase and methods for the use of such O-GlcNAcase inhibitors and pharmaceutical formulations comprising these inhibitors for treatment of certain disorders, including Alzheimer's disease. The invention is also concerned with such radiolabeled O-GlcNAcase inhibitors for use in binding studies and diagnostic imaging of O-GlcNAcase in mammals.

DETAILED DESCRIPTION OF THE INVENTION

As used above, and throughout this disclosure, the following terms, unless otherwise indicated, shall be understood to have the following meanings:

"One or more" means at least one.

"Subject" means an animal, such as a mammal, e.g., mouse, rat, horse, cow, sheep, goat, dog, cat, pig, monkey, or a human; or avian species, e.g., chicken.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkoxy" means an —O—(C1-10)alkyl or alkenyl group in which the alkyl or alkenyl group is as previously described. Non-limiting examples of suitable alkoxy groups include methoxy, ethoxy, n-propoxy, isopropoxy and n-butoxy. The bond to the parent moiety is through the ether oxygen.

"Cycloalkyl" refers to a stable monovalent monocyclic hydrocarbon group consisting solely of carbon and hydrogen atoms, having for example from 3 to 6 carbon atoms, and which is saturated and attached to the rest of the molecule by a single bond. Unless otherwise stated specifically herein, the term "cycloalkyl" is meant to include cycloalkyl groups which are optionally substituted as described herein.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

"In vivo hydrolysable precursors" means an in vivo hydrolysable (or cleavable) ester of a compound of Formula I, Ia, Ib, II, IIa and IIb that contains a carboxy or a hydroxy group, e.g., amino acid esters, $C_{1-6}$ alkoxymethyl esters like methoxymethyl; $C_{1-6}$ alkanoyloxymethyl esters like pivaloyloxymethyl; $C_{3-8}$cycloalkoxycarbonyloxy, $C_{1-6}$ alkyl esters like acetyl, 1-cyclohexylcarbonyloxyethyl, acetoxymethoxy, or phosphoramidic cyclic esters.

"Isotopically labeled", "radiolabeled", "tracer", or "labeled tracer" compound, refers to a compound where one or more atoms are replaced or substituted by an atom having an atomic mass or mass number different from the atomic mass or mass number typically found in nature (i.e., naturally occurring). Suitable radionuclides (i.e. "detectable isotopes") that may be incorporated in compounds of the present invention include, e.g., $^{11}C$, $^{13}C$, $^{15}C$, $^{18}F$, $^{2}H$ and $^{3}H$.

"Effective amount" include amounts that enable measuring/imaging of O-GlcNAcase in vivo (i.e., diagnostically effective amount), that yield acceptable toxicity and bioavailability levels for pharmaceutical use and/or inhibit or prevent cell degeneration and toxicity associated with NFTs (i.e., therapeutically effective amount).

This invention provides compounds of the Formula (I)

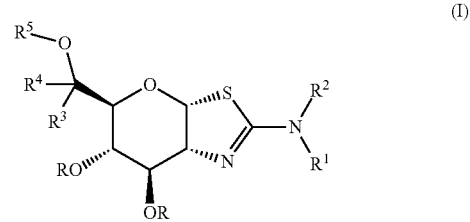

or a pharmaceutically acceptable salt, solvate or in vivo hydrolysable ester thereof, wherein, each R is independently H or $C(O)CH_3$;

$R^1$ and $R^2$ are independently (a) hydrogen, (b) C1-6alkyl optionally substituted with 1 to 3 substituents selected from F, —OH, —$OCH_3$ and —$CH_3$, or (c) C1-6alkoxy optionally substituted with 1 to 3 substituents selected from F, —OH, —$OCH_3$ and —$CH_3$; or $R^1$ and $R^2$ may be joined together with the nitrogen atom to which they are attached to form azetidine, pyrrolidine, piperidine or isoxazolidine;

$R^3$ is C1-10alkyl optionally substituted with 1 to 3 fluoro;

$R^4$ is hydrogen or C1-10alkyl optionally substituted with phenyl;

$R^5$ is (A) C1-6alkyl optionally substituted with one substituent selected from
  (1) fluoro,
  (2) morpholino,
  (3) C3-6cycloalkyl,
  (4) pyridinyl optionally substituted with C1-6alkyl,
  (5) phenyl optionally substituted with 1 to 4 substituents selected from:
    (a) fluoro, (b) hydroxy, (c) C1-6alkyl optionally substituted with 1 to 3 fluoro, (d) C1-6alkenyl, (e) C1-5alkoxy optionally substituted with 1 to 3 fluoro, (f) phenyl, (g) phenyloxy, (h) benzyloxy and (i) C1-10alkylphenyl;

(B) phenyl optionally substituted with one substituent selected from 1) —NO$_2$, 2) NH$_2$, 3) fluoro, 4) C1-6alkyl optionally substituted with fluoro and 5) C1-6alkoxy optionally substituted with fluoro; and (C) pyridinyl optionally substituted with one substituent selected from 1) fluoro, 2) C1-6alkyl optionally substituted with fluoro and 3) C1-6alkoxy optionally substituted with fluoro.

As will be appreciated by a person skilled in the art, Formula (I) above may also be represented alternatively as follows:

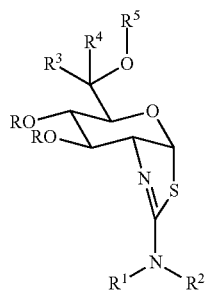

or a pharmaceutically acceptable salt, solvate or in vivo hydrolysable ester thereof wherein R, R$^1$, R$^2$, R$^3$, R$^4$ and R$^5$ have the definitions as defined in the previous embodiments for the compounds of Formula (I).

The compounds of the invention are highly potent (see Table 2 of the Examples), selective and permeable inhibitors of O-GlcNAcase. The compounds of the present invention also possess enhanced permeability (see Table 3 in the Examples) when compared to the permeability of structurally compounds described in PCT/US11/059668, filed Nov. 8, 2011 (see Table 4). The compounds of the invention may be useful in providing treatment of neurodegenerative diseases or conditions associated with NFT formation such as Alzheimer's disease and related tauopathies such as amyotrophic lateral sclerosis, glaucoma, schizophrenia, cancer and other diseases and disorders as indicated below. When isotopically labeled, e.g., with a positron emitting radionuclide such as $^{11}$C, certain specifically disclosed compounds are also useful as positron emission tomographic (PET) tracers for imaging O-GlcNAcase in the brain of living humans and experimental animals, i.e., measuring central occupancy of O-GlcNAcase. Imaging of O-GlcNAcase, in turn can aid in defining clinically efficacious doses of an unlabeled O-GlcNAcase inhibitor and provide information useful in selecting a drug candidate for clinical development.

In some embodiments, one or more of the compounds according to the invention exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability (P$_{eff}$) or apparent peameability (P$_{app}$) are reviewed for example by Volpe in *The AAPS Journal*, 2010, 12(4), 670-678. In some embodiments, one or more of the compounds according to the invention show enhanced permeability when tested in one or more of these assays for determining P$_{eff}$ or P$_{app}$. In some embodiments, a compound that exhibits enhanced permeability exhibits greater oral absorption. In some embodiments, a compound that exhibits enhanced permeability exhibits greater brain penetration when administered in vivo. In some embodiments, a compound that exhibits enhanced permeability achieves higher brain concentrations when administered in vivo. In some embodiments, a compound that exhibits enhanced permeability exhibits a higher brain/plasma concentration ratio when administered in vivo. In some embodiments, "enhanced permeability" means an increase in measured P$_{eff}$ or P$_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, (3aR,5R,6S,7R,7aR)-5-(hydroxymethyl)-2-propyl-5,6,7,7a-tetrahydro-3aH-pyrano[3,2-d]thiazole-6,7-diol, or (3aR,5R,6S,7R,7aR)-2-(ethylamino)-5-(hydroxymethyl)-5,6,7,7a-tetrahydro-3aH-pyrano[3,2-d]thiazole-6,7-diol, or (3aR,5R,6S,7R,7aR)-2-(dimethylamino)-5-(hydroxymethyl)-5,6,7,7a-tetrahydro-3aH-pyrano[3,2-d] thiazole-6,7-diol. In some embodiments, "enhanced permeability" means a measurable P$_{app}$ value (i.e. a value greater than zero) in the assay described below for determination of P$_{app}$ in LLC-PK1 cells. In some embodiments, "enhanced permeability" means a P$_{app}$ value greater than 2×10$^{-6}$ cm/s in the assay described below for determination of P$_{app}$ in LLC-PK1 cells. In some embodiments, "enhanced permeability" means a P$_{app}$ value greater than 1×10$^{-6}$ cm/s in the assay described below for determination of P$_{app}$ in LLC-PK1 cells. In alternative embodiments, "enhanced permeability" means a P$_{app}$ value in the range 2×10$^{-6}$ cm/s to 30×10$^{-6}$ cm/s in the assay described below for determination of P$_{app}$ in LLC-PK1 cells.

In some embodiments, a compound according to the invention exhibits superior selectivity in inhibiting an O-GlcNAcase. In some embodiments, one or more of the compounds according to the invention are more selective for an O-GlcNAcase over a β-hexosaminidase. In some embodiments, one or more of the compounds selectively inhibit the activity of a mammalian O-GlcNAcase over a mammalian β-hexosaminidase. In some embodiments, a selective inhibitor of an O-GlcNAcase does not substantially inhibit a β-hexosaminidase. In some embodiments, the β-hexosaminidase is a mammalian β-hexosaminidase, such as a rat, mouse or human β-hexosaminidase. A compound that "selectively" inhibits an O-GlcNAcase is a compound that inhibits the activity or biological function of an O-GlcNAcase, but does not substantially inhibit the activity or biological function of a β-hexosaminidase. For example, in some embodiments, a selective inhibitor of an O-GlcNAcase selectively inhibits the cleavage of 2-acetamido-2-deoxy-β-D-glucopyranoside (O-GlcNAc) from polypeptides. In some embodiments, a selective inhibitor of an O-GlcNAcase selectively binds to an O-GlcNAcase. In some embodiments, a selective inhibitor of an O-GlcNAcase inhibits hyperphosphorylation of a tau protein and/or inhibits formations of NFTs. By "inhibits," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase elevates or enhances O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase exhibits a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

In an embodiment of the compounds of Formula (I), $R^1$ and $R^2$ are independently hydrogen or C1-5, C1-4, C1-3, or C1-2alkyl or —$CH_3$, the alkyl being optionally substituted with 1 to 3 of the aforementioned substituents.

In another embodiment of the compounds of Formula (I), $R^3$ is C1-9, C1-8, C1-7, C1-6, C1-5, C1-4, C1-3, C1-2alkyl optionally substituted with 1 to 3 fluoro.

In another embodiment of the compounds of Formula (I), $R^3$ is methyl or trifluoromethyl.

In another embodiment of the compounds of Formula (I), $R^4$ is hydrogen.

In another embodiment of the compounds of Formula (I), $R^4$ is C1-6, C1-5, C1-4, C1-3, C1-2alkyl or —$CH_3$.

In another embodiment of the compounds of Formula (I), $R^4$ is —$CH_3$.

In another embodiment of the compounds of Formula (I), $R^4$ is ethyl optionally substituted with phenyl.

In another embodiment of the compounds of Formula (I), $R^5$ is C1-5, C1-4, C1-3, C1-2alkyl or —$CH_3$ optionally substituted with one of the aforementioned substituents.

In another embodiment of the compounds of Formula (I), the alkyl of $R^5$ is substituted with C5- or C6-cycloalkyl.

In another embodiment of the compounds of Formula (I), the alkyl of $R^5$ is optionally substituted with pyridinyl, wherein the pyridinyl is optionally substituted with —$CH_3$.

In another embodiment of the compounds of Formula (I), the alkyl of $R^5$ is optionally substituted with phenyl, wherein the phenyl is optionally substituted with 1, 2 or 3 of the aforementioned substituents.

In another embodiment of the compounds of Formula (I), the compounds are of Formula (Ia) or a pharmaceutically acceptable salt, solvate or in vivo hydrolysable ester thereof:

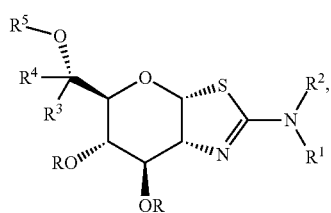

Formula (Ia)

wherein R, $R^1$, $R^2$, $R^3$, $R^4$ and $R^5$ have the definitions as defined in the previous embodiments for the compounds of Formula (I).

In another embodiment of the compounds of Formula (I), the compounds are of Formula (Ib) or a pharmaceutically acceptable salt, solvate or in vivo hydrolysable ester thereof:

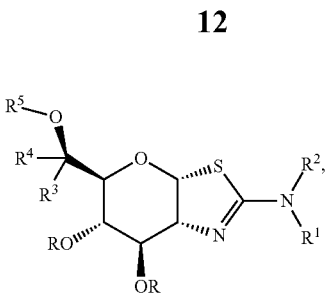

Formula (Ib)

and R, $R^1$, $R^2$, $R^3$, $R^4$ and $R^5$ have the definitions as defined in the previous embodiments for the compounds of Formula (I).

In another embodiment of the compounds of Formula (I), (Ia) and (Ib) or a pharmaceutically acceptable salt, solvate or in vivo hydrolysable ester thereof, $R^3$ is methyl or trifluoromethyl;

$R^4$ is hydrogen; and $R^5$ is C1-6alkyl optionally substituted with one substituent selected from (1) fluoro, (2) morpholino, (3) C3-6cycloalkyl, (4) pyridinyl optionally substituted with C1-6alkyl, (5) phenyl optionally substituted with 1 to 3 substituents selected from:

(a) fluoro, (b) hydroxy, (c) C1-6alkyl optionally substituted with fluoro, an (d) C1-6alkenyl, (e) C1-5alkoxy optionally substituted with fluoro, (f) phenyl, (g) phenyloxy, (h) benzyloxy and (i) C1-6alkylphenyl.

In another embodiment of the compounds of Formula (I), (Ia) and (Ib) or a pharmaceutically acceptable salt, solvate or in vivo hydrolysable ester thereof, $R^3$ is methyl or trifluoromethyl, $R^4$ is hydrogen; and $R^5$ is phenyl optionally substituted with one substituent selected from (1) —$NO_2$, (2) —$NH_2$, (3) fluoro, (4) C1-6alkyl optionally substituted with fluoro and (5) C1-6alkoxy optionally substituted with fluoro.

In another embodiment of the compounds of Formula (I), (Ia) and (Ib) or a pharmaceutically acceptable salt, solvate or in vivo hydrolysable ester thereof, $R^3$ is methyl or trifluoromethyl; $R^4$ is hydrogen; and $R^5$ is pyridinyl optionally substituted with one substituent selected from 1) fluoro, 2) C1-6alkyl optionally substituted with fluoro and 3) C1-6alkoxy optionally substituted with fluoro.

In another embodiment of the compounds of Formula (I), (Ia) and (Ib) or a pharmaceutically acceptable salt, solvate or in vivo hydrolysable ester thereof, the compound is selected from the group consisting of Examples 1-11, 20-111, 118, 119 and 120 or a pharmaceutically acceptable salt, solvate or in vivo hydrolysable ester thereof.

This invention also provides compounds of Formula (II):

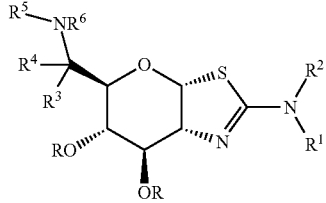

or a pharmaceutically acceptable salt, solvate or in vivo hydrolysable ester thereof, wherein each R is independently H or C(O)CH$_3$;

R$^1$ and R$^2$ are independently (a) hydrogen, (b) C1-6alkyl optionally substituted with 1 to 3 substituents selected from F, —OH, —OCH$_3$ and —CH$_3$, or (c) C1-6alkoxy optionally substituted with 1 to 3 substituents selected from F, —OH, —OCH$_3$ and —CH$_3$; or R$^1$ and R$^2$ may be joined together with the nitrogen atom to which they are attached to form azetidine, pyrrolidine, piperidine or isoxazolidine;

R$^3$ is C1-10alkyl optionally substituted from 1 to 3 fluoro;

R$^4$ and R$^5$ are independently hydrogen or C1-6 alkyl; and

R$^6$ is hydrogen, C1-6alkyl or C3-6cycloalkyl.

In an embodiment of the compounds of Formula (II) or a pharmaceutically acceptable salt, solvate or in vivo hydrolysable ester thereof, R$^1$ and R$^2$ are independently hydrogen, or C1-3alkyl or —CH$_3$;

R$^3$ is —CH$_3$ or —CF$_3$;

R$^4$ is hydrogen;

R$^5$ is hydrogen or —CH$_3$; and

R$^6$ is —CH$_3$, —CH$_2$CH$_3$ or cyclopentyl.

As will be appreciated by a person skilled in the art, Formula (II) above may also be represented alternatively as follows:

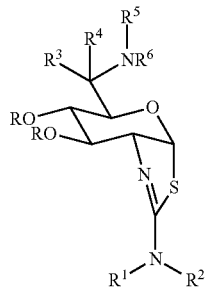

or a pharmaceutically acceptable salt, solvate or in vivo hydrolysable ester thereof, wherein R, R$^1$, R$^2$, R$^3$, R$^4$, R$^5$ and R$^6$ have the definitions as defined in the previous embodiments for the compounds of Formula (II).

In another embodiment of the compounds of Formula (II), the compounds are of Formula (IIa) or a pharmaceutically acceptable salt, solvate or in vivo hydrolysable ester thereof:

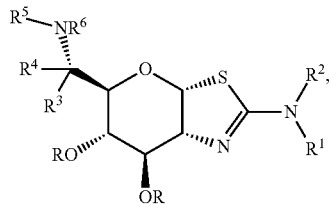

Formula (IIa)

and R, R$^1$, R$^2$, R$^3$, R$^4$, R$^5$ and R$^6$ have the definitions as defined in the previous embodiments for the compounds of Formula (II).

In another embodiment of the compounds of Formula (II), the compounds are of Formula (IIb) or a pharmaceutically acceptable salt, solvate or in vivo hydrolysable ester thereof:

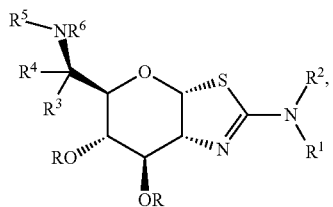

Formula (IIb)

and R, R$^1$, R$^2$, R$^3$, R$^4$, R$^5$ and R$^6$ have the definitions as defined in the previous embodiments for the compounds of Formula (II).

In another embodiment of the compounds of Formula (II), the compounds are selected from the group consisting of Examples 12-19, 112-115 and 116 or a pharmaceutically acceptable salt, solvate or in vivo hydrolysable ester thereof.

In another embodiment, the compounds of the Formulas (I), (Ia), (Ib), (II), (IIa), and (IIb) also include isotopically labeled compounds. Suitable radionuclides (i.e. "detectable isotopes") that may be incorporated in compounds of the invention include but are not limited to $^{11}$C, $^{13}$C, $^{14}$C, $^{18}$F, $^{2}$H and $^{3}$H, and preferably $^{11}$C. The isotopically labeled compounds of the invention need only to be enriched with a detectable isotope to, or above, the degree which allows detection with a technique suitable for the particular application. The radionuclide that is incorporated in the instant radiolabeled compounds will depend on the specific application of that radiolabeled compound.

In another embodiment, the compounds of Formula (I) are selected from the group consisting of Examples 118-120 or a pharmaceutically acceptable salt, solvate or in vivo hydrolysable ester thereof, and in further embodiments these compounds are isotopically labeled with $^{11}$C.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190).

Salts of the compounds of the invention will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

Salts of the compounds which are in basic form may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As the compounds according to the invention have pharmacological properties, i.e., the compounds can selectively inhibit O-GlcNAcase and exhibit both high potency and high permeability, they may be useful in the treatment or prevention of neurodegenerative diseases, e.g., Alzheimer's disease and other neurodegenerative diseases or conditions and related tauopathies. Related tauopathies include but are not limited to Amyotrophic lateral sclerosis, Amyotrophic lateral sclerosis with cognitive impairment, Argyrophilic grain dementia, Bluit disease, Corticobasal degeneration, Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease, Post-encephalitic parkinsonism, Prion diseases (including Creutzfeldt-Jakob Disease, Variant Creutzfeldt-Jakob Disease, Fatal Familial Insomnia, and Kuru), Progressive supercortical gliosis, Progressive supranuclear palsy, Richardson's syndrome, Subacute sclerosing panencephalitis, and Tangle-only dementia.

The compounds of the invention may also be useful for treatment of neurodegenerative diseases, including Parkinson's disease and Huntington's disease. Other conditions that may be treated are those triggered, affected, or in any other way correlated with levels of O-GlcNAc post-translational protein modification. It is expected that the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Compounds that selectively inhibit O-GlcNAcase activity may also be used for the treatment of diseases that are associated with inflammation, including but not limited to, of an inflammatory disease, an allergy, asthma, allergic rhinitis, hypersensitivity lung diseases, hypersensitivity pneumonitis, eosinophilic pneumonias, delayed-type hypersensitivity, atherosclerosis, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis or dermatomyositis, systemic anaphylaxis or hypersensitivity response, drug allergy, insect sting allergy, autoimmune disease, rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, allograft rejection, graft-versus-host disease, inflammatory bowel disease, Crohn's disease, ulcerative colitis, spondyloarthropathy, scleroderma, psoriasis, T-cell mediated psoriasis, inflammatory dermatosis, dermatitis, eczema, atopic dermatitis, allergic contact dermatitis, urticaria, vasculitis, necrotizing, cutaneous, and hypersensitivity vasculitis, eosinphilic myotis, eosiniphilic fasciitis, solid organ transplant rejection, heart transplant rejection, lung transplant rejection, liver transplant rejection, kidney transplant rejection, pancreas transplant rejection, kidney allograft, lung allograft, epilepsy, pain, fibromyalgia, stroke, and neuroprotection.

In addition, compounds that affects levels of protein O-GlcNAc modification may be used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

The compounds of this invention may also be useful in the treatment of conditions associated with tissue damage or stress, stimulating cells, or promoting differentiation of cells. Accordingly, in some embodiments, a compound of this invention may be used to provide therapeutic benefit in a variety of conditions or medical procedures involving stress in cardiac tissue, including but not limited to: ischemia; hemorrhage; hypovolemic shock; myocardial infarction; an interventional cardiology procedure; cardiac bypass surgery; fibrinolytic therapy; angioplasty; and stent placement.

The compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition requiring modulation of O-GlcNAcase activity.

In an embodiment, a method of treating a disease or disorder selected from the group consisting of Alzheimer's disease and related tauopathies, glaucoma, schizophrenia, Huntington's disease, Parkinson's disease, mild cognitive impairment, neuropathy (including peripheral neuropathy, autonomic neuropathy, neuritis, diabetic neuropathy) and cancer is provided, the method comprising administering to a subject in need thereof a therapeutically effective amount of a compound of the invention or a pharmaceutically acceptable salt, solvate or in vivo hydrolysable ester thereof, or a pharmaceutical composition of the compound, salt or ester.

In another embodiment of the method of treatment of Alzheimer's disease and related tauopathies, glaucoma, schizophrenia, Huntington's disease, Parkinson's disease, mild cognitive impairment, neuropathy (including peripheral neuropathy, autonomic neuropathy, neuritis, diabetic neuropathy) and cancer, a compound of the invention or a pharmaceutically acceptable salt, solvate or in vivo hydrolysable ester thereof, or a pharmaceutical composition comprising the compound or a pharmaceutically acceptable salt, solvate or in vivo hydrolysable ester thereof is administered concurrently, simultaneously, sequentially or separately with another pharmaceutically active compound or compounds used in Alzheimer's therapies including for example donepezil, memantine, tacrine and equivalents and pharmaceutically active isomer(s) and metabolite(s) thereof.

In some embodiments, a compound according to the invention, or for use according to the invention, may be provided in combination with any other active agents or pharmaceutical compositions where such combined therapy is useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (ZT-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-Z1, CTS-21166, MK-8931, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfurindamide, LiCl, AZD1080, NP031112, SAR-502250, etc.;

humanized monoclonal anti-A13 antibodies such as Bapineuzumab (AAB-001), LY2062430, RN1219, ACU-5A5, etc.;

amyloid vaccines such as AN-1792, ACC-001, etc.;

neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

The O-GlcNAcase inhibitors will generally be administered orally. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compositions including the compounds of the invention, or for use according to the invention, are contemplated as being within the scope of the invention. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers. By "pharmaceutically acceptable" it is meant the carrier, diluent or excipient must be compatible with the other ingredients of the formulation and not deleterious to the recipient thereof. The terms "administration of" and or "administering a" compound should be understood to mean providing a compound of the invention, or pharmaceutically acceptable salt or in vivo hydrolysable ester thereof to the subject. The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The invention also provides a method for diagnostic imaging (i.e., measuring central occupancy) of O-GlcNAcase in a mammal, e.g., a rodent, non-human primate or human, which comprises administering to the mammal in need of such diagnostic imaging an effective amount of the isotopically labeled compound selected from Examples 118-120 or a pharmaceutically acceptable salt, solvate or in vivo hydrolysable ester thereof.

The invention also provides a method for diagnostic imaging of the brain in a mammal which comprises administering to the mammal in need of such diagnostic imaging an effective amount of the isotopically labeled compound selected from Examples 118-120 or a pharmaceutically acceptable salt, solvate or in vivo hydrolysable ester thereof.

The invention also provides a method for the detection or quantification of O-GlcNAcase in mammalian tissue, e.g., brain, the method comprising contacting the mammalian tissue in which such detection is desired with an effective amount of the isotopically labeled compound selected from Examples 118-120 or a pharmaceutically acceptable salt, solvate or in vivo hydrolysable ester thereof.

The invention is also, in part, to develop radiolabeled O-GlcNAcase inhibitors that would be useful not only in traditional exploratory and diagnostic imaging applications, but also be useful in assays, both in vitro and in vivo for labeling the O-GlcNAcase enzyme and for competing with unlabeled O-GlcNAcase inhibitors. Using an $^{18}F$ or $^{11}C$ labeled radiotracer that provides an O-GlcNAcase specific image in the brain and other tissues, the dose necessary to saturate O-GlcNAcase enzyme can be determined by the blockade of the PET radiotracer image in humans. In particular, a method of determining the plasma concentration/occupancy relationship of an unlabeled O-GlcNAcase inhibitor is provided, wherein the method comprises administering to the subject such as a human an effective amount of an isotopically labeled compound selected from Examples 118-120 or a pharmaceutically acceptable salt, solvate or in vivo hydrolysable ester thereof. As indicated above, radionuclides that may be incorporated in the instant compounds include but are not limited to $^{11}C$, $^{13}C$, $^{14}C$, $^{18}F$ and $^{3}H$, and preferably $^{11}C$.

In an embodiment of the aforementioned methods of the invention, the mammal is e.g., a rodent, a non-human primate or a human.

In another embodiment of the aforementioned methods of the invention, diagnostic imaging of O-GlcNAcase is carried out by performing PET imaging, magnetic resonance imaging, or autoradiography.

Isotopically labeled compounds of the invention are potentially useful for diagnostic imaging, basic research, and radiotherapeutic applications. Specific examples of possible diagnostic imaging and radiotherapeutic applications, include determining the location, the relative activity or abundance of O-GlcNAcase, radioimmunoassay of O-GlcNAcase, and autoradiography to determine the distribution of O-GlcNAcase in the brain of a mammal.

In particular, these isotopically labeled compounds, in particular the compounds of Examples 118-120 or pharmaceutically acceptable salts, solvate or in vivo hydrolysable esters thereof, when labeled with the positron emitting radionuclide, $^{11}C$, are useful for PET imaging of O-GlcNAcase in the brain of living humans and experimental animals. These isotopically labeled compounds may be used as research tools to study the interaction of unlabeled O-GlcNAcase inhibitors with O-GlcNAcase in vivo via competition between the unlabeled drug and the radiolabeled compound for binding to the enzyme. These types of studies are useful for determining the relationship between O-GlcNAcase occupancy and dose of unlabeled O-GlcNAcase inhibitor, as well as for studying the duration of blockade of the enzyme by various doses of the unlabeled O-GlcNAcase inhibitor. As a clinical tool, the radiolabeled O-GlcNAcase inhibitors may be used to help define a clinically efficacious dose of an O-GlcNAcase inhibitor. In animal experiments, the radiolabeled O-GlcNAcase inhibitors can be used to provide information that is useful for choosing between potential drug candidates for selection for clinical development. The radiolabeled O-GlcNAcase inhibitors may also be used to study the regional distribution and concentration of O-GlcNAcase in the living human brain, as well as the brain of living experimental animals and in tissue samples. The radiolabeled O-GlcNAcase inhibitors may also be used to study disease or pharmacologically related changes in O-GlcNAcase concentrations.

For example, PET tracers such as the present radiolabeled O-GlcNAcase inhibitors which can be used with currently available PET technology to obtain the following information: relationship between level of receptor occupancy by candidate O-GlcNAcase inhibitors and clinical efficacy in subjects; dose selection for clinical trials of O-GlcNAcase prior to initiation of long term clinical studies; comparative potencies of structurally novel O-GlcNAcase inhibitors; investigating the influence of O-GlcNAcase inhibitors on in vivo affinity and density during the treatment of clinical targets with O-GlcNAcase inhibitors and other agents; changes in the density and distribution of O-GlcNAcase during e.g. Alzheimer's disease in its active stages, during effective and ineffective treatment and during remission; and changes in O-GlcNAcase expression and distribution in CNS disorders, imaging neurodegenerative disease where O-GlcNAcase are involved; and the like.

As indicated above, it is well established that Alzheimer's disease and a number of related tauopathies as described below are characterized, in part, by the development of NFTs and that a malfunction in the mechanisms regulating tau O-GlcNAc levels, e.g, by regulating O-GlcNAcase, may be vitally important in the formation of NFTs and associated neurodegeneration. Accordingly, the radiolabeled compounds of the invention also have utility in diagnostic imaging with respect to a variety of neurological and psychiatric disorders associated with NFT formation including Alzheimer's disease and related tauopathies as described above, glaucoma, schizophrenia, and cancer.

For the use of the instant compounds as exploratory or diagnostic imaging agents the radiolabeled compounds may be administered to mammals, preferably humans, in a pharmaceutical composition, either alone or, preferably, in combination with one or more pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous. Radiotracers labeled with short-lived, positron emitting radionuclides are generally administered via intravenous injection within less than one hour of their synthesis. This is necessary because of the short half-life of the radionuclides involved (20 and 110 minutes for $^{11}C$ and $^{18}F$, respectively).

When a radiolabeled inhibitor according to this invention is administered into a human subject, the amount required for diagnostic imaging will normally be determined by the prescribing physician with the dosage generally varying according to the age, weight, and response of the individual subject, as well as the quantity of emission from the radionuclide. However, in most instances, an effective amount will be the amount of compound sufficient to produce emissions in the range of from about 1-10 mCi.

In one exemplary application, administration occurs in an amount of radiolabeled compound of between about 0.005 μg/kg of body weight to about 50 μg/kg of body weight per day, preferably of between 0.02 μg/kg of body weight to about 7 μg/kg of body weight. A particular analytical dosage that comprises the instant composition includes from about 0.5 μg to about 100 μg of the isotopically labeled compound. Preferably, the dosage comprises from about 1 μg to about 50 μg of the isotopically labeled compound.

The following illustrative procedure may be utilized when performing PET imaging studies on subjects in the clinic. The subject undergoes a baseline scan as described below, after which the subject is premedicated with unlabeled O-GlcNAcase inhibitor for the desired time prior to the day of the experiment and is fasted for at least 12 hours allowing water intake ad libitum. A 20 G two inch venous catheter is inserted into the contralateral ulnar vein for radiotracer administration.

The subject is positioned in the PET camera and a tracer dose of $[^{15}O]$ $H_2O$ administered via i.v. catheter. The image thus obtained is used to insure that the subject is positioned correctly to include the brain or other areas of interest. Subsequently the isotopically labeled O-GlcNAcase inhibitor, e.g., compound labeled with $^{11}C$ (<10 mCi), is administered via i.v. catheter. Images are acquired for up to 180 min. Within ten minutes of the injection of radiotracer and at the end of the imaging session, 1 ml blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of O-GlcNAcase inhibitor or in the presence of the clinical candidate at the various infusion doses examined. Data are expressed as radioactivity per unit time per unit volume (μCi/cc/mCi injected dose). Inhibition curves are generated from the data obtained in a region of interest obtained starting at 70 minutes post-injection of radiotracer. At this time, clearance of non-specific binding has reached steady state. The $ID_{50}$ values are obtained by curve fitting the dose-rate/inhibition curves with equation iii:

$$B = A_0 - A_0 * I/(ID_{50} + I) + NS \qquad (iii)$$

where B is the %-Dose/g of radiotracer in tissues for each dose of clinical candidate, $A_0$ is the specifically bound radiotracer in a tissue in the absence of a O-GlcNAcase inhibitor, I is the injected dose of antagonist, $ID_{50}$ is the dose of compound which inhibits 50% of specific radiotracer binding to O-GlcNAcase, and NS is the amount of non-specifically bond radiotracer.

In accordance with another embodiment of the present invention, there are provided methods for the preparation of compounds of invention as described below. For example, the compounds can be prepared using synthetic chemistry techniques well known in the art (see *Comprehensive Heterocyclic Chemistry*, Katritzky, A. R. and Rees, C. W. eds., Pergamon Press, Oxford, 1984) from a precursor of the compounds as outlined below. The isotopically labeled compounds of this invention are prepared by incorporating the aforementioned isotopes, e.g., into the substrate molecule. This is accomplished by utilizing reagents that have had one or more of the atoms contained therein made radioactive by placing them in a source of radioactivity such as a nuclear reactor, a cyclotron and the like. Additionally many isotopically labeled reagents, such as $^2H_2O$, $^3H_3Cl$, $^{14}C_6H_5Br$, $ClCH_2^{14}COCl$ and the like, are commercially available. The isotopically labeled reagents are then used in standard organic chemistry synthetic techniques to incorporate the isotope atom, or atoms, into a compound of the invention as described below.

In the compounds of generic Formulas (I), (Ia), (Ib), (II), (IIa) and (IIb), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1H$), deuterium ($^2H$) and tritium ($^3H$).

Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulas (I), (Ia), (Ib), (II), (IIa) and (IIb) can be prepared without undue experimentation by conventional techniques well known to those skilled in the art or by processes analogous to those described in the Schemes and Examples herein using appropriate isotopically-enriched reagents and/or intermediates.

EXAMPLES

The invention disclosed herein is exemplified by the following preparations and examples, which should not be construed to limit the scope of the disclosure.

Abbreviations used in the description of the chemistry and in the Examples that follow are:

Abbreviations
AIBN=2,2'-Azobisisobutyronitrile
DAST=(Diethylamino)sulfur trifluoride
DCM=dichloromethane
DIBAL-H=Diisobutylaluminum hydride
DMAP=4-dimethylaminopyridine
DMF=N,N-dimethylformamide
DMP=Dess-Martin periodinane
DMSO=dimethyl sulfoxide
EDC=1-(3-Dimethylaminopropyl)-3-ethlycarbodiimide hydrochloride
NBS=N-bromosuccinimide
PMBBr=para-methoxy benzyl bromide
TBAB=tetra-n-butylammonium bromide
TBAF=tetra-n-butylammonium fluoride
TEA=triethylamine
TEAF=tetraethylammonium fluoride
TEMPO=2,2,6,6-tetramethyl-piperidin-1-oxy free radical
TFA=2,2,2-trifluoroacetic acid
THF=tetrahydrofuran Synthesis of Intermediates 1,3,4,6-tetra-O-acetyl-2-deoxy-2-isothiocyanate-β-D-glucopyranose

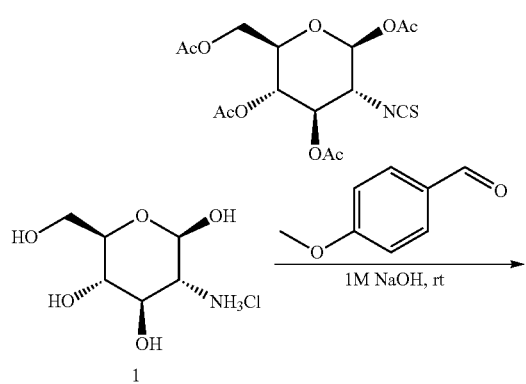

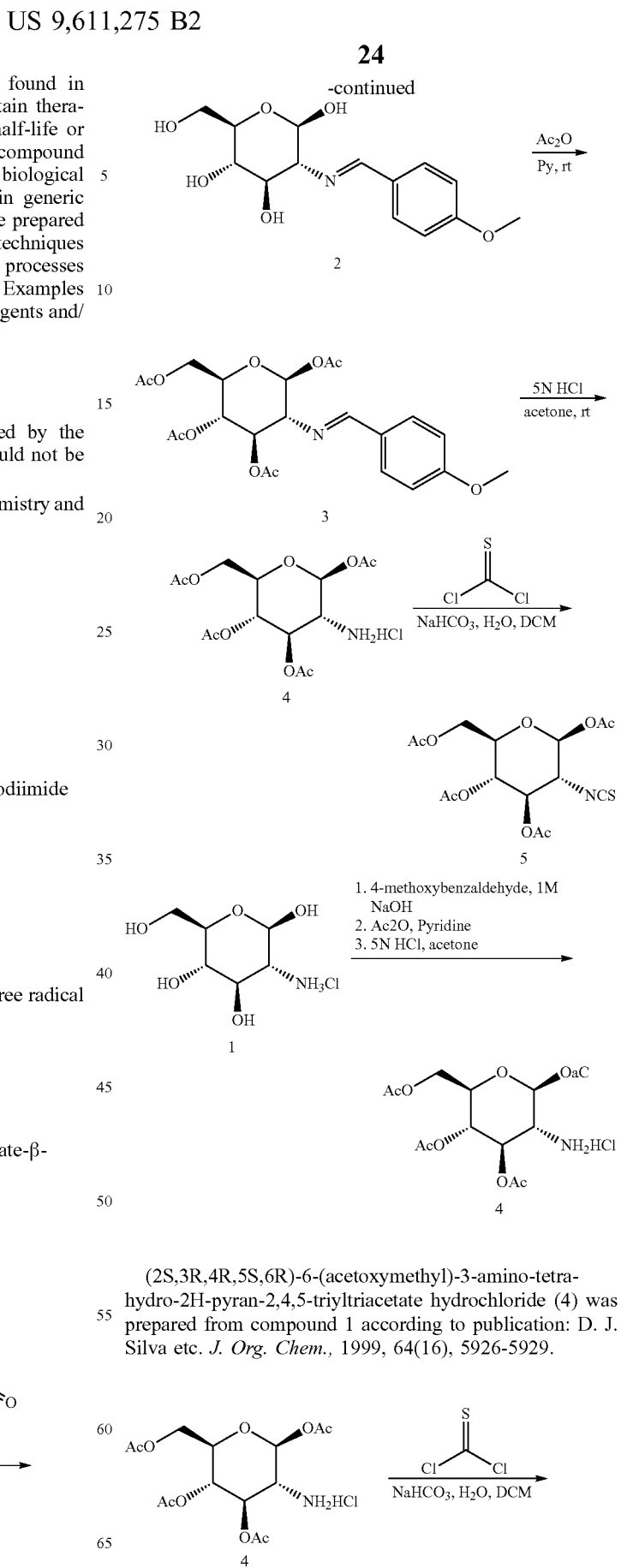

(2S,3R,4R,5S,6R)-6-(acetoxymethyl)-3-amino-tetrahydro-2H-pyran-2,4,5-triyltriacetate hydrochloride (4) was prepared from compound 1 according to publication: D. J. Silva etc. *J. Org. Chem.*, 1999, 64(16), 5926-5929.

25

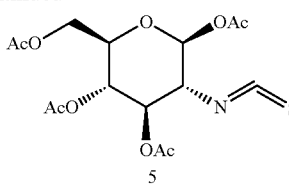

(2S,3R,4R,5S,6R)-6-(acetoxymethyl)-3-isothiocyanato-tetrahydro-2H-pyran-2,4,5-triyl triacetate (5) was prepared from compound 4 according to publication: M. V. Gonzalez etc. *Carbohydrate Research*, 1986, 154, 49

Example 1

(3aR,5S,6S,7R,7aR)-2-(dimethylamino)-5-((S)-2,2,2-trifluoro-1-methoxyethyl)-5,6,7,7a-tetrahydro-3aH-pyrano[3,2-d]thiazole-6,7-diol

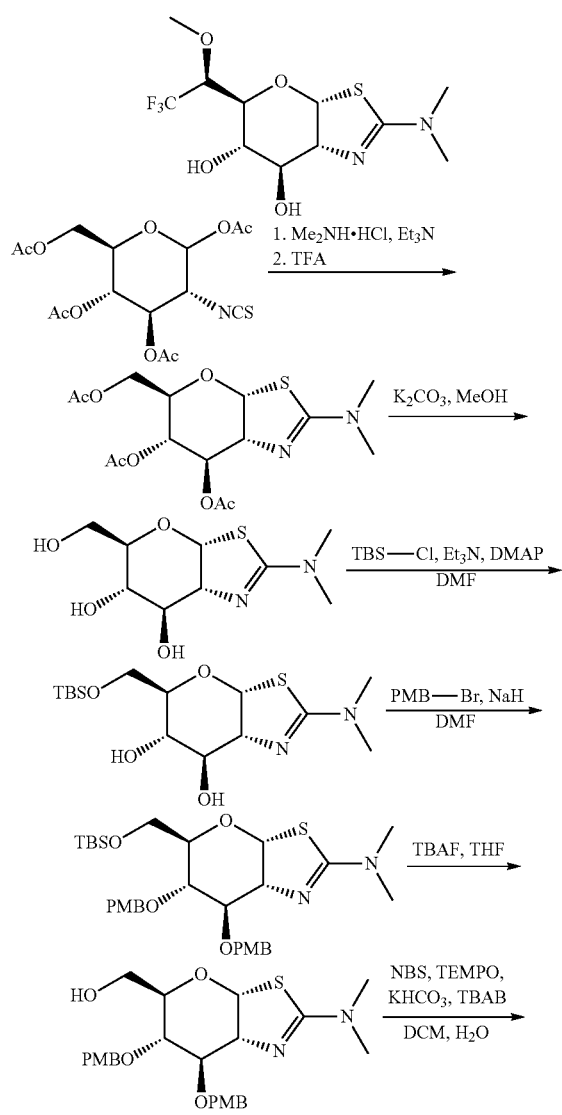

26

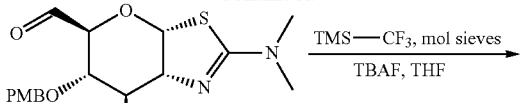

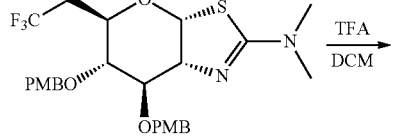

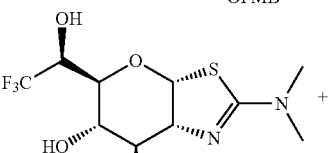

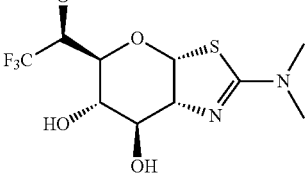

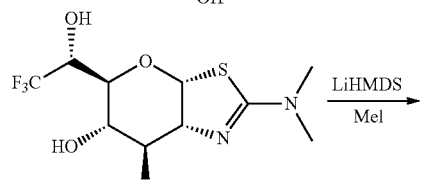

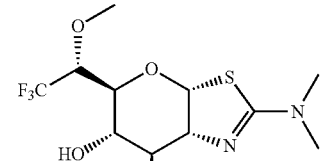

(3aR,5R,6S,7R,7aR)-5-(Acetoxymethyl)-2-(dimethylamino)-5,6,7,7a-tetrahydro-3aH-pyrano[3,2-d]thiazole-6,7-diyl diacetate To a solution of (3R,4R,5S,6R)-6-(acetoxymethyl)-3-isothiocyanato-tetrahydro-2H-pyran-2,4,5-triyltriacetate (2 g, 5.14 mmol) in dichloromethane (20 mL) was added dimethylamine hydrochloride (460 mg, 5.64 mmol) and triethylamine (675 mg, 6.68 mmol) at 5~10° C. After stirred for 3 h, the reaction mixture was treated with TFA (1.6 g, 14 mmol) overnight at room temperature. The reaction mixture was washed with saturated sodium bicarbonate (50 mL), dried over anhydrous magnesium sulfate, and concentrated under vacuum to provide a residue, which was purified by silica gel column, eluted with 1% MeOH in dichloromethane to give compound (3aR,5R,6S,7R,7aR)-5-(Acetoxymethyl)-2-(dimethylamino)-5,6,7,7a-tetrahydro-3aH-pyrano[3,2-d]thiazole-6,7-diyl diacetate as yellow oil (1.65 g, 85%). (ES, m/z): [M+H]$^+$ 374.9; $^1$H NMR (300 MHz, CDCl$_3$) δ 6.24-6.26 (d, J=6.6 Hz, 1H), 5.31-5.43 (m, 1H), 4.94-4.99 (m, 1H), 4.34-4.38 (t, J=10.8 Hz, 1H), 4.16-4.22 (m, 2H), 4.38-4.39 (m, 1H), 3.02 (s, 6H), 2.06-2.12 (m, 9H).

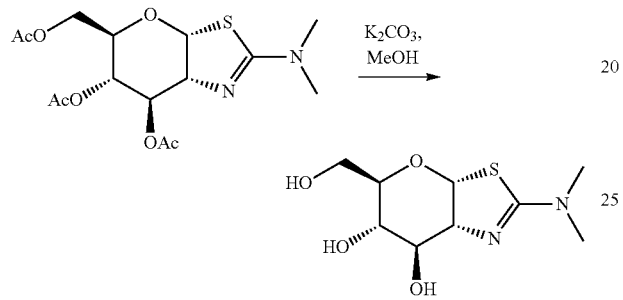

(3aR,5R,6S,7R,7aR)-2-(Dimethylamino)-5-(hydroxymethyl)-5,6,7,7a-tetrahydro-3aH-pyrano[3,2-d]thiazole-6,7-diol To a solution of (3aR,5R,6S,7R,7aR)-5-(acetoxymethyl)-2-(dimethylamino)-5,6,7,7a-tetrahydro-3aH-pyrano[3,2-d]thiazole-6,7-diyl diacetate (1.65 g, 4.41 mmol) in methanol (20 mL) was added potassium carbonate (25 mg, 0.18 mmol). The resulting mixture was stirred overnight at room temperature to yield a solid. This was collected by filtration, washed with cold methanol and dried. The product was obtained as a light yellow solid (1.05 g, 94%). (ES, m/z): [M+H]$^+$ 248.9; $^1$H NMR (300 MHz, CDCl$_3$) δ 6.33-6.35 (d, J=6.3 Hz, 1H), 4.29-4.33 (t, J=6.0 Hz 1H), 4.16 (s, 1H), 3.76-3.89 (m, 2H), 3.70 (s, 2H), 3.03 (s, 6H).

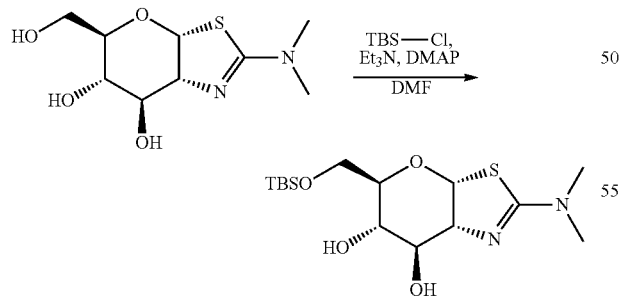

(3aR,5R,6S,7R,7aR)-5-((tert-Butyldimethylsilyloxy)methyl)-2-(dimethylamino)-5,6,7,7a-tetrahydro-3aH-pyrano[3,2-d]thiazole-6,7-diol To a solution of (3aR,5R,6S,7R,7aR)-2-(dimethylamino)-5-(hydroxymethyl)-5,6,7,7a-tetrahydro-3aH-pyrano[3,2-d]thiazole-6,7-diol (1 g, 4.03 mmol), DMAP (49.2 mg, 0.40 mmol) and triethylamine (611 mg, 6.05 mmol) in DMF (50 mL) was added tert-butylchlorodimethylsilane (665 mg, 4.43 mmol). After stirred overnight at 50° C., the resulting mixture was concentrated under vacuum to provide a residue, which was purified by silica gel column, eluted with 2-5% MeOH in dichloromethane to give the title compound as a yellow solid (1.0 g, 65%). (ES, m/z): [M+H]$^+$ 263.0; $^1$H NMR (300 MHz, CDCl$_3$) δ 6.33-6.35 (d, J=6.3 Hz, 1H), 4.35-4.39 (t, J=5.7 Hz, 1H), 4.18-4.21 (t, J=4.5 Hz, 1H), 3.81-3.84 (m, 3H), 3.62-3.67 (m, 1H), 3.05 (s, 6H), 0.93 (s, 9H), 0.11 (s, 6H).

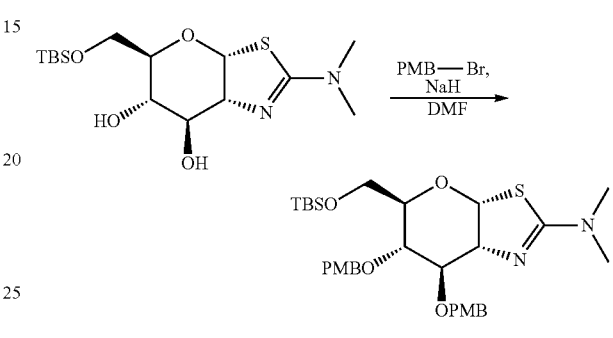

(3aR,5R,6S,7R,7aR)-5-((tert-Butyldimethylsilyloxy)methyl)-6,7-bis(4-methoxybenzyloxy)-N,N-dimethyl-5,6,7,7a-tetrahydro-3aH-pyrano[3,2-d]thiazol-2-amine To a solution of (3aR,5R,6S,7R,7aR)-5-((tert-butyldimethylsilyloxy)methyl)-2-(dimethylamino)-5,6,7,7a-tetrahydro-3aH-pyrano[3,2-d]thiazole-6,7-diol (1 g, 2.76 mmol) in DMF (20 mL) was added sodium hydride (568 mg, 16.6 mmol, 70%) at 15° C., and followed by addition of 1-(bromomethyl)-4-methoxybenzene (2.22 g, 11.0 mmol). The resulting solution was stirred for 3 h at room temperature, quenched by addition of cold water (50 mL), and extracted with dichloromethane (3×50 mL). The combined organic layers were dried over anhydrous magnesium sulfate and concentrated to give a residue, which was purified by silica gel column, eluted with 10-25% ethyl acetate in petroleum ether to give the product as a yellow oil (1.2 g, 64%). (ES, m/z): [M+H]$^+$ 603.1; $^1$H NMR (300 MHz, CDCl$_3$) δ 7.22-7.35 (m, 4H), 6.84-6.92 (m. 4H), 6.27-6.29 (d, J=6.6 Hz, 1H), 4.60-4.76 (m, 4H), 4.36-4.43 (m, 2H), 4.10-4.17 (m, 2H), 3.81 (s, 6H), 3.72 (m, 1H), 3.61 (m, 1H), 2.99 (s, 6H), 0.83 (s, 9H), 0.07 (s, 6H).

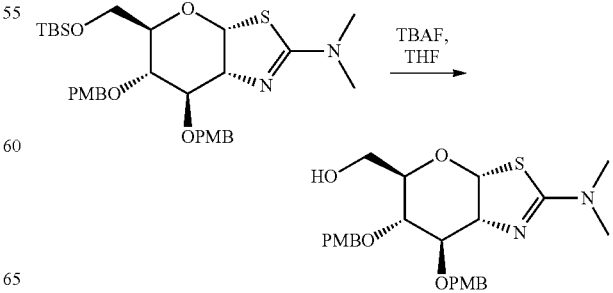

((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)methanol (3aR,5R,6S,7R,7aR)-6,7-bis(4-methoxybenzyloxy)-5-((tert-butyldimethylsilyloxy)methyl)-N,N-dimethyl-5,6,7,7a-tetrahydro-3aH-pyrano[3,2-d]thiazol-2-amine (9.5 g, 15.8 mmol) in THF (100 mL) was treated with TBAF (8.27 g, 31.6 mmol) overnight at room temperature. The resulting solution was diluted with brine (200 mL), extracted with ethyl acetate (2×200 mL), and dried over anhydrous magnesium sulfate. After removal of solvents, the residue was purified by silica gel column, eluted with 1-2.5% MeOH in dichloromethane to give the product as a yellow oil (7.0 g, 86%). (ES, m/z): [M+H]+489.0; 1H NMR (300 MHz, CDCl3) δ 7.32-7.62 (m, 2H), 7.22-7.28 (m, 2H), 6.85-6.91 (m, 4H), 6.26-6.28 (d, J=6.6 Hz, 1H), 4.52-4.73 (m, 4H), 4.31-4.34 (d, J=11.4 Hz, 1H), 4.23 (s, 1H), 3.81 (s, 6H), 3.53-3.76 (m, 4H), 3.01 (m, 6H), 1.78-1.82 (m, 1H).

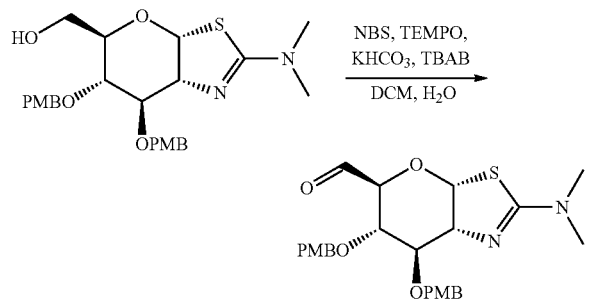

(3aR,5S,6S,7R,7aR)-2-(Dimethylamino)-6,7-bis(4-methoxybenzyloxy)-5,6,7,7a-tetrahydro-3aH-pyrano[3,2-d]thiazole-5-carbaldehyde)

To a mixture of ((3aR,5R,6S,7R,7aR)-6,7-bis(4-methoxybenzyloxy)-2-(dimethylamino)-5,6,7,7a-tetrahydro-3aH-pyrano[3,2-d]thiazol-5-yl)methanol (500 mg, 1.0 mmol), TBAB (16.5 mg, 0.05 mmol), KHCO3 (461 mg, 4.6 mmol) and TEMPO (8 mg, 0.05 mmol) in dichloromethane (25 mL) and H2O (5 mL) was added NBS (201 mg, 1.13 mmol) at 15° C. After stirred for 30 min, the reaction mixture was quenched by saturated Na2SO3 (5 mL). The organic layer was dried over anhydrous magnesium sulfate and condensed to provide a residue, which was purified by silica gel column, eluted with 20-30% ethyl acetate in dichloromethane to give the product as a yellow syrup (320 mg, 75% pure). (ES, m/z): [M+H]+ 487.0. 1H NMR (300 MHz, CDCl3) δ 9.61 (s, 1H), 7.22-7.34 (m, 4H), 6.83-6.92 (m, 4H), 6.11-6.13 (d, J=6.0 Hz, 1H), 4.17-4.67 (m, 8H), 3.83 (s, 6H), 3.00-3.04 (s, 6H).

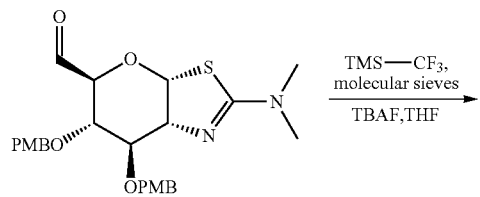

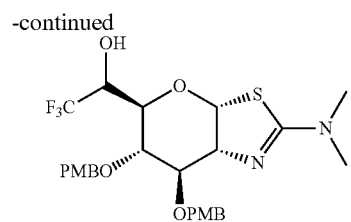

1-((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)-2,2,2-trifluoroethanol (Mixture of Two Diastereomers)

To a stirred mixture of TBAF (107 mg, 0.41 mmol) and 4 Å molecule sieves in THF (20 mL) was added a solution of (3aR,5S,6S,7R,7aR)-2-(dimethylamino)-6,7-bis(4-methoxybenzyloxy)-5,6,7,7a-tetrahydro-3aH-pyrano[3,2-d]thiazole-5-carbaldehyde (400 mg, 0.82 mmol) and TMS-CF3 (230 mg, 1.64 mmol) in THF (5 mL) at 0° C. After stirring for 4 hours at 0° C., the reaction was quenched by brine (30 mL), and extracted with ethyl acetate (3×20 mL). The combined organic layers were dried over anhydrous sodium sulfate and concentrated under reduced pressure to provide a residue, which was purified by silica gel column, eluted with 2-3% methanol in dichloromethane to give the title compound as a yellow syrup (300 mg, 65%, a mixture of diastereomers, faster eluting isomer:slower moving isomer=1:2 by Chiral-HPLC). (ES, m/z): [M+H]+ 557.0; 1H NMR (300 MHz, CDCl3) δ 7.20-7.35 (m, 4H), 6.85-6.92 (m, 4H), 6.25-6.27 (d, J=6.6 Hz, 1H), 4.56-4.69 (m, 5H), 4.30-4.36 (m, 2H), 3.82-3.83 (m, 8H), 2.99-3.00 (m, 6H).

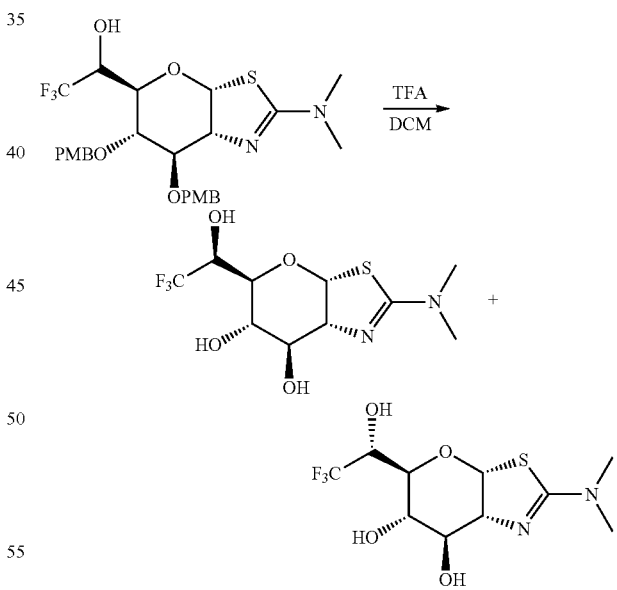

(3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol and (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol A solution of 1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)-2,2,2-trifluoroethanol (a mixture of two diastereomers from previous step) (400 mg, 0.72 mmol) in dichloromethane (20 mL) was treated with TFA (2 mL) for 1 h at room temperature. The reaction mixture was concentrated under reduced pressure to give a residue, which was purified by Prep-HPLC under the following conditions [(Agilent 1200 prep HPLC): Column, SunFire Prep C18, 19*50 mm 5 um; mobile phase, water with 0.03% NH$_4$OH and CH$_3$CN (10% CH$_3$CN up to 45% in 10 min); Detector, UV 220 nm] to afford (3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol as a white solid (faster eluting isomer, 62 mg, 27%): (ES, m/z): [M+H]$^+$ 316.9; $^1$H NMR (300 MHz, D$_2$O) δ 6.19-6.21 (d, J=6.6 Hz, 1H), 4.22-4.27 (m, 1H), 4.04 (t, J=6.6 Hz, 1H), 3.86-3.90 (m, 1H), 3.71-3.76 (m, 1H), 2.93 (s, 6H); (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol as a white solid (slower eluting isomer, 55 mg, 24%). (ES, m/z): [M+H]$^+$ 316.9; $^1$H NMR (300 MHz, D$_2$O) δ 6.25-6.27 (d, J=6.3 Hz, 1H), 4.26-4.34 (m, 1H), 4.10 (t, J=6.0 Hz, 1H), 3.94 (t, J=5.4 Hz, 1H), 3.72-3.82 (m, 1H), 2.92 (s, 6H).

Example 2

(3aR,5S,6S,7R,7aR)-2-(dimethylamino)-5-((R)-2,2,2-trifluoro-1-methoxyethyl)-5,6,7,7a-tetrahydro-3aH-pyrano[3,2-d]thiazole-6,7-diol

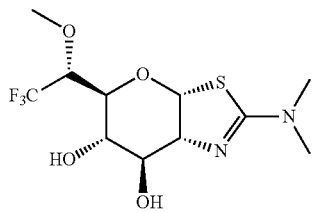 [SMILES: CO[C@H]([C@H]1O[C@@H]2SC(N(C)C)=N[C@@H]2[C@@H](O)[C@@H]1O)C(F)(F)F]

Scheme II

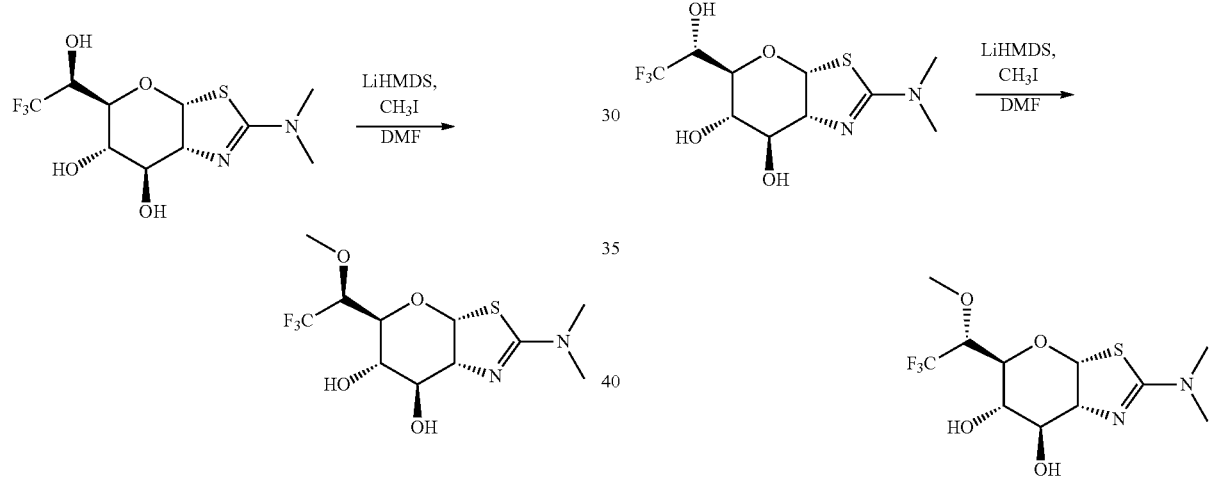

(3aR,5S,6S,7R,7aR)-2-(dimethylamino)-5-((S)-2,2,2-trifluoro-1-methoxyethyl)-5,6,7,7a-tetrahydro-3aH-pyrano[3,2-d]thiazole-6,7-diol A solution of (3aR,5S,6S,7R,7aR)-2-(dimethylamino)-5-((S)-2,2,2-trifluoro-1-hydroxyethyl)-5,6,7,7a-tetrahydro-3aH-pyrano[3,2-d]thiazole-6,7-diol (450 mg, 1.4 mmol) in DMF (30 mL) was treated with LiHMDS (1.8 mL, 1.8 mmol, 1M in THF) at 0° C. for 10 min, and followed by addition of CH$_3$I (300 mg, 2.1 mmol). After additional 1 hour at room temperature the reaction was quenched by saturated aqueous NH$_4$Cl solution (15 mL) and extracted with ethyl acetate (3×20 mL). The combined organic layer was dried over anhydrous magnesium sulfate and concentrated under vacuum. The residue was purified by flash column chromatography with 2%-10% methanol in dichloromethane to afford the title compound as a white solid (192 mg, 40%). (ES, m/z): [M+H]$^+$ 331.0; $^1$H NMR (300 MHz, D$_2$O): 6.15 (d, J=6.6 Hz, 1H), 4.19 (t, J=5.4 Hz, 2H), 3.98-4.03 (m, 2H), 3.83 (dd, J=3.6 Hz, 3.3 Hz, 1H), 3.73 (dd, J=5.4 Hz, 3.6 Hz, 1H), 3.50 (s, 3H), 2.88 (s, 6H).

(3aR,5S,6S,7R,7aR)-2-(dimethylamino)-5-((R)-2,2,2-trifluoro-1-methoxyethyl)-5,6,7,7a-tetrahydro-3aH-pyrano[3,2-d]thiazole-6,7-diol A solution of (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol (413 mg, 1.3 mmol) in DMF (30 mL) was treated with LiHMDS (1.6 mL, 1.6 mmol, 1M in THF) at 0° C. for 10 min, and followed by addition of CH$_3$I (278 mg, 1.9 mmol). After additional 1 hour at room temperature the reaction was quenched by saturated aqueous NH$_4$Cl solution (15 mL) and extracted with ethyl acetate (3×20 mL). The combined organic layer was dried over anhydrous magnesium sulfate and concentrated under vacuum. The residue was purified by flash column chromatography with 2%-10% methanol in dichloromethane to afford the title compound as a white solid (196 mg, 45%). (ES, m/z): [M+H]$^+$ 331.0; $^1$H NMR (300 MHz, D$_2$O): 6.21 (d, J=6.3 Hz, 1H), 4.11-4.06 (m, 2H), 3.93 (t, J=5.7 Hz, 1H), 3.83-3.71 (m, 2H), 3.60 (s, 3H), 2.91 (s, 6H).

Examples 3 & 4
(3aR,5S,6S,7R,7aR)-2-(methylamino)-5-((S)-2,2,2-trifluoro-1-phenoxyethyl)-5,6,7,7a-tetrahydro-3aH-pyrano[3,2-d]thiazole-6,7-diol & (3aR,5S,6S,7R,7aR)-2-(methylamino)-5-((R)-2,2,2-trifluoro-1-phenoxyethyl)-5,6,7,7a-tetrahydro-3aH-pyrano[3,2-d]thiazole-6,7-diol
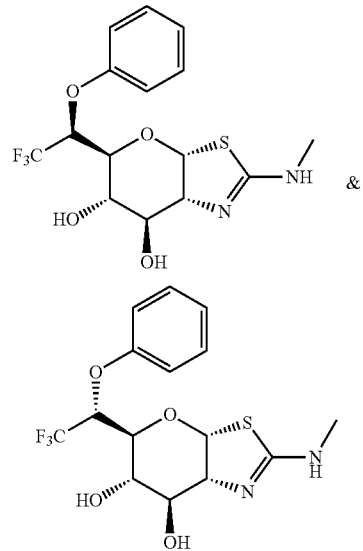
Scheme III
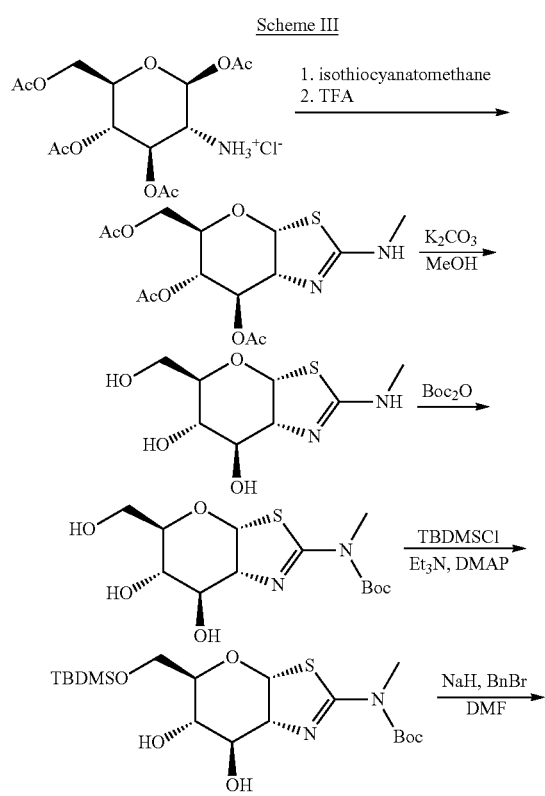
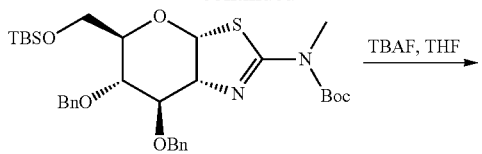
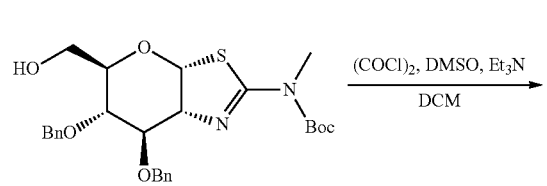
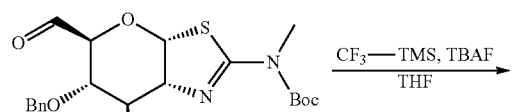
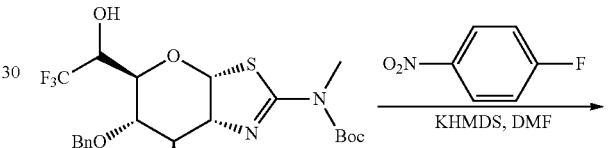
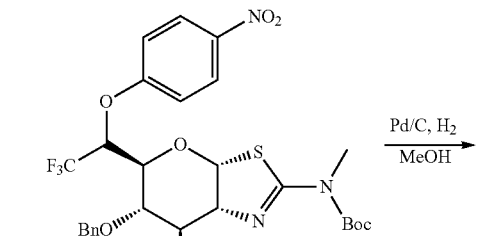
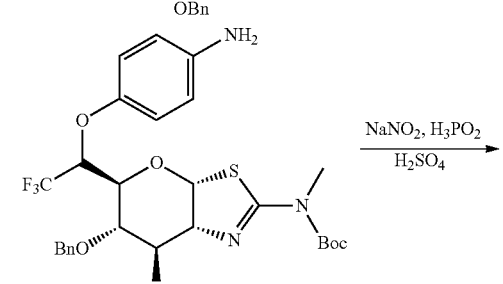
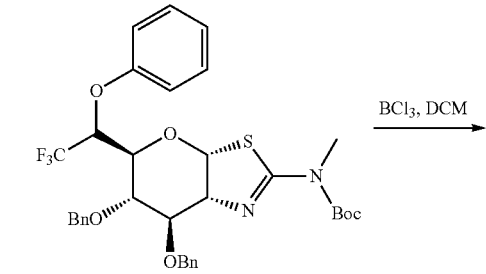

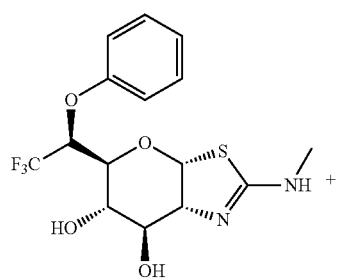

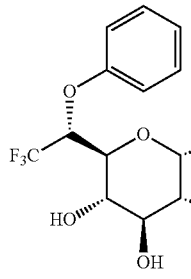

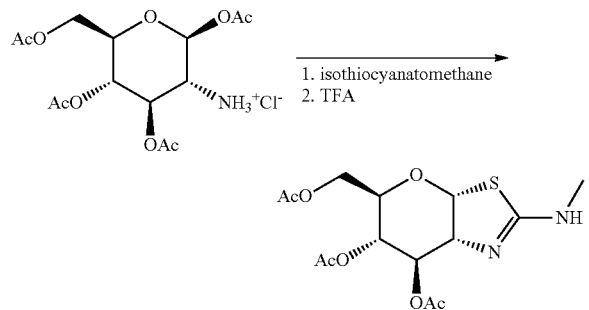

(3aR,5R,6S,7R,7aR)-5-(Acetoxymethyl)-2-(methyl-amino)-5,6,7,7a-tetrahydro-3aH-pyrano[3,2-d]thiazole-6,7-diyl diacetate To a solution of (3R,4R,5S,6R)-2,4,5-triacetoxy-6-(acetoxymethyl)-tetrahydro-2H-pyran-3-aminium chloride (100 g, 261 mmol) in CH₃CN (1 L) was added methyl isothiocyanate (21 g, 287 mmol), triethylamine (29 g, 287 mmol). After stirred for 12 h at 60° C., the resulting solution was treated with TFA (110 g, 0.96 mol) at room temperature overnight, and then washed with saturated sodium bicarbonate (1 L). The organic layer was dried over magnesium sulfate and concentrated under vacuum to provide a residue, which was purified by silica gel column, eluted with 1% MeOH in dichloromethane to give the title compound as a yellow oil (150 g, 87%). (ES, m/z): [M+H]⁺ 360.9; ¹H NMR (300 MHz, CDCl₃) δ 6.31-6.33 (d, J=6.6 Hz, 1H), 5.41-5.48 (t, J=8.4 Hz, 1H), 4.97-5.00 (m, 1H), 4.31-4.37 (t, J=5.7 Hz, 1H), 4.21 (m, 2H), 3.97 (m, 1H), 2.99 (s, 3H), 2.00-2.20 (m, 9H).

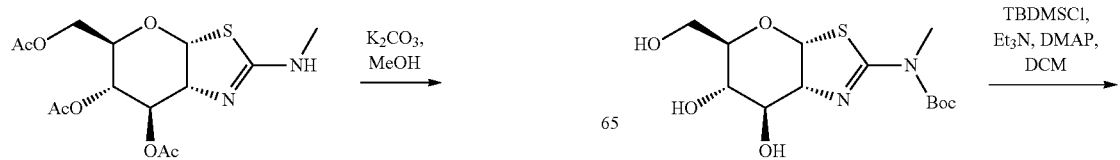

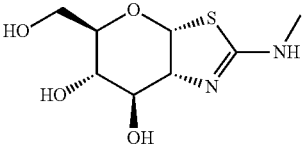

(3aR,5R,6S,7R,7aR)-5-(Hydroxymethyl)-2-(methyl-amino)-5,6,7,7a-tetrahydro-3aH-pyrano[3,2-d]thiazole-6,7-diol A solution of (3aR,5R,6S,7R,7aR)-5-(acetoxymethyl)-2-(methylamino)-5,6,7,7a-tetrahydro-3aH-pyrano[3,2-d]thiazole-6,7-diyl diacetate (150 g, 417 mmol) in methanol (1 L) was treated with potassium carbonate (11.5 g, 83 mmol). The resulting mixture was stirred overnight at room temperature to yield a solid. This was collected by filtration, washed with cold methanol and dried. The product was obtained as a yellow solid (85 g, 87%). (ES, m/z): [M+H]⁺ 235.1; 1H NMR (300 MHz, D₂O) δ 6.14-6.16 (d, J=6.3 Hz, 1H), 4.03-4.07 (m, 1H), 3.89-3.92 (m, 1H), 3.65-3.70 (m, 1H), 3.48-3.56 (m, 2H), 3.41-3.45 (m, 1H), 2.69 (s, 3H).

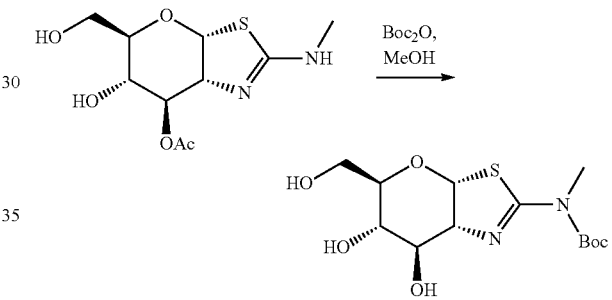

tert-Butyl (3aR,5R,6S,7R,7aR)-6,7-dihydroxy-5-(hydroxymethyl)-5,6,7,7a-tetrahydro-3aH-pyrano[3,2-d]thiazol-2-yl(methyl)carbamate A solution of (3aR,5R,6S,7R,7aR)-5-(hydroxymethyl)-2-(methylamino)-5,6,7,7a-tetrahydro-3aH-pyrano[3,2-d]thiazole-6,7-diol (85 g, 363 mmol) in methanol (600 mL) was treated with Boc₂O (117.7 g, 540 mmol) and triethylamine (73.3 g, 726 mmol). The resulting solution was stirred overnight at 45° C., and then concentrated under vacuum to give a residue, which was purified by silica gel column, eluted with 2.5% methanol in dichloromethane to give the title compound as a yellow solid (90 g, 74%). (ES, m/z): [M+H]⁺ 334.8; ¹H NMR (300 MHz, CDCl₃) δ 6.14-6.17 (d, J=6.9 Hz, 1H), 4.19-4.23 (t, J=6.3 Hz, 1H), 4.10-4.14 (t, J=5.4 Hz, 1H), 3.79-3.84 (m, 3H), 3.60-3.64 (m, 2H), 3.14 (s, 3H), 1.55 (s, 9H).

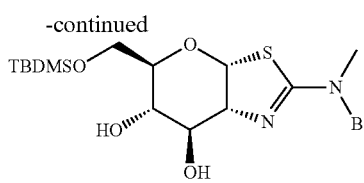

tert-Butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate To a mixture of tert-butyl (3aR,5R,6S,7R,7aR)-6,7-dihydroxy-5-(hydroxymethyl)-5,6,7,7a-tetrahydro-3aH-pyrano[3,2-d]thiazol-2-yl(methyl)carbamate (30 g, 90 mmol), DMAP (550 mg, 4.5 mmol) and triethylamine (18.2 g, 180 mmol) in dichloromethane (200 mL) was added tert-butylchlorodimethylsilane (16.3 g, 108 mmol) at 0° C. The resulting solution was stirred for 4 h at room temperature, and then concentrated under vacuum to provide a residue, which was purified by silica gel column, eluted with 1% methanol in dichloromethane to give the title compound as a white solid (20 g, 50%). (ES, m/z): [M+H]$^+$ 449.0; $^1$H NMR (300 MHz, CDCl$_3$) δ 6.10-6.12 (d, J=6.9 Hz, 1H), 4.15-4.24 (m, 2H), 3.83-3.97 (m, 5H), 3.60 (m, 1H), 2.58-2.66 (m, 2H), 1.55 (s, 9H), 1.18 (m, 3H), 0.91 (s, 9H), 0.09 (s, 6H).

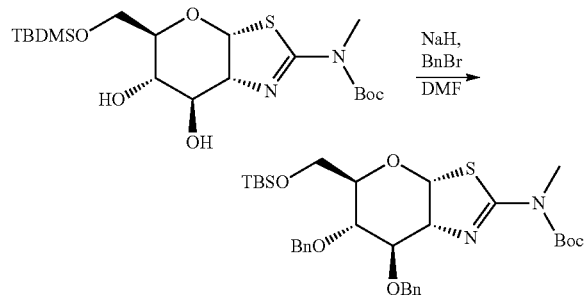

tert-butyl (3aR,5R,6S,7R,7aR)-6,7-bis(benzyloxy)-5-((tert-butyldimethylsilyloxy)methyl)-5,6,7,7a-tetrahydro-3aH-pyrano[3,2-d]thiazol-2-yl(methyl)carbamate A solution of tert-butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate (24 g, 56 mmol) in DMF (250 mL) was treated with NaH (5.8 g, 169 mmol, 70% dispersed by mineral oil) at 0° C. for 30 min, and followed by addition of (bromomethyl)benzene (28.6 g, 167 mmol). After additional 3 hours at 15° C., the reaction was quenched by ice-H$_2$O (400 mL), and extracted with ethyl acetate (3×200 mL). The combined organic layer was washed with brine (5×100 mL), dried over anhydrous sodium sulfate, and concentrated under reduced pressure. The residue was purified by a silica gel column, eluted with 5%-15% ethyl acetate in petroleum ether to afford tert-butyl (3aR,5R,6S,7R,7aR)-6,7-bis(benzyloxy)-5-((tert-butyldimethylsilyloxy)methyl)-5,6,7,7a-tetrahydro-3aH-pyrano[3,2-d]thiazol-2-yl(methyl)carbamate (22.6 g, 67%) as a yellow syrup. (ES, m/z) [M+H]$^+$ 629.0. $^1$H NMR (300 MHz, CDCl$_3$) δ 7.40-7.27 (m, 10H), 6.11 (d, J=6.6 Hz, 1H), 4.82-4.74 (m, 4H), 4.69-4.39 (m, 2H), 4.21 (t, J=4.3 Hz, 1H), 3.79-3.75 (m, 2H), 3.51-3.48 (m, 1H), 3.33 (s, 3H), 1.55 (s, 9H), 0.94 (s, 9H), 0.08 (s, 6H).

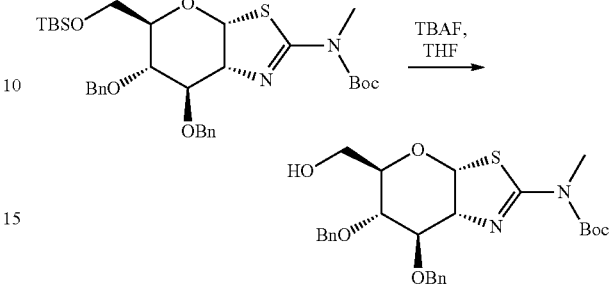

tert-butyl (3aR,5R,6S,7R,7aR)-6,7-bis(benzyloxy)-5-(hydroxymethyl)-5,6,7,7a-tetrahydro-3 aH-pyrano[3,2-d]thiazol-2-yl(methyl)carbamate A solution of tert-butyl (3aR,5R,6S,7R,7aR)-6,7-bis(benzyloxy)-5-((tert-butyldimethylsilyloxy)methyl)-5,6,7,7a-tetrahydro-3aH-pyrano[3,2-d]thiazol-2-yl(methyl)carbamate (22 g, 35 mmol) in THF (200 mL) was treated with TBAF (18.4 g, 70 mmol) at room temperature for 4 hours. The reaction was quenched by H$_2$O (500 mL), and extracted with ethyl acetate (3×200 mL). The combined organic layer was washed with brine (2×150 mL), dried over anhydrous sodium sulfate, and concentrated under reduced pressure. The residue was purified by a silica gel column, eluted with 10%-30% ethyl acetate in petroleum ether to afford tert-butyl (3aR,5R,6S,7R,7aR)-6,7-bis(benzyloxy)-5-(hydroxymethyl)-5,6,7,7a-tetrahydro-3aH-pyrano[3,2-d]thiazol-2-yl(methyl)carbamate (16.4 g, 91%) as a yellow syrup. (ES, m/z) [M+H]$^+$ 515.0. $^1$H NMR (300 MHz, CDCl$_3$) δ 7.42-7.29 (m, 10H), 6.09 (d, J=7.2 Hz, 1H), 4.78-4.69 (m, 3H), 4.66-4.60 (m, 1H), 4.58-4.43 (m, 2H), 3.74-3.50 (m, 4H), 3.33 (s, 3H), 1.54 (s, 9H).

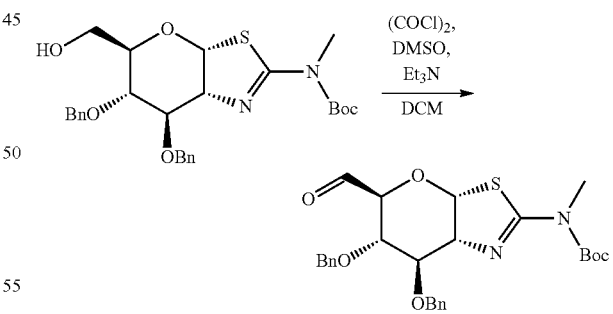

tert-butyl (3aR,5S,6S,7R,7aR)-6,7-bis(benzyloxy)-5-formyl-5,6,7,7a-tetrahydro-3aH-pyrano[3,2-d]thiazol-2-yl(methyl)carbamate A solution of DMSO (19.4 g, 248 mmol) in dichloromethane (200 mL) was treated with oxalyl dichloride (23.5 g, 187 mmol) at −78° C. for 1 hour under N$_2$ atmosphere, and followed by addition of a solution of tert-butyl (3aR,5R,6S,7R,7aR)-6,7-bis(benzyloxy)-5-(hydroxymethyl)-5,6,7,7a- tetrahydro-3aH-pyrano[3,2-d]thiazol-2-yl(methyl)carbamate (16 g, 31 mmol) in dichloromethane (50 mL). The resulted solution was stirred for 4 hours at −30° C., and followed by addition of triethylamine (37.7 g, 373 mmol) at −78° C. After stirred for 1 hour at −20° C., the reaction was quenched by water (200 mL), and extracted with dichloromethane (2×100 mL). The combined organic layer was washed with brine (2×150 mL), dried over anhydrous sodium sulfate, and concentrated under reduced pressure to afford crude tert-butyl (3aR,5S,6S,7R,7aR)-6,7-bis(benzyloxy)-5-formyl-5,6,7,7a-tetrahydro-3aH-pyrano[3,2-d]thiazol-2-yl(methyl)carbamate as a yellow syrup, used for the next step without further purification. (ES, m/z) [M+H]+ 513.0.

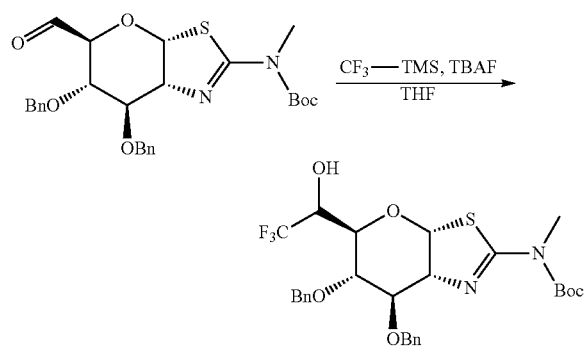

tert-butyl (3aR,5R,6S,7R,7aR)-6,7-bis(benzyloxy)-5-((R)-2,2,2-trifluoro-1-hydroxyethyl)-5,6,7,7a-tetrahydro-3aH-pyrano[3,2-d]thiazol-2-yl(methyl)carbamate A mixture of TBAF (3.2 g, 12 mmol) and 4 Å molecule sieves (3.2 g) in THF (50 mL) was stirred for 30 min at 0° C., and followed by addition of crude tert-butyl (3aR,5S,6S,7R,7aR)-6,7-bis(benzyloxy)-5-formyl-5,6,7,7a-tetrahydro-3aH-pyrano[3,2-d]thiazol-2-yl(methyl)carbamate and TMS-CF$_3$ (22.1 g, 155 mmol) in THF (100 mL). After 10 hours at room temperature, additional TBAF (16.3 g, 62 mmol) was added, and the mixture was stirred for 2 hours. After filtration, the filtrates were quenched by brine (100 mL), and extracted with ethyl acetate (3×200 mL). The combined organic layer was washed with brine (3×100 mL), dried over anhydrous sodium sulfate and concentrated under reduced pressure. The residue was purified by a silica gel column, eluted with 5%-20% ethyl acetate in petroleum ether to afford tert-butyl (3aR,5R,6S,7R,7aR)-6,7-bis(benzyloxy)-5-((R)-2,2,2-trifluoro-1-hydroxyethyl)-5,6,7,7a-tetrahydro-3aH-pyrano[3,2-d]thiazol-2-yl(methyl)carbamate (7.8 g, 43% for 2 steps, two isomers, the ratio was 4:6 determined by $^1$HNMR) as yellow oil. (ES, m/z): [M+H]+ 583.0. $^1$H NMR (300 MHz, CDCl$_3$) δ 7.44-7.30 (m, 10H), 6.12-6.08 (m, 1H), 4.76-4.72 (m, 3H), 4.61-4.49 (m, 2H), 4.35-4.21 (m, 2H), 3.95-3.81 (m, 1H), 3.95-3.81 (m, 1H), 3.32 (s, 3H), 1.55 (s, 9H)

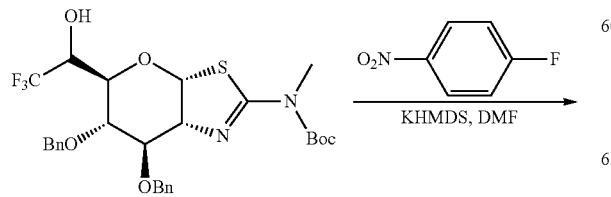

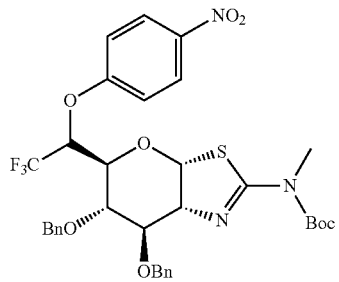

tert-butyl (3aR,5S,6S,7R,7aR)-6,7-bis(benzyloxy)-5-((R)-2,2,2-trifluoro-1-(4-nitrophenoxy)ethyl)-5,6,7,7a-tetrahydro-3aH-pyrano[3,2-d]thiazol-2-yl(methyl)carbamate To a solution of tert-butyl (3aR,5R,6S,7R,7aR)-6,7-bis(benzyloxy)-5-((R)-2,2,2-trifluoro-1-hydroxyethyl)-5,6,7,7a-tetrahydro-3aH-pyrano[3,2-d]thiazol-2-yl(methyl)carbamate (2.4 g, 4 mmol) in DMF (50 mL) was added LiHMDS (4.5 mL, 4.5 mmol, 1M in THF) at 0° C. under N$_2$ atmosphere with stirring. After 30 min at 15° C., 1-fluoro-4-nitrobenzene (635 mg, 4.5 mmol) was added and the reaction mixture was stirred for additional 2 hours at room temperature. The reaction was quenched by H$_2$O (50 mL) and extracted with ethyl acetate (3×30 mL). The combined organic layer was washed with brine (3×20 mL), dried over anhydrous magnesium sulfate and concentrated under vacuum. The residue was purified by a silica gel column, eluted with 3%-10% ethyl acetate in petroleum ether to afford the title compound (1.8 g, 62%, two isomers, the ratio was 4:6 determined by $^1$HNMR) as a white syrup. (ES, m/z): [M+H]+ 704.1. $^1$H NMR (300 MHz, CDCl$_3$) δ 8.13-8.05 (m, 2H), 7.37-7.30 (m, 10H), 7.20-7.04 (m, 2H), 6.56-6.13 (dd, J$_1$=7.2 Hz, J$_2$=7.5 Hz, 1H), 5.21-5.13 (m, 1H), 4.83-4.73 (m, 3H), 4.61-4.21 (m, 3H), 4.11-3.87 (m, 2H), 3.31 (d, J=2.7 Hz, 3H), 1.56-1.53 (m, 9H).

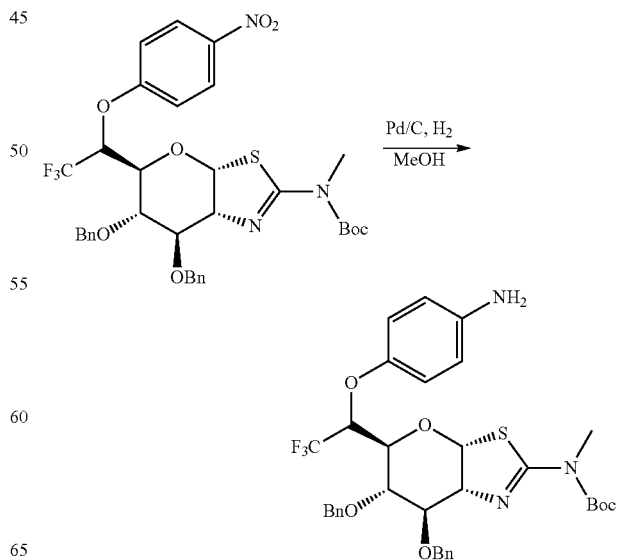

tert-butyl (3aR,5S,6S,7R,7aR)-5-((R)-1-(4-amino-phenoxy)-2,2,2-trifluoroethyl)-6,7-bis(benzyloxy)-5,6,7,7a-tetrahydro-3aH-pyrano[3,2-d]thiazol-2-yl(methyl)carbamate A mixture of tert-butyl (3aR,5S,6S,7R,7aR)-6,7-bis(benzyloxy)-5-((R)-2,2,2-trifluoro-1-(4-nitrophenoxy)ethyl)-5,6,7,7a-tetrahydro-3aH-pyrano[3,2-d]thiazol-2-yl(methyl)carbamate (900 mg, 1.3 mmol) and Pd/C (10%, 90 mg) in methanol (40 mL) was stirred for 4 hours at room temperature under hydrogen atmosphere (1 atm). The solids were filtered out and the solvent was removed under vacuum to give a residue, which was purified by a silica gel column, eluted with 3%-25% ethyl acetate in petroleum ether to afford the product (620 mg, 72%, two isomers, the ratio=4:6, determined by $^1$HNMR) as a white syrup. (ES, m/z): [M+H]$^+$ 673.9. $^1$H NMR (300 MHz, CDCl$_3$) δ 7.44-7.27 (m, 12H), 7.19-7.03 (m, 2H), 6.36-6.17 (dd, J$_1$=6.9 Hz, J$_2$=6.9 Hz, 1H), 4.99-4.92 (m, 1H), 4.86-4.71 (m, 4H), 4.60-4.19 (m, 2H), 4.11-4.00 (m, 1H), 3.77-3.76 (m, 1H), 3.31 (d, J=3.3 Hz, 3H), 1.57-1.54 (m, 9H).

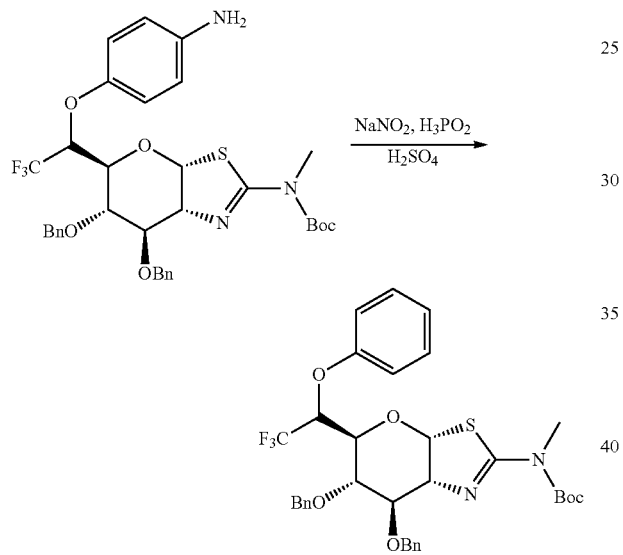

tert-butyl (3aR,5S,6S,7R,7aR)-6,7-bis(benzyloxy)-5-((R)-2,2,2-trifluoro-1-phenoxyethyl)-5,6,7,7a-tetrahydro-3aH-pyrano[3,2-d]thiazol-2-yl(methyl)carbamate To a solution of tert-butyl (3aR,5S,6S,7R,7aR)-5-((R)-1-(4-aminophenoxy)-2,2,2-trifluoroethyl)-6,7-bis(benzyloxy)-5,6,7,7a-tetrahydro-3aH-pyrano[3,2-d]thiazol-2-yl(methyl)carbamate (520 mg, 0.78 mmol) in conc. sulfuric acid (3 mL) and H$_2$O (9 mL) was added a solution of NaNO$_2$ (59 mg, 0.86 mmol) in H$_2$O (2 mL) at 0° C. After 15 min, H$_3$PO$_2$ (515 mg, 7.8 mmol) and Cu$_2$O (14 mg, 0.1 mmol) were added to the reaction mixture. After additional 1 hour at 5° C., the reaction was quenched by the saturated aqueous Na$_2$CO$_3$ (35 mL), and extracted with ethyl acetate (3×40 mL). The combined organic layer was washed with brine (3×20 mL), dried over anhydrous magnesium sulfate and concentrated under vacuum. The residue was purified by a silica gel column, eluted with 2%-20% ethyl acetate in petroleum ether to afford the product (238 mg, 47%, two isomers, the ratio was 4:6 determined by $^1$HNMR) as a white syrup. (ES, m/z): [M+H]$^+$ 659.0. $^1$H NMR (300 MHz, CDCl$_3$) δ 7.41-7.29 (m, 12H), 7.17-7.05 (m, 2H), 7.04-7.00 (m, 1H), 6.37-6.22 (dd, J$_1$=6.3 Hz, J$_2$=6.3 Hz, 1H), 5.09-5.02 (m, 1H), 4.83-4.72 (m, 3H), 4.66-4.21 (m, 2H), 4.11-4.00 (m, 2H), 3.77-3.76 (m, 1H), 3.31 (d, J=3.3 Hz, 3H), 1.57-1.54 (m, 9H).

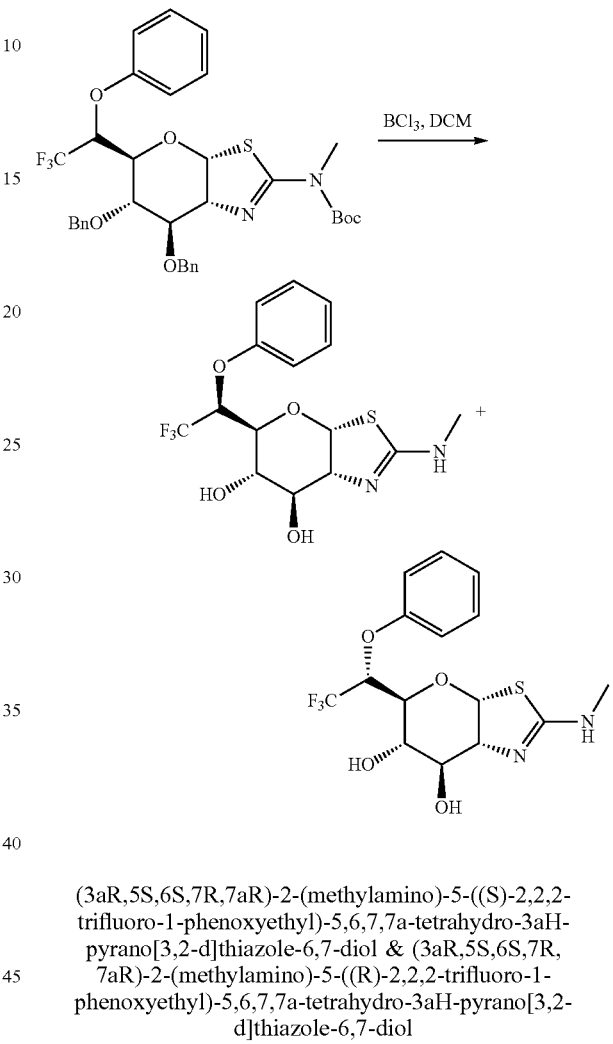

(3aR,5S,6S,7R,7aR)-2-(methylamino)-5-((S)-2,2,2-trifluoro-1-phenoxyethyl)-5,6,7,7a-tetrahydro-3aH-pyrano[3,2-d]thiazole-6,7-diol & (3aR,5S,6S,7R,7aR)-2-(methylamino)-5-((R)-2,2,2-trifluoro-1-phenoxyethyl)-5,6,7,7a-tetrahydro-3aH-pyrano[3,2-d]thiazole-6,7-diol A solution of tert-butyl (3aR,5S,6S,7R,7aR)-6,7-bis(benzyloxy)-5-((R)-2,2,2-trifluoro-1-phenoxyethyl)-5,6,7,7a-tetrahydro-3aH-pyrano[3,2-d]thiazol-2-yl(methyl)carbamate (230 mg, 0.35 mmol) in dichloromethane (20 mL) was treated with BCl$_3$ (3.5 mL, 3.5 mmol, 1 M in dichloromethane) for 2 hours at −78° C. The reaction was quenched by methanol (20 mL). Removal of volatiles gave a residue, which was dissolved into methanol (5 mL) and neutralized with concentrated NH$_4$OH (2 mL). After concentrated under reduced pressure, the crude product was purified by a silica gel column, eluted with 5%-20% methanol in dichloromethane to give a mixture of the above two compounds. Separation by Prep-HPLC with the following conditions (Column, Sun fire prep. C18; mobile phase, water with 0.03% NH$_4$OH and CH$_3$CN (10% up to 45% in 10 min); Detector, UV 220 nm) gave (3aR,5S,6S,7R,7aR)-2-(methylamino)-5-((S)-2,2,2-trifluoro-1-phenoxyethyl)-5,6,7,7a-tetrahydro-3aH-pyrano[3,2-d]thiazole-6,7-diol as a white solid (32 mg, 24%, Faster eluting isomer by HPLC). (ES, m/z) [M+H]$^+$ 379.0. $^1$H NMR (300 MHz, CD$_3$OD) δ 7.31-7.21 (m, 2H), 7.08-6.99 (m, 3H); 6.29 (d, J=7.2 Hz, 1H), 5.01-4.93 (m, 1H), 4.15 (t, J=5.7 Hz, 1H), 4.03-3.83 (m, 2H), 3.87-3.83 (m, 1H), 2.79 (s, 3H); and (3aR,5S,6S,7R,7aR)-2-(methylamino)-5-((R)-2,2,2-trifluoro-1-phenoxyethyl)-5,6,7,7a-tetrahydro-3aH-pyrano[3,2-d]thiazole-6,7-diol as a white solid (45 mg, 34%, Slower eluting isomer by HPLC); (ES, m/z) [M+H]$^+$ 379.0. $^1$H NMR (300 MHz, CD$_3$OD) δ 7.36-7.31 (m, 2H), 7.16-7.14 (m, 3H); 6.36 (d, J=6.3 Hz, 1H), 5.13-5.10 (m, 1H), 4.11 (t, J=5.7 Hz, 1H), 4.03-3.96 (m, 2H), 3.77-3.72 (m, 1H), 2.87 (s, 3H).

Example 5

(3aR,5S,6S,7R,7aR)-2-(methylamino)-5-((R)-2,2,2-trifluoro-1-methoxyethyl)-5,6,7,7a-tetrahydro-3aH-pyrano[3,2-d]thiazole-6,7-diol

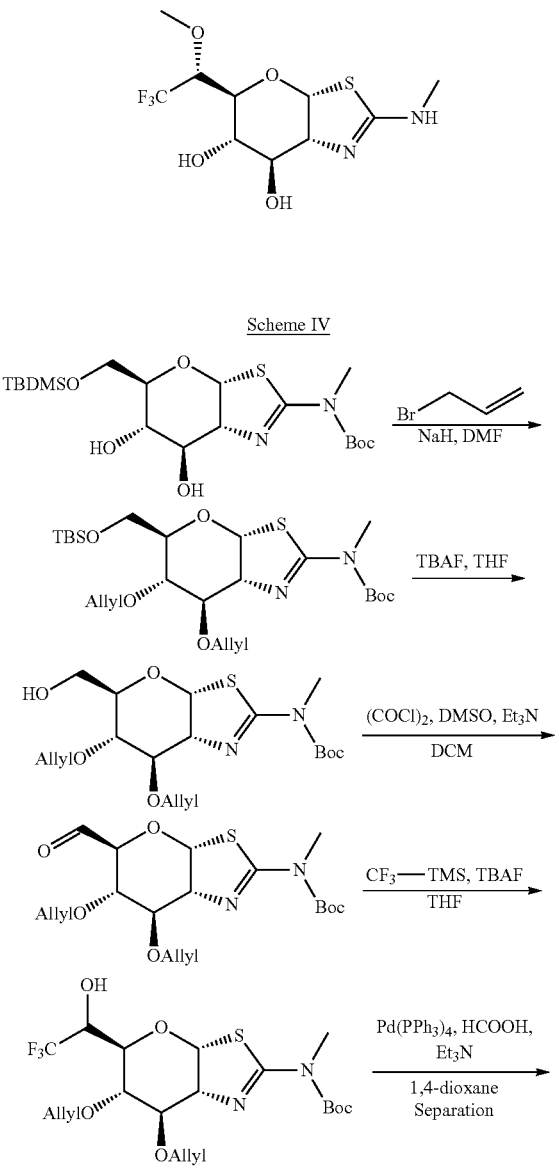

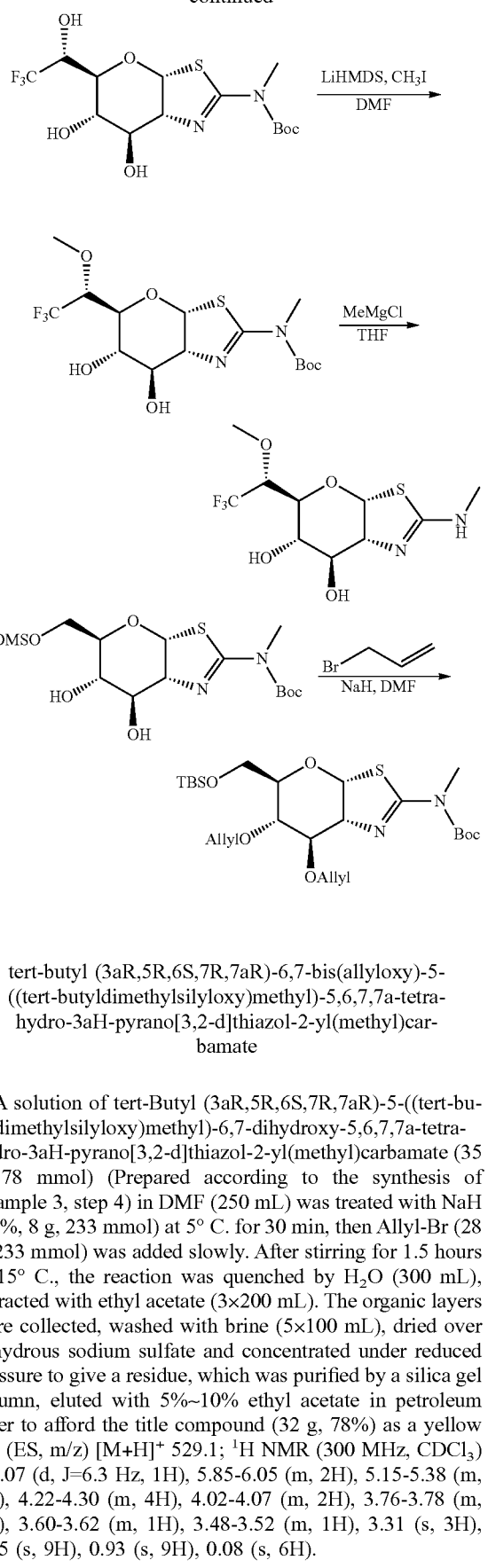

tert-butyl (3aR,5R,6S,7R,7aR)-6,7-bis(allyloxy)-5-((tert-butyldimethylsilyloxy)methyl)-5,6,7,7a-tetrahydro-3aH-pyrano[3,2-d]thiazol-2-yl(methyl)carbamate A solution of tert-Butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate (35 g, 78 mmol) (Prepared according to the synthesis of Example 3, step 4) in DMF (250 mL) was treated with NaH (70%, 8 g, 233 mmol) at 5° C. for 30 min, then Allyl-Br (28 g, 233 mmol) was added slowly. After stirring for 1.5 hours at 15° C., the reaction was quenched by H$_2$O (300 mL), extracted with ethyl acetate (3×200 mL). The organic layers were collected, washed with brine (5×100 mL), dried over anhydrous sodium sulfate and concentrated under reduced pressure to give a residue, which was purified by a silica gel column, eluted with 5%~10% ethyl acetate in petroleum ether to afford the title compound (32 g, 78%) as a yellow oil; (ES, m/z) [M+H]$^+$ 529.1; $^1$H NMR (300 MHz, CDCl$_3$) δ 6.07 (d, J=6.3 Hz, 1H), 5.85-6.05 (m, 2H), 5.15-5.38 (m, 4H), 4.22-4.30 (m, 4H), 4.02-4.07 (m, 2H), 3.76-3.78 (m, 2H), 3.60-3.62 (m, 1H), 3.48-3.52 (m, 1H), 3.31 (s, 3H), 1.55 (s, 9H), 0.93 (s, 9H), 0.08 (s, 6H).

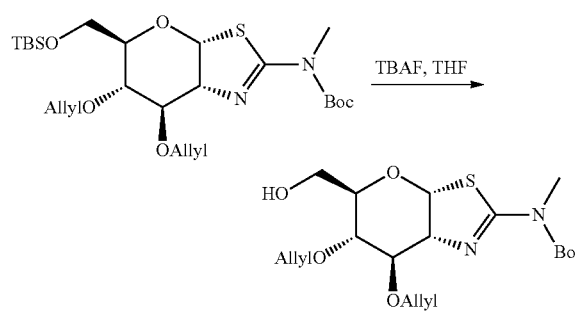

tert-butyl (3aR,5R,6S,7R,7aR)-6,7-bis(allyloxy)-5-(hydroxymethyl)-5,6,7,7a-tetrahydro-3aH-pyrano[3,2-d]thiazol-2-yl(methyl)carbamate A solution of tert-butyl (3aR,5R,6S,7R,7aR)-6,7-bis(allyloxy)-5-((tert-butyldimethylsilyloxy)methyl)-5,6,7,7a-tetrahydro-3aH-pyrano[3,2-d]thiazol-2-yl(methyl)carbamate (104 g, 197 mmol) in THF (700 mL) was treated with TBAF (77 g, 296 mmol) at 20° C. for 6 hours, then the reaction was quenched by water (500 mL), extracted with ethyl acetate (5×300 mL). The organic layers combined, washed with brine (2×150 mL), dried over anhydrous sodium sulfate and concentrated under reduced pressure to give a residue, which was purified by a silica gel column, eluted with 5%~30% ethyl acetate in petroleum ether to afford the title compound (72 g, 88%) as a yellow oil; (ES, m/z) [M+H]$^+$ 415.0; $^1$H NMR (300 MHz, CDCl$_3$) δ 6.07 (d, J=6.9 Hz, 1H), 5.94-6.01 (m, 2H), 5.17-5.38 (m, 4H), 4.02-4.45 (m, 6H), 3.74-3.85 (m, 1H), 3.51-3.71 (m, 2H), 3.55-3.68 (m, 1H), 3.33 (s, 3H), 1.55 (s, 9H).

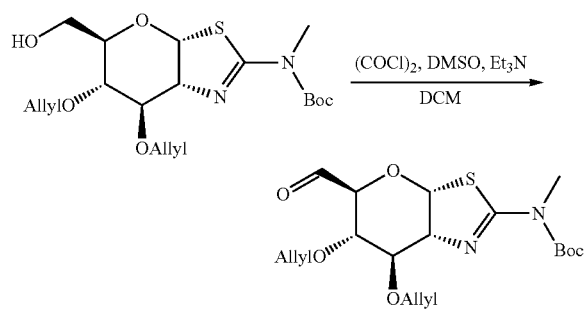

tert-butyl (3aR,5S,6S,7R,7aR)-6,7-bis(allyloxy)-5-formyl-5,6,7,7a-tetrahydro-3aH-pyrano[3,2-d]thiazol-2-yl(methyl)carbamate To a solution of DMSO (45 g, 580 mmol) in dichloromethane (200 mL) was added oxalyl dichloride (55 g, 435 mmol) at −78° C. under N$_2$ atmosphere with stirring. After 1 hour at −30° C., a solution of tert-butyl (3aR,5R,6S,7R,7aR)-6,7-bis(allyloxy)-5-(hydroxymethyl)-5,6,7,7a-tetrahydro-3aH-pyrano[3,2-d]thiazol-2-yl(methyl)carbamate (30 g, 72 mmol) in dichloromethane (50 mL) was added slowly. The resulted solution was stirred for 4 hours at −30° C., and followed by addition of triethylamine (73 g, 725 mmol) at −78° C. After stirring for additional 1 hour at −20° C., the reaction was quenched by water (300 mL) and extracted with dichloromethane (3×100 mL). The combined organic layer was washed with brine (2×150 mL), dried over anhydrous sodium sulfate and concentrated under reduced pressure to afford crude tert-butyl (3aR,5S,6S,7R,7aR)-6,7-bis(allyloxy)-5-formyl-5,6,7,7a-tetrahydro-3aH-pyrano[3,2-d]thiazol-2-yl(methyl)carbamate as yellow syrup, which was used for the next step without further purification. (ES, m/z) [M+H]$^+$ 413.0.

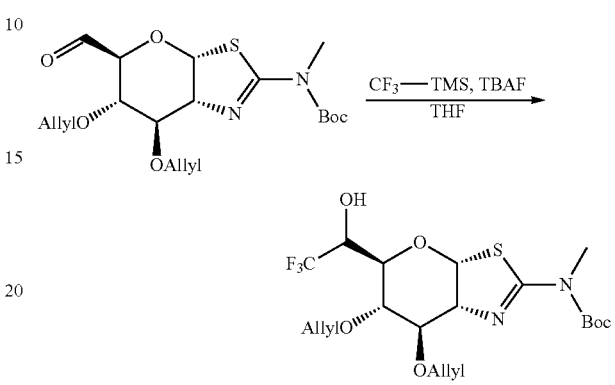

tert-butyl (3aR,5R,6S,7R,7aR)-6,7-bis(allyloxy)-5-((R)-2,2,2-trifluoro-1-hydroxyethyl)-5,6,7,7a-tetrahydro-3aH-pyrano[3,2-d]thiazol-2-yl(methyl)carbamate A mixture of TBAF (5.7 g, 22 mmol) and 4 Å molecule sieves (5.7 g) in THF (50 mL) was stirred for 30 min at 0° C., and followed by addition of a solution of crude tert-butyl (3aR,5S,6S,7R,7aR)-6,7-bis(allyloxy)-5-formyl-5,6,7,7a-tetrahydro-3aH-pyrano[3,2-d]thiazol-2-yl(methyl)carbamate and TMS-CF$_3$ (51 g, 359 mmol) in THF (50 mL). After stirring for 12 hours at room temperature, additional TBAF (37 g, 141 mmol) was added. The mixture was stirred for 2 hours. After filtration, the filtrates were quenched by brine (100 mL), extracted with ethyl acetate (3×100 mL). The combined organic layer was washed with brine (3×50 mL), dried over anhydrous sodium sulfate and concentrated under reduced pressure. The residue was purified by a silica gel column, eluted with 5%-25% ethyl acetate in petroleum ether to afford tert-butyl (3aR,5R,6S,7R,7aR)-6,7-bis(allyloxy)-5-((R)-2,2,2-trifluoro-1-hydroxyethyl)-5,6,7,7a-tetrahydro-3aH-pyrano[3,2-d]thiazol-2-yl(methyl)carbamate (16.8 g, 48% for 2 steps, two isomers, the ratio was 4:6 determined by $^1$HNMR) as yellow oil. (ES, m/z): [M+H]$^+$ 483.0. $^1$H NMR (300 MHz, CDCl$_3$) δ 6.18-6.12 (m, 1H), 5.99-5.87 (m, 2H), 5.37-5.19 (m, 4H), 4.43-4.01 (m, 5H), 3.95-3.91 (m, 2H), 3.62-3.57 (m, 2H), 3.25-3.24 (m, 3H), 1.54-1.53 (m, 9H).

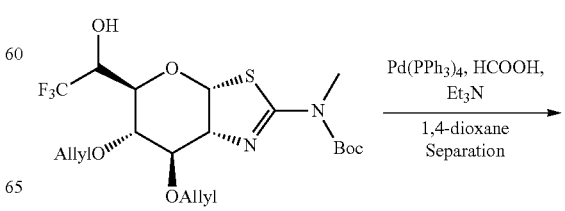

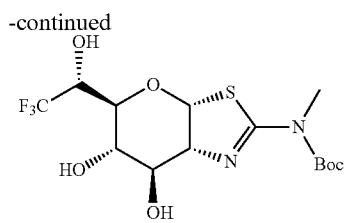

tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(methyl)carbamate To a solution of tert-butyl (3aR,5R,6S,7R,7aR)-6,7-bis(allyloxy)-5-((R)-2,2,2-trifluoro-1-hydroxyethyl)-5,6,7,7a-tetrahydro-3aH-pyrano[3,2-d]thiazol-2-yl(methyl)carbamate (16 g, 33 mmol) in 1,4-dioxane (250 mL) was added Pd(PPh₃)₄ (7.6 g, 6.6 mmol), Et₃N (26.6 g, 264 mmol) and HCOOH (9.2 g, 198 mmol) at room temperature under N₂ atmosphere. After stirring for 12 hours at 60° C., the reaction was quenched by H₂O (150 mL), extracted with ethyl acetate (3×200 mL). The combined organic layer was washed with brine (2×150 mL), dried over anhydrous sodium sulfate and concentrated under reduced pressure. The residue was purified by a silica gel column, eluted with 1%-10% methanol in dichloromethane to afford tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(methyl)carbamate (5.2 g, 39%) as a light yellow solid. (ES, m/z): [M+H]⁺ 403.0. ¹HNMR (300 MHz, CDCl₃) δ 6.25 (d, J=6.3 Hz, 1H), 4.31-4.25 (m, 1H), 4.14-4.10 (m, 1H), 4.00-3.97 (m, 1H), 3.78-3.74 (m, 2H), 3.24 (s, 3H), 1.54 (s, 9H).

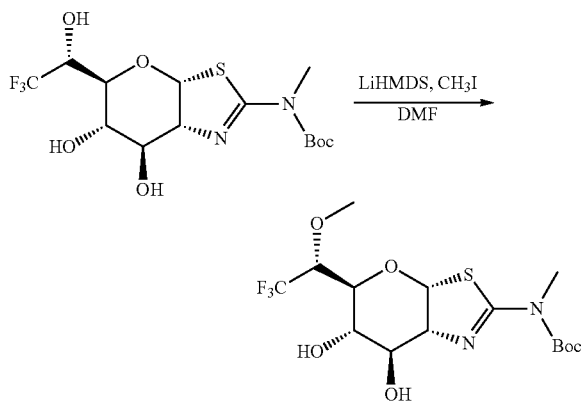

tert-butyl (3aR,5S,6S,7R,7aR)-6,7-dihydroxy-5-((R)-2,2,2-trifluoro-1-methoxyethyl)-5,6,7,7a-tetrahydro-3aH-pyrano[3,2-d]thiazol-2-yl(methyl)carbamate To a solution of tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(methyl)carbamate (150 mg, 0.37 mmol) in DMF (10 mL) was added LiHMDS (0.45 mL, 0.45 mmol, 1M in THF) at 0° C. under N₂ atmosphere with stirring. After 30 min at 10° C., CH₃I (79 mg, 0.56 mmol) was added and the reaction mixture was stirred for additional 1 hour at room temperature. The reaction was quenched by saturated aqueous NH₄Cl solution (15 mL), extracted with ethyl acetate (3×20 mL). The combined organic layer was dried over anhydrous magnesium sulfate and concentrated under vacuum. The residue was purified by flash column chromatography with 1%-8% methanol in dichloromethane to afford tert-butyl (3aR,5S,6S,7R,7aR)-6,7-dihydroxy-5-((R)-2,2,2-trifluoro-1-methoxyethyl)-5,6,7,7a-tetrahydro-3aH-pyrano[3,2-d]thiazol-2-yl(methyl)carbamate as a white solid (87 mg, 56%). (ES, m/z): [M+H]⁺ 417.0. ¹H NMR (300 MHz, CDCl₃) δ 6.26 (d, J=6.3 Hz, 1H), 4.18-4.15 (m, 2H), 4.03 (t, J=4.8 Hz, 1H), 3.86-3.83 (m, 2H), 3.67 (s, 3H), 3.23 (s, 3H), 1.53 (s, 9H).

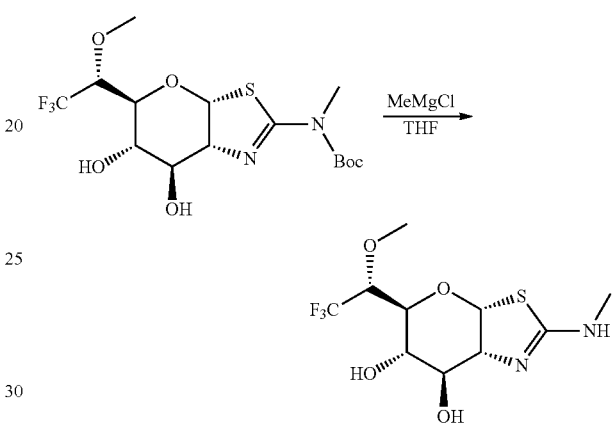

(3aR,5S,6S,7R,7aR)-2-(methylamino)-5-((R)-2,2,2-trifluoro-1-methoxyethyl)-5,6,7,7a-tetrahydro-3aH-pyrano[3,2-d]thiazole-6,7-diol A solution of tert-butyl (3aR,5S,6S,7R,7aR)-6,7-dihydroxy-5-((R)-2,2,2-trifluoro-1-methoxyethyl)-5,6,7,7a-tetrahydro-3aH-pyrano[3,2-d]thiazol-2-yl(methyl)carbamate (87 mg, 0.21 mmol) in THF (15 mL) was treated with MeMgCl (1.1 mL, 3.3 mmol, 3M in THF) at room temperature for 1 hour. The reaction was quenched by saturated aqueous NH₄Cl (2 mL) solution. Removal of volatiles gave a residue, which was purified by flash column chromatography with 4%-10% methanol in dichloromethane to afford the title compound as a white solid. (42 mg, 64%) (ES, m/z): [M+H]⁺ 317.0. ¹H NMR (300 MHz, D₂O) δ 6.25 (d, J=6.3 Hz, 1H), 4.16-4.12 (m, 2H), 4.00 (t, J=4.8 Hz, 1H), 3.82-3.80 (m, 2H), 3.63 (s, 3H), 2.79 (s, 3H).

Example 6

(3aR,5S,6S,7R,7aR)-2-(ethylamino)-5-((R)-2,2,2-trifluoro-1-methoxyethyl)-5,6,7,7a-tetrahydro-3aH-pyrano[3,2-d]thiazole-6,7-diol

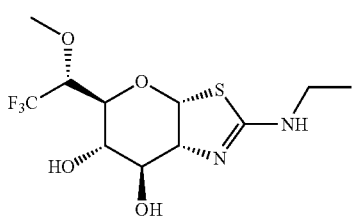 [SMILES: CCNC1=N[C@@H]2[C@@H](O)[C@H](O)[C@@H]([C@@H](OC)C(F)(F)F)O[C@@H]2S1]

Scheme V

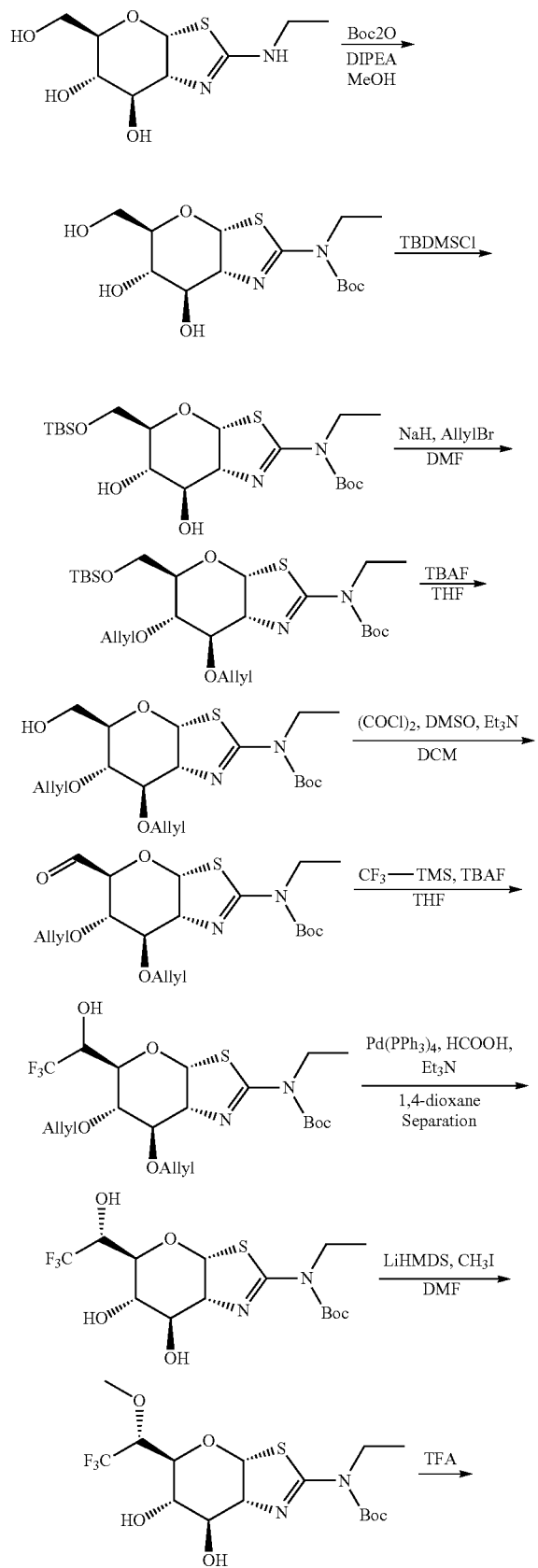

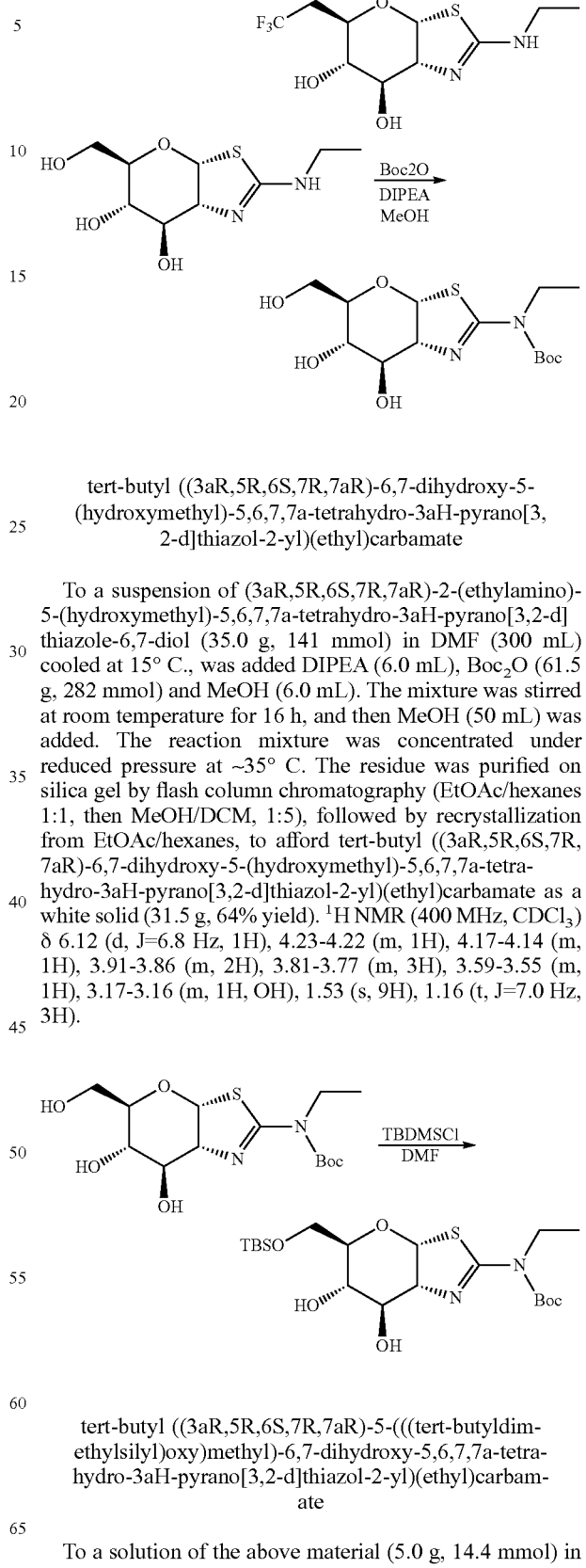

tert-butyl ((3aR,5R,6S,7R,7aR)-6,7-dihydroxy-5-(hydroxymethyl)-5,6,7,7a-tetrahydro-3aH-pyrano[3,2-d]thiazol-2-yl)(ethyl)carbamate To a suspension of (3aR,5R,6S,7R,7aR)-2-(ethylamino)-5-(hydroxymethyl)-5,6,7,7a-tetrahydro-3aH-pyrano[3,2-d]thiazole-6,7-diol (35.0 g, 141 mmol) in DMF (300 mL) cooled at 15° C., was added DIPEA (6.0 mL), Boc$_2$O (61.5 g, 282 mmol) and MeOH (6.0 mL). The mixture was stirred at room temperature for 16 h, and then MeOH (50 mL) was added. The reaction mixture was concentrated under reduced pressure at ~35° C. The residue was purified on silica gel by flash column chromatography (EtOAc/hexanes 1:1, then MeOH/DCM, 1:5), followed by recrystallization from EtOAc/hexanes, to afford tert-butyl ((3aR,5R,6S,7R,7aR)-6,7-dihydroxy-5-(hydroxymethyl)-5,6,7,7a-tetrahydro-3aH-pyrano[3,2-d]thiazol-2-yl)(ethyl)carbamate as a white solid (31.5 g, 64% yield). $^1$H NMR (400 MHz, CDCl$_3$) δ 6.12 (d, J=6.8 Hz, 1H), 4.23-4.22 (m, 1H), 4.17-4.14 (m, 1H), 3.91-3.86 (m, 2H), 3.81-3.77 (m, 3H), 3.59-3.55 (m, 1H), 3.17-3.16 (m, 1H, OH), 1.53 (s, 9H), 1.16 (t, J=7.0 Hz, 3H).

tert-butyl ((3aR,5R,6S,7R,7aR)-5-(((tert-butyldimethylsilyl)oxy)methyl)-6,7-dihydroxy-5,6,7,7a-tetrahydro-3aH-pyrano[3,2-d]thiazol-2-yl)(ethyl)carbamate To a solution of the above material (5.0 g, 14.4 mmol) in DMF (25 mL) was added imidazole (1.57 g, 23.1 mmol) and TBDMSCl (2.82 g, 18.7 mmol). The reaction mixture stirred at room temperature for 30 h was diluted with EtOAc (100 mL). Organics were washed with satd. NH$_4$Cl, brine, dried over anhydrous Na$_2$SO$_4$ and concentrated. The residue was purified on silica gel by flash column chromatography (EtOAc/hexanes, 1:1), affording tert-butyl ((3aR,5R,6S,7R,7aR)-5-(((tert-butyldimethylsilyl)oxy)methyl)-6,7-dihydroxy-5,6,7,7a-tetrahydro-3aH-pyrano[3,2-d]thiazol-2-yl)(ethyl)carbamate as a white solid (5.08 g, 76%). $^1$H NMR (400 MHz, CDCl$_3$) δ 6.12 (d, J=6.7 Hz, 1H), 4.25 (t, J=6.2 Hz, 1H), 4.16 (t, J=6.4 Hz, 1H), 4.10-4.04 (m, 2H), 3.91-3.85 (m, 3H), 3.65-3.62 (m, 1H), 1.55 (s, 9H), 1.26 (t, J=7.0 Hz, 3H), 0.89 (s, 9H), 0.08 (s, 6H).

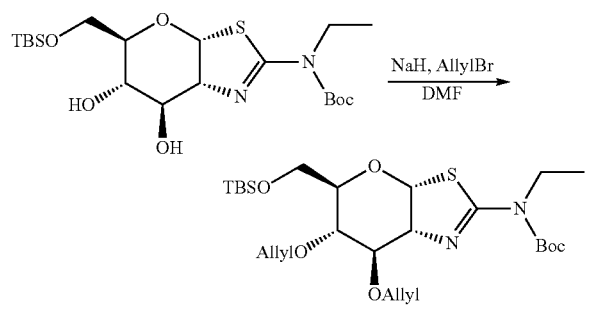

tert-butyl (3aR,5R,6S,7R,7aR)-6,7-bis(allyloxy)-5-((tert-butyldimethylsilyloxy)methyl)-5,6,7,7a-tetrahydro-3aH-pyrano[3,2-d]thiazol-2-yl(ethyl)carbamate A solution of tert-butyl (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(ethyl)carbamate (24 g, 52 mmol) in DMF (250 mL) was treated with NaH (5.3 g, 156 mmol, 70% dispersed by mineral oil) at 0° C. for 30 min, and followed by addition of 3-bromoprop-1-ene (18.7 g, 156 mmol). After additional 2 hours at 15° C., the reaction was quenched by ice-H$_2$O (400 mL), and extracted with ethyl acetate (3×200 mL). The combined organic layer was washed with brine (5×100 mL), dried over anhydrous sodium sulfate, and concentrated under reduced pressure. The residue was purified by a silica gel column, eluted with 5%-15% ethyl acetate in petroleum ether to afford the product (22.6 g, 80%) as a yellow syrup. (ES, m/z) [M+H]$^+$ 543.0. $^1$H NMR (300 MHz, CDCl$_3$) δ 6.07 (d, J=6.3 Hz, 1H), 6.07-5.87 (m, 2H), 5.40-5.17 (m, 4H), 4.31-4.22 (m, 4H), 4.08-4.02 (m, 2H), 3.78-3.76 (m, 4H), 3.62-3.60 (m, 1H), 3.53-3.49 (m, 1H), 1.56 (s, 9H), 1.20 (t, J=6.9 Hz, 3H), 0.94 (s, 9H), 0.08 (s, 6H).

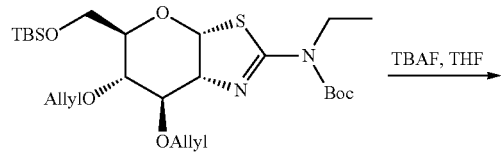

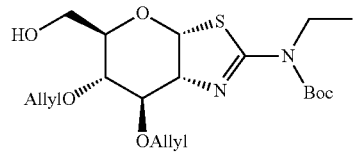

tert-butyl (3aR,5R,6S,7R,7aR)-6,7-bis(allyloxy)-5-(hydroxymethyl)-5,6,7,7a-tetrahydro-3aH-pyrano[3,2-d]thiazol-2-yl(ethyl)carbamate A solution of tert-butyl (3aR,5R,6S,7R,7aR)-6,7-bis(allyloxy)-5-((tert-butyldimethylsilyloxy)methyl)-5,6,7,7a-tetrahydro-3aH-pyrano[3,2-d]thiazol-2-yl(ethyl)carbamate (22 g, 41 mmol) in THF (200 mL) was treated with TBAF (21.2 g, 81 mmol) at room temperature for 4 hours. The reaction was quenched by H$_2$O (500 mL), and extracted with ethyl acetate (3×200 mL). The combined organic layer was washed with brine (2×150 mL), dried over anhydrous sodium sulfate, and concentrated under reduced pressure. The residue was purified by a silica gel column, eluted with 10%-30% ethyl acetate in petroleum ether to afford the product (15.6 g, 90%) as a yellow syrup. (ES, m/z) [M+H]$^+$ 429.0. $^1$H NMR (300 MHz, CDCl$_3$) δ 6.07 (d, J=6.3 Hz, 1H), 6.02-5.93 (m, 2H), 5.39-5.18 (m, 4H), 4.46-4.04 (m, 6H), 3.86-3.70 (m, 3H), 3.70-3.50 (m, 2H), 3.68-3.55 (m, 1H), 1.56 (s, 9H), 1.21 (t, J=6.9 Hz, 3H).

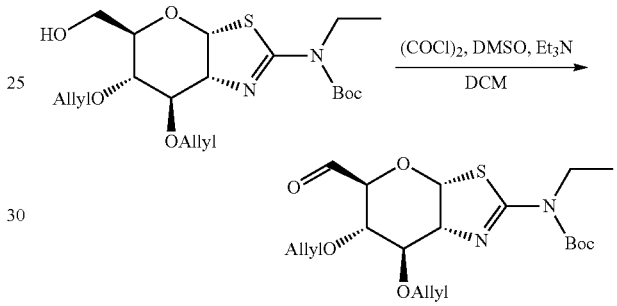

tert-butyl (3aR,5S,6S,7R,7aR)-6,7-bis(allyloxy)-5-formyl-5,6,7,7a-tetrahydro-3aH-pyrano[3,2-d]thiazol-2-yl(ethyl)carbamate To a solution of DMSO (21.8 g, 280 mmol) in dichloromethane (150 mL) was added oxalyl dichloride (26.5 g, 210 mmol) at −78° C. under N$_2$ atmosphere with stirring. After 1 hour at −30° C., a solution of tert-butyl (3aR,5R,6S,7R,7aR)-6,7-bis(allyloxy)-5-(hydroxymethyl)-5,6,7,7a-tetrahydro-3aH-pyrano[3,2-d]thiazol-2-yl(ethyl)carbamate (15 g, 35 mmol) in dichloromethane (40 mL) was added slowly. The resulted solution was stirred for 4 hours at −30° C., and followed by addition of triethylamine (35.4 g, 350 mmol) at −78° C. After stirring for additional 1 hour at −20° C., the reaction was quenched by water (300 mL) and extracted with dichloromethane (3×100 mL). The combined organic layer was washed with brine (2×150 mL), dried over anhydrous sodium sulfate, and concentrated under reduced pressure to afford crude tert-butyl (3aR,5S,6S,7R,7aR)-6,7-bis(allyloxy)-5-formyl-5,6,7,7a-tetrahydro-3aH-pyrano[3,2-d]thiazol-2-yl(ethyl)carbamate as yellow syrup, used for the next step without further purification. (ES, m/z) [M+H]$^+$ 427.0.

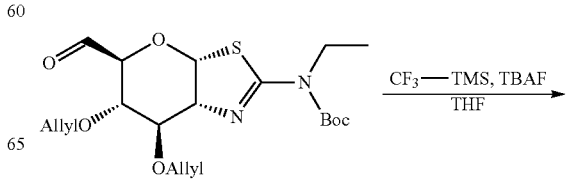

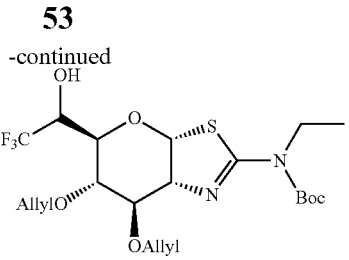

tert-butyl (3aR,5R,6S,7R,7aR)-6,7-bis(allyloxy)-5-((R)-2,2,2-trifluoro-1-hydroxyethyl)-5,6,7,7a-tetrahydro-3aH-pyrano[3,2-d]thiazol-2-yl(ethyl)carbamate A mixture of TBAF (2.7 g, 10 mmol) and 4 Å molecule sieves (2.7 g) in THF (50 mL) was stirred for 30 min at 0° C., and followed by addition of a solution of crude tert-butyl (3aR,5S,6S,7R,7aR)-6,7-bis(allyloxy)-5-formyl-5,6,7,7a-tetrahydro-3aH-pyrano[3,2-d]thiazol-2-yl(ethyl)carbamate and TMS-CF₃ (24.9 g, 175 mmol) in THF (50 mL). After stirring for 12 hours at room temperature, additional TBAF (18.3 g, 70 mmol) was added, and the mixture was stirred for 2 hours. After filtration, the filtrates were quenched by brine (100 mL), and extracted with ethyl acetate (3×100 mL). The combined organic layer was washed with brine (3×50 mL), dried over anhydrous sodium sulfate and concentrated under reduced pressure. The residue was purified by a silica gel column, eluted with 5%-25% ethyl acetate in petroleum ether to afford the product (8.7 g, 50% for 2 steps, two isomers, the ratio was 4:6 determined by ¹HNMR) as yellow oil. (ES, m/z): [M+H]⁺ 497.0. ¹H NMR (300 MHz, CDCl₃) δ 6.09-6.03 (m, 1H), 6.03-5.84 (m, 2H), 5.37-5.17 (m, 4H), 4.44-4.32 (m, 1H), 4.30-4.18 (m, 5H), 4.16-3.96 (m, 2H), 3.96-3.86 (m, 2H), 3.73-3.62 (m, 1H), 3.10 (d, J=6.0 Hz, 0.5H), 2.75 (d, J=10.5 Hz, 0.5H), 1.56 (s, 9H), 1.18 (t, J=6.9 Hz, 3H).

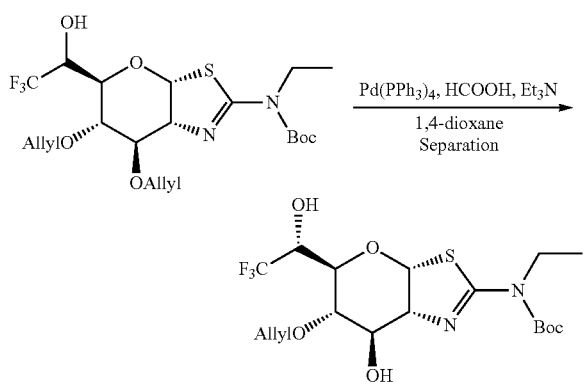

tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(ethyl)carbamate To a solution of tert-butyl (3aR,5R,6S,7R,7aR)-6,7-bis(allyloxy)-5-((R)-2,2,2-trifluoro-1-hydroxyethyl)-5,6,7,7a-tetrahydro-3aH-pyrano[3,2-d]thiazol-2-yl(ethyl)carbamate (8 g, 16 mmol) in 1,4-dioxane (150 mL) was added Pd(PPh₃)₄ (3.7 g, 3.2 mmol), Et₃N (12.9 g, 128 mmol) and HCOOH (4.4 g, 96 mmol) at room temperature under N₂ atmosphere. After stirring for 12 hours at 60° C., the reaction was quenched by H₂O (100 mL), and extracted with ethyl acetate (4×100 mL). The combined organic layer was dried over anhydrous sodium sulfate and concentrated under reduced pressure. The residue was purified by a silica gel column, eluted with 1%-10% methanol in dichloromethane to afford tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(ethyl)carbamate (2.7 g, 40%) as a light yellow solid. (ES, m/z): [M+H]⁺ 417.0. ¹HNMR (300 MHz, CDCl₃) δ 6.07 (d, J=6.3 Hz, 1H), 4.31-4.29 (m, 2H), 4.28-4.18 (m, 1H), 4.11-4.04 (m, 1H), 4.01-3.83 (m, 2H), 3.01 (s, 1H), 2.02 (s, 2H), 1.57 (s, 9H), 1.23 (t, J=6.9 Hz, 3H).

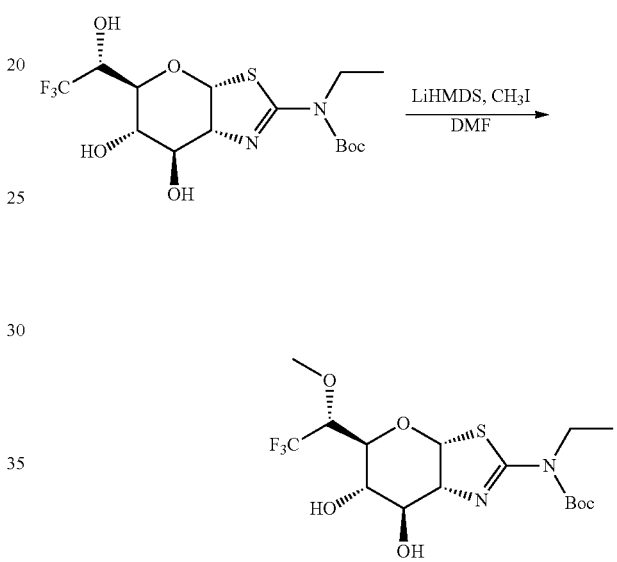

tert-butyl (3aR,5S,6S,7R,7aR)-6,7-dihydroxy-5-((R)-2,2,2-trifluoro-1-methoxyethyl)-5,6,7,7a-tetrahydro-3aH-pyrano[3,2-d]thiazol-2-yl(ethyl)carbamate A solution of tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(ethyl)carbamate (42 mg, 0.1 mmol) in DMF (10 mL) was treated with LiHMDS (0.12 mL, 0.12 mmol, 1M in THF) at 0° C. for 30 min, and followed by addition of CH₃I (28 mg, 0.2 mmol). After additional 1 hour at room temperature, the reaction was quenched by saturated aqueous NH₄Cl solution (15 mL), and extracted with ethyl acetate (3×20 mL). The combined organic layer was dried over anhydrous magnesium sulfate and concentrated under vacuum. The residue was purified by flash column chromatography with 1%-8% methanol in dichloromethane to afford the title compound as a white solid (30 mg, 69%). (ES, m/z): [M+H]⁺ 431.0. ¹H NMR (300 MHz, DMSO) δ 6.03 (d, J=6.6 Hz, 1H), 4.05-3.99 (m, 2H), 3.85-3.77 (m, 3H), 3.67-3.62 (m, 1H), 3.55 (s, 3H), 3.50-3.47 (m, 1H), 1.47 (s, 9H), 1.10 (t, J=6.9 Hz, 3H).

(3aR,5S,6S,7R,7aR)-2-(ethylamino)-5-((R)-2,2,2-trifluoro-1-methoxyethyl)-5,6,7,7a-tetrahydro-3aH-pyrano[3,2-d]thiazole-6,7-diol

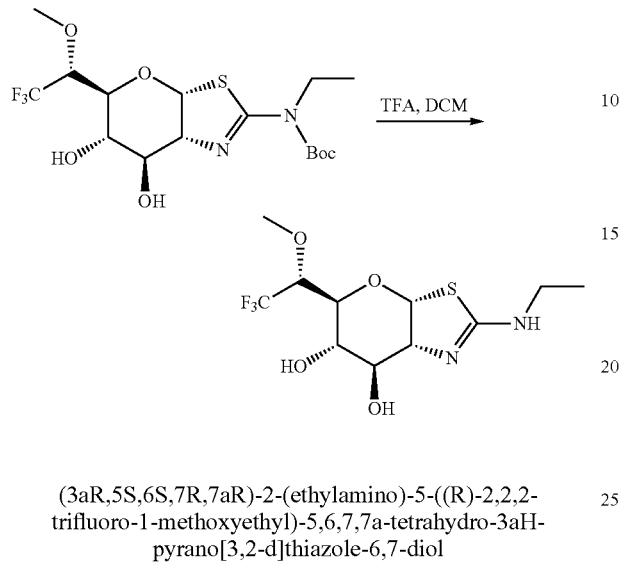

(3aR,5S,6S,7R,7aR)-2-(ethylamino)-5-((R)-2,2,2-trifluoro-1-methoxyethyl)-5,6,7,7a-tetrahydro-3aH-pyrano[3,2-d]thiazole-6,7-diol A solution of tert-butyl (3aR,5S,6S,7R,7aR)-6,7-dihydroxy-5-((R)-2,2,2-trifluoro-1-methoxyethyl)-5,6,7,7a-tetrahydro-3aH-pyrano[3,2-d]thiazol-2-yl(ethyl)carbamate (70 mg, 0.16 mmol) in dichloromethane (5 mL) was treated with trifluoroacetic acid (2 mL) for overnight at room temperature. Removing of the volatiles was performed under vacuum to give a residue, which was dissolved into methanol (5 mL) and neutralized with concentrated ammonia solution in water (1 mL). After concentrated under vacuum, the crude residue was purified by a silica gel column, eluted with 1%-5% methanol in dichloromethane to give the title compound as a white solid (40 mg, 74%). (ES, m/z) [M+H]$^+$ 331.0; $^1$HNMR (300 MHz, CD$_3$OD) δ 6.26 (d, J=6.3 Hz, 1H), 4.05-4.01 (m, 2H), 3.92-3.88 (t, J=6.0 Hz, 1H), 3.85-3.82 (d, J=9.3 Hz, 1H), 3.75-3.70 (m, 1H), 3.65 (s, 3H), 3.33-3.25 (m, 2H), 1.17 (t, J=7.2 Hz, 3H).

Examples 7 & 8

(3aR,5S,6S,7R,7aR)-2-(methylamino)-5-((R)-2,2,2-trifluoro-1-(4-nitrophenoxy)ethyl)-5,6,7,7a-tetrahydro-3aH-pyrano[3,2-d]thiazole-6,7-diol & (3aR,5S,6S,7R,7aR)-5-((R)-1-(4-aminophenoxy)-2,2,2-trifluoroethyl)-2-(methylamino)-5,6,7,7a-tetrahydro-3aH-pyrano[3,2-d]thiazole-6,7-diol

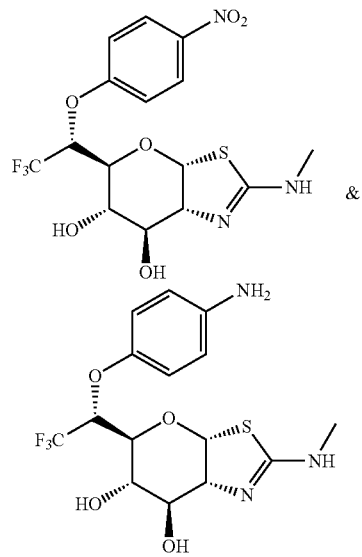

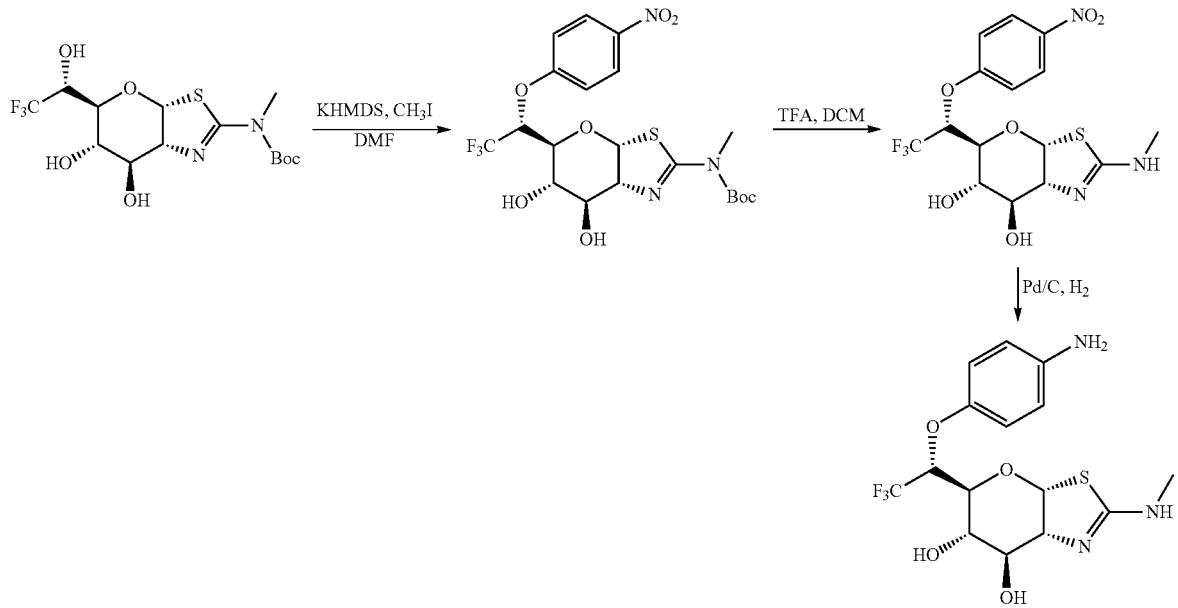

Scheme VI

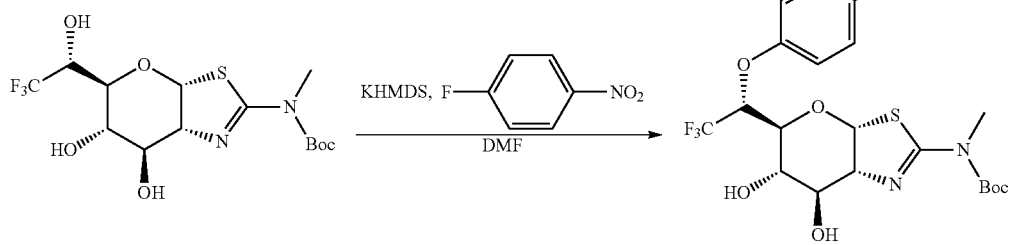

tert-butyl (3aR,5S,6S,7R,7aR)-6,7-dihydroxy-5-((R)-2,2,2-trifluoro-1-(4-nitrophenoxy)ethyl)-5,6,7,7a-tetrahydro-3aH-pyrano[3,2-d]thiazol-2-yl(methyl)carbamate A solution of tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(methyl)carbamate (900 mg, 2.2 mmol) in DMF (15 mL) was treated with KHMDS (2.4 mL, 2.4 mmol, 1M solution in THF) at 0° C. for 20 min, and followed by addition of 1-fluoro-4-nitrobenzene (632 mg, 4.48 mmol). After additional 2 hours at room temperature, the reaction was quenched by saturated aqueous NH$_4$Cl solution (15 mL) and extracted with ethyl acetate (4×30 mL). The combined organic layer was dried over anhydrous sodium sulfate, and concentrated under vacuum. The crude residue was purified by a silica gel column, eluted with 3%-35% ethyl acetate in petroleum ether to afford the product (738 mg, 63%) as a white syrup. (ES, m/z): [M+H]$^+$ 524.0. $^1$H NMR (300 MHz, CDCl$_3$) δ 8.25 (d, J=9.3 Hz, 2H), 7.24 (d, J=9.3 Hz, 2H), 6.23 (d, J=6.9 Hz, 1H), 5.13-5.07 (m, 1H), 4.23-4.21 (m, 1H), 4.16-4.09 (m, 1H), 3.96 (t, J=7.2 Hz, 1H), 3.79-3.72 (m, 1H), 3.06 (s, 3H), 1.55 (s, 9H).

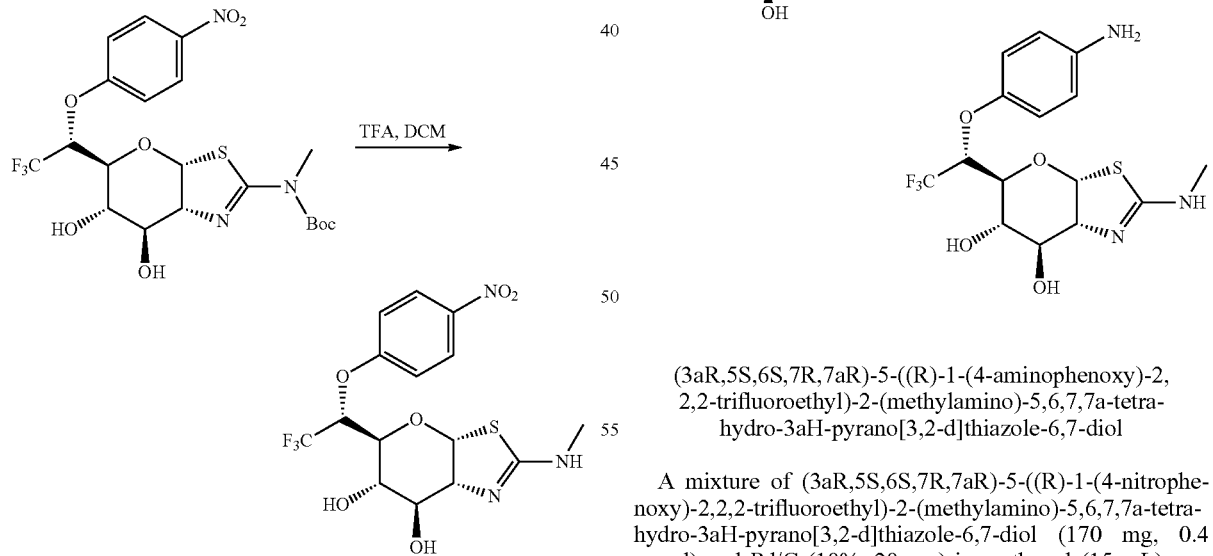

(3aR,5S,6S,7R,7aR)-2-(methylamino)-5-((R)-2,2,2-trifluoro-1-(4-nitrophenoxy)ethyl)-5,6,7,7a-tetrahydro-3aH-pyrano[3,2-d]thiazole-6,7-diol A solution of tert-butyl (3aR,5S,6S,7R,7aR)-6,7-dihydroxy-5-((R)-2,2,2-trifluoro-1-(4-nitrophenoxy)ethyl)-5,6,7,7a-tetrahydro-3aH-pyrano[3,2-d]thiazol-2-yl(methyl)carbamate (640 mg, 1.2 mmol) in dichloromethane (20 ml) was treated with trifluoroacetic acid (0.7 mL) for 1 hour at room temperature. Removal of volatiles gave a residue, which was dissolved into methanol (5 mL) and neutralized with concentrated NH$_4$OH (3 mL). After concentrated under reduced pressure, the crude product was purified by a silica gel column, eluted with 5%-20% methanol in dichloromethane to give the title compound (355 mg, 69%) as a white solid. (ES, m/z): [M+H]$^+$ 424.0. $^1$H NMR (300 MHz, CD$_3$OD) δ 8.28 (d, J=9.3 Hz, 2H), 7.36 (d, J=9.3 Hz, 2H), 6.37 (d, J=6.3 Hz, 1H), 5.44-5.41 (m, 1H), 4.13-4.07 (m, 2H), 3.97 (t, J=5.4 Hz, 1H), 3.65-3.59 (m, 1H), 2.87 (s, 3H).

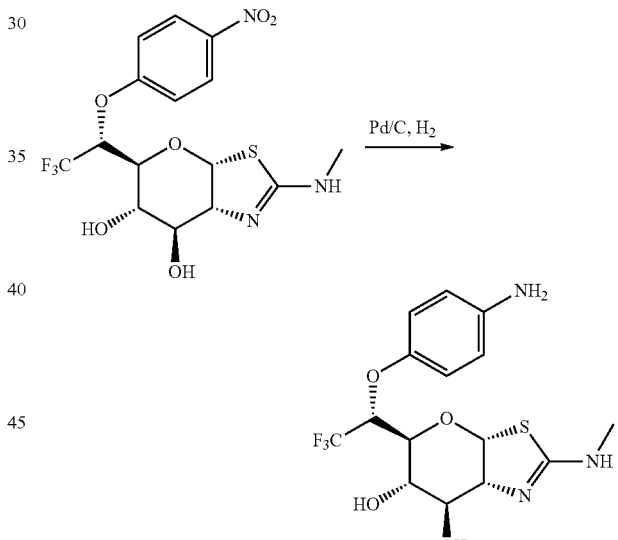

(3aR,5S,6S,7R,7aR)-5-((R)-1-(4-aminophenoxy)-2,2,2-trifluoroethyl)-2-(methylamino)-5,6,7,7a-tetrahydro-3aH-pyrano[3,2-d]thiazole-6,7-diol A mixture of (3aR,5S,6S,7R,7aR)-5-((R)-1-(4-nitrophenoxy)-2,2,2-trifluoroethyl)-2-(methylamino)-5,6,7,7a-tetrahydro-3aH-pyrano[3,2-d]thiazole-6,7-diol (170 mg, 0.4 mmol) and Pd/C (10%, 20 mg) in methanol (15 mL) was stirred for 4 hours at room temperature under hydrogen atmosphere (1 atm). The solids were filtered out and the solvent was removed under vacuum. The residue was purified by reverse-phase preparative HPLC with the following conditions (Column, Sun fire prep C18; mobile phase, water with 0.05% NH$_4$OH and CH$_3$CN (25% up to 55% in 11 min); Detector, UV 220 nm) to afford the product as a white solid (67 mg, 42%). (ES, m/z) [M+H]+ 394.0. ¹H NMR (400 MHz, CD₃OD) δ 6.93 (d, J=8.8 Hz, 2H), 6.72 (d, J=8.8 Hz, 2H), 6.39 (d, J=6.4 Hz, 1H), 4.87-4.85 (m, 1H), 4.11 (t, J=5.6 Hz, 1H), 3.99-3.97 (m, 2H), 3.83-3.82 (m, 1H), 2.88 (s, 3H).

Example 9

(3aR,5S,6S,7R,7aR)-2-(dimethylamino)-5-((R)-2,2,2-trifluoro-1-(4-nitrophenoxy)ethyl)-5,6,7,7a-tetrahydro-3aH-pyrano[3,2-d]thiazole-6,7-diol

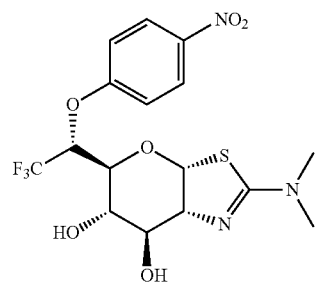 [SMILES: CN(C)C1=N[C@@H]2[C@@H](O)[C@H](O)[C@@H]([C@@H](Oc3ccc([N+](=O)[O-])cc3)C(F)(F)F)O[C@@H]2S1]

Scheme VII

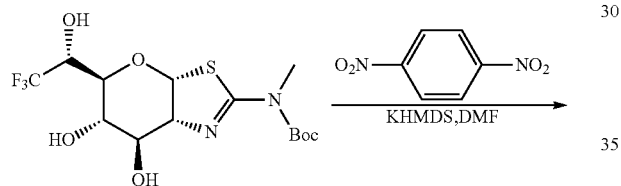

(3aR,5S,6S,7R,7aR)-2-(dimethylamino)-5-((R)-2,2,2-trifluoro-1-(4-nitrophenoxy)ethyl)-5,6,7,7a-tetrahydro-3aH-pyrano[3,2-d]thiazole-6,7-diol A solution of (3aR,5S,6S,7R,7aR)-2-(dimethylamino)-5-((R)-2,2,2-trifluoro-1-(hydroxyethyl)-5,6,7,7a-tetrahydro-3aH-pyrano[3,2-d]thiazole-6,7-diol (93 mg, 0.3 mmol) in DMF (5 mL) was treated with KHMDS (0.3 mL, 0.3 mmol, 1M solution in THF) at 0° C. for 10 min, and followed by addition of 1-fluoro-4-nitrobenzene (140 mg, 1.0 mmol). After additional 1 hour at room temperature, the reaction was quenched by saturated aqueous NH₄Cl solution (5 mL) and extracted with ethyl acetate (3×10 mL). The combined organic layer was dried over anhydrous sodium sulfate, and concentrated under vacuum. The crude residue was purified by reverse-phase preparative HPLC with the following conditions (Column, Sun fire prep. C18; mobile phase, water with 0.03% NH₄OH and CH₃CN (25% up to 55% in 10 min); Detector, UV 220 nm) to afford the title compound as a light-yellow solid (65 mg, 50%). (ES, m/z) [M+H]+ 438.0. ¹H NMR (400 MHz, CDCl₃) δ 8.26 (d, J=9.2 Hz, 2H), 7.25 (d, J=9.2 Hz, 2H), 6.42 (d, J=6.4 Hz, 1H), 5.11-5.09 (m, 1H), 4.23-4.17 (m, 2H), 4.05 (t, J=6.4 Hz, 1H), 3.74 (dd, J=8.6, 6.6 Hz, 1H), 3.06 (s, 6H).

Examples 10 & 11

(3aR,5S,6S,7R,7aR)-2-(dimethylamino)-5-((R)-1-methoxyethyl)-5,6,7,7a-tetrahydro-3aH-pyrano[3,2-d]thiazole-6,7-diol & (3aR,5S,6S,7R,7aR)-2-(dimethylamino)-5-((S)-1-methoxyethyl)-5,6,7,7a-tetrahydro-3aH-pyrano[3,2-d]thiazole-6,7-diol

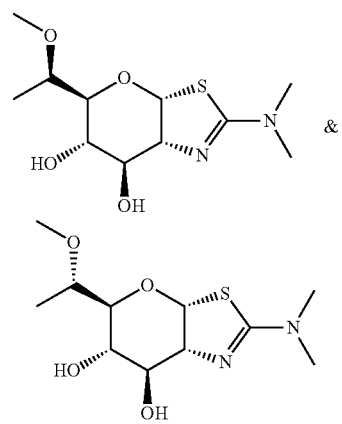

Scheme VIII

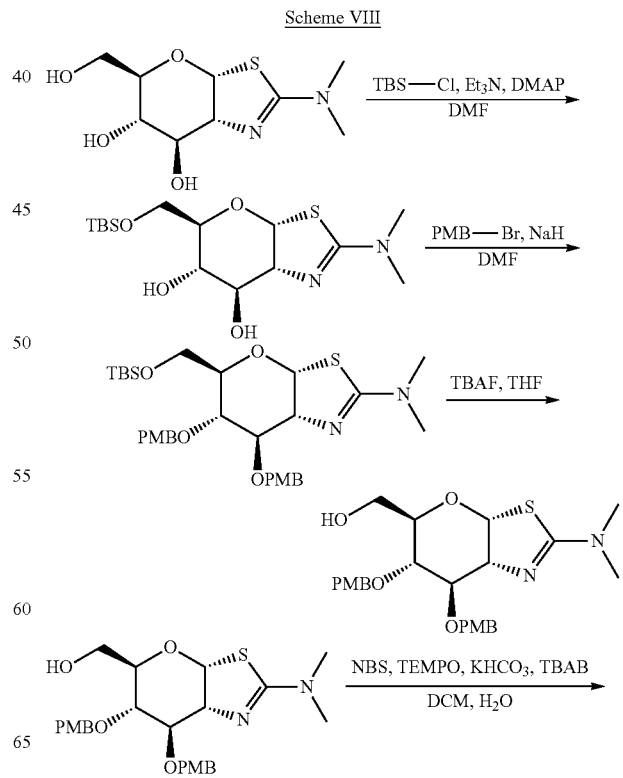

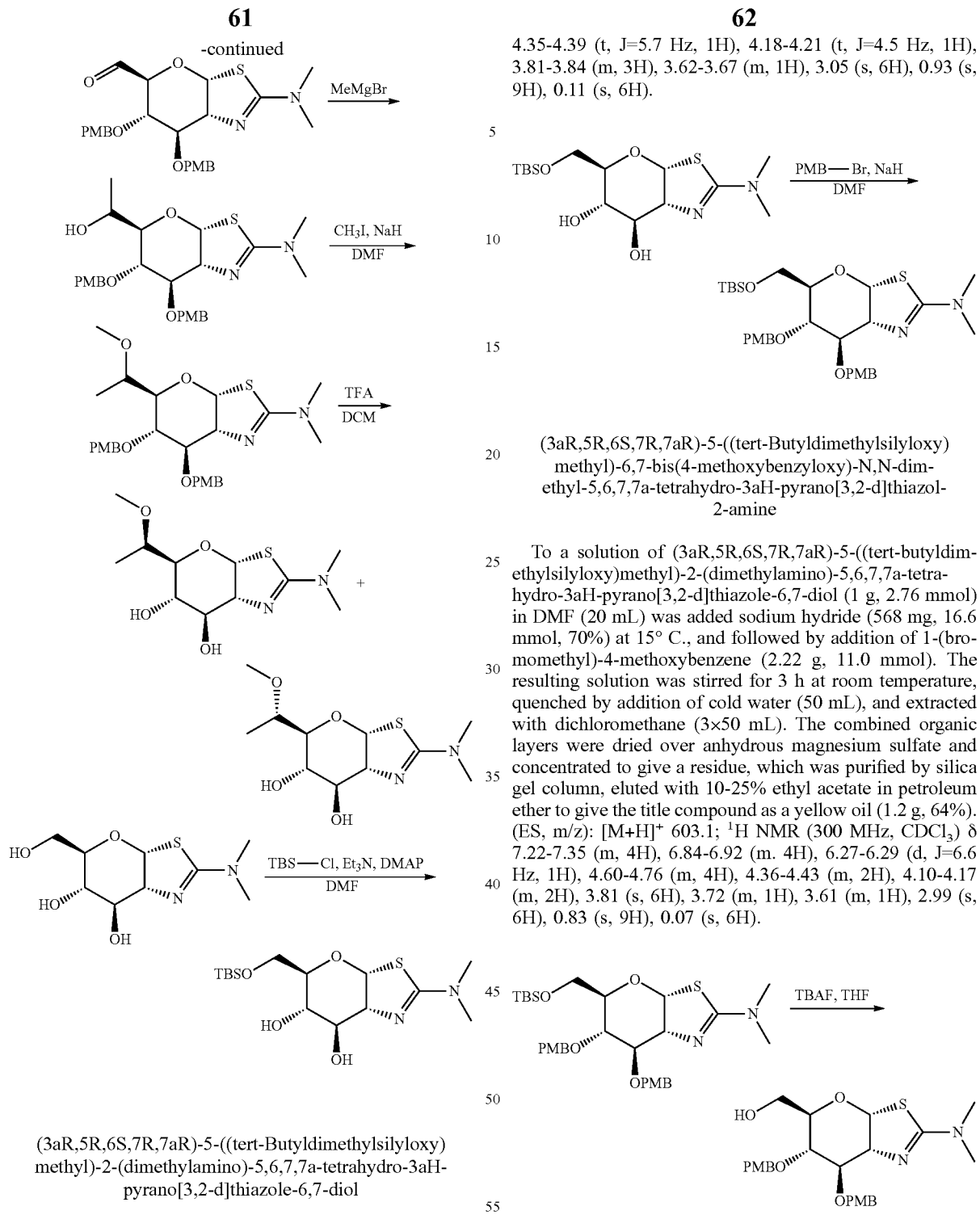

(3aR,5R,6S,7R,7aR)-5-((tert-Butyldimethylsilyloxy)methyl)-2-(dimethylamino)-5,6,7,7a-tetrahydro-3aH-pyrano[3,2-d]thiazole-6,7-diol To a solution of (3aR,5R,6S,7R,7aR)-2-(dimethylamino)-5-(hydroxymethyl)-5,6,7,7a-tetrahydro-3aH-pyrano[3,2-d]thiazole-6,7-diol (1 g, 4.03 mmol), DMAP (49.2 mg, 0.40 mmol) and triethylamine (611 mg, 6.05 mmol) in DMF (50 mL) was added tert-butylchlorodimethylsilane (665 mg, 4.43 mmol). After stirred overnight at 50° C., the resulting mixture was concentrated under vacuum to provide a residue, which was purified by silica gel column, eluted with 2-5% MeOH in dichloromethane to give the title compound as a yellow solid (1.0 g, 65%). (ES, m/z): [M+H]⁺ 263.0; ¹H NMR (300 MHz, CDCl₃) δ 6.33-6.35 (d, J=6.3 Hz, 1H), 4.35-4.39 (t, J=5.7 Hz, 1H), 4.18-4.21 (t, J=4.5 Hz, 1H), 3.81-3.84 (m, 3H), 3.62-3.67 (m, 1H), 3.05 (s, 6H), 0.93 (s, 9H), 0.11 (s, 6H).

(3aR,5R,6S,7R,7aR)-5-((tert-Butyldimethylsilyloxy)methyl)-6,7-bis(4-methoxybenzyloxy)-N,N-dimethyl-5,6,7,7a-tetrahydro-3aH-pyrano[3,2-d]thiazol-2-amine To a solution of (3aR,5R,6S,7R,7aR)-5-((tert-butyldimethylsilyloxy)methyl)-2-(dimethylamino)-5,6,7,7a-tetrahydro-3aH-pyrano[3,2-d]thiazole-6,7-diol (1 g, 2.76 mmol) in DMF (20 mL) was added sodium hydride (568 mg, 16.6 mmol, 70%) at 15° C., and followed by addition of 1-(bromomethyl)-4-methoxybenzene (2.22 g, 11.0 mmol). The resulting solution was stirred for 3 h at room temperature, quenched by addition of cold water (50 mL), and extracted with dichloromethane (3×50 mL). The combined organic layers were dried over anhydrous magnesium sulfate and concentrated to give a residue, which was purified by silica gel column, eluted with 10-25% ethyl acetate in petroleum ether to give the title compound as a yellow oil (1.2 g, 64%). (ES, m/z): [M+H]⁺ 603.1; ¹H NMR (300 MHz, CDCl₃) δ 7.22-7.35 (m, 4H), 6.84-6.92 (m. 4H), 6.27-6.29 (d, J=6.6 Hz, 1H), 4.60-4.76 (m, 4H), 4.36-4.43 (m, 2H), 4.10-4.17 (m, 2H), 3.81 (s, 6H), 3.72 (m, 1H), 3.61 (m, 1H), 2.99 (s, 6H), 0.83 (s, 9H), 0.07 (s, 6H).

((3aR,5R,6S,7R,7aR)-2-(Dimethylamino)-6,7-bis(4-methoxybenzyloxy)-5,6,7,7a-tetrahydro-3aH-pyrano[3,2-d]thiazol-5-yl)methanol (3aR,5R,6S,7R,7aR)-6,7-bis(4-methoxybenzyloxy)-5-((tert-butyldimethylsilyloxy)methyl)-N,N-dimethyl-5,6,7,7a-tetrahydro-3aH-pyrano[3,2-d]thiazol-2-amine (9.5 g, 15.8 mmol) in THF (100 mL) was treated with TBAF (8.27 g, 31.6 mmol) overnight at room temperature. The resulting solution was diluted with brine (200 mL), extracted with ethyl acetate (2×200 mL), and dried over anhydrous magnesium sulfate. After removal of solvents, the residue was purified by silica gel column, eluted with 1-2.5% MeOH in dichloromethane to give the title compound as a yellow oil (7.0 g, 86%). (ES, m/z): [M+H]+ 489.0; 1H NMR (300 MHz, CDCl3) δ 7.32-7.62 (m, 2H), 7.22-7.28 (m, 2H), 6.85-6.91 (m, 4H), 6.26-6.28 (d, J=6.6 Hz, 1H), 4.52-4.73 (m, 4H), 4.31-4.34 (d, J=11.4 Hz, 1H), 4.23 (s, 1H), 3.81 (s, 6H), 3.53-3.76 (m, 4H), 3.01 (m, 6H), 1.78-1.82 (m, 1H).

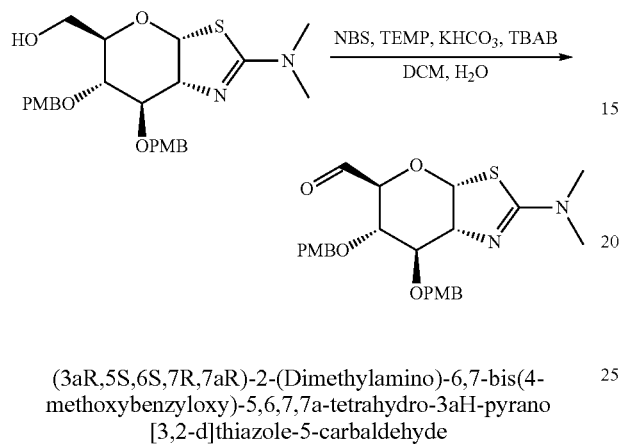

(3aR,5S,6S,7R,7aR)-2-(Dimethylamino)-6,7-bis(4-methoxybenzyloxy)-5,6,7,7a-tetrahydro-3aH-pyrano[3,2-d]thiazole-5-carbaldehyde To a mixture of ((3aR,5R,6S,7R,7aR)-6,7-bis(4-methoxybenzyloxy)-2-(dimethylamino)-5,6,7,7a-tetrahydro-3aH-pyrano[3,2-d]thiazol-5-yl)methanol (500 mg, 1.0 mmol), TBAB (16.5 mg, 0.05 mmol), KHCO3 (461 mg, 4.6 mmol) and TEMPO (8 mg, 0.05 mmol) in dichloromethane (25 mL) and H2O (5 mL) was added NBS (201 mg, 1.13 mmol) at 15° C. After stirred for 30 min, the reaction mixture was quenched by saturated Na2SO3 (5 mL). The organic layer was dried over anhydrous magnesium sulfate and condensed to provide a residue, which was purified by silica gel column, eluted with 20-30% ethyl acetate in dichloromethane to give the product as a yellow syrup (320 mg, 75% pure). (ES, m/z): [M+H]+ 487.0. 1H NMR (300 MHz, CDCl3) δ 9.61 (s, 1H), 7.22-7.34 (m, 4H), 6.83-6.92 (m, 4H), 6.11-6.13 (d, J=6.0 Hz, 1H), 4.17-4.67 (m, 8H), 3.83 (s, 6H), 3.00-3.04 (s, 6H).

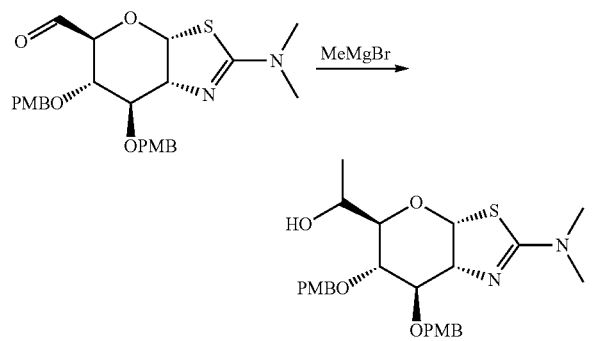

1-((3aR,5R,6S,7R,7aR)-6,7-Bis(4-methoxybenzyloxy)-2-(dimethylamino)-5,6,7,7a-tetrahydro-3aH-pyrano[3,2-d]thiazol-5-yl)ethanol To a solution of (3aR,5S,6S,7R,7aR)-6,7-bis(4-methoxybenzyloxy)-2-(dimethylamino)-5,6,7,7a-tetrahydro-3aH-pyrano[3,2-d]thiazole-5-carbaldehyde (260 mg, 0.53 mmol) in THF (10 mL) was added methylmagnesium bromide (0.3 mL, 3M in THF). After stirred for 2 h at room temperature, the reaction mixture was quenched with sat. NH4Cl (aq, 20 mL), extracted with ethyl acetate (3×20 mL). The combined organic layers were dried over anhydrous magnesium sulfate, concentrated under vacuum to give a residue, which was purified by silica gel column, eluted with 1-2% MeOH in dichloromethane to give the product as a yellow syrup (250 mg, 74%, two diastereomers, faster moving one:slower moving one=1:5). (ES, m/z): [M+H]+ 503.0; 1H NMR (300 MHz, CDCl3) δ 7.26-7.35 (m, 2H), 7.22-7.28 (m, 2H), 6.85-6.91 (m, 4H), 6.29-6.31 (d, J=6.9 Hz, 1H), 4.52-4.73 (m, 4H), 4.31-4.34 (d, J=11.4 Hz, 1H), 4.23 (s, 1H), 3.81 (s, 6H), 3.53-3.76 (m, 4H), 3.01 (m, 6H), 1.19-1.21 (d, J=6.6 Hz, 3H).

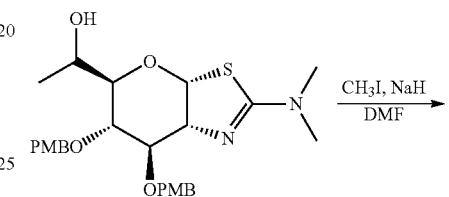

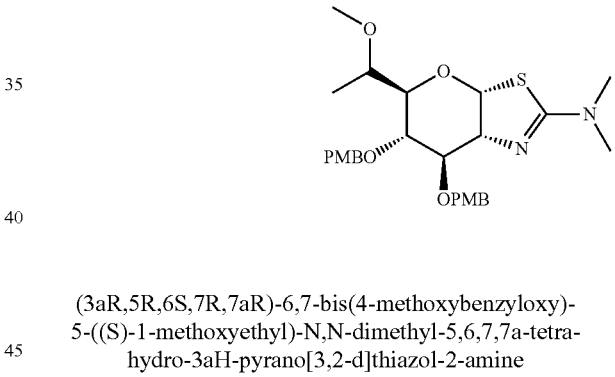

(3aR,5R,6S,7R,7aR)-6,7-bis(4-methoxybenzyloxy)-5-((S)-1-methoxyethyl)-N,N-dimethyl-5,6,7,7a-tetrahydro-3aH-pyrano[3,2-d]thiazol-2-amine A solution of (S)-1-((3aR,5R,6S,7R,7aR)-2-(dimethylamino)-6,7-bis(4-methoxybenzyloxy)-5,6,7,7a-tetrahydro-3aH-pyrano[3,2-d]thiazol-5-yl)ethanol (450 mg, 0.8 mmol), two diastereomers, ratio is 1:5 by 1H NMR) in DMF (10 mL) was treated with sodium hydride (70 mg, 1.7 mmol, 60% dispersed by mineral oil) for 30 min at 0° C., and followed by addition of iodomethane (255 mg, 1.8 mmol). After kept 2 hours at room temperature, the reaction was quenched by saturated aqueous NH4Cl solution (20 mL) and extracted with ethyl acetate (3×20 mL). The combined organic layer was washed with brine (3×20 mL), dried over anhydrous sodium sulfate and concentrated under vacuum. The residue was purified by a silica gel column, eluted with 10%-20% ethyl acetate in petroleum ether to give the title compound as light yellow oil (300 mg, 65%). (ES, m/z): [M+H]+ 517.0; 1H NMR (300 MHz, CDCl3) δ 7.36-7.33 (m, 2H), 7.28-7.23 (m, 2H), 6.90-6.84 (m, 4H), 6.36 (d, J=6.6 Hz, 1H), 4.52-4.73 (m, 4H), 4.31-4.34 (d, J=11.4 Hz, 1H), 3.81 (s, 6H), 3.53-3.76 (m, 4H), 3.30 (s, 3H), 3.01 (m, 6H), 1.18-1.09 (m, 3H).

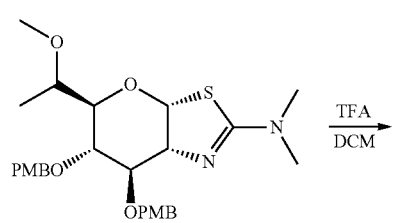

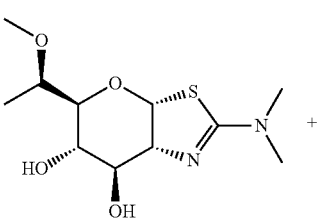

(3aR,5S,6S,7R,7aR)-2-(dimethylamino)-5-((R)-1-methoxyethyl)-5,6,7,7a-tetrahydro-3aH-pyrano[3,2-d]thiazole-6,7-diol & (3aR,5S,6S,7R,7aR)-2-(dimethylamino)-5-((S)-1-methoxyethyl)-5,6,7,7a-tetrahydro-3aH-pyrano[3,2-d]thiazole-6,7-diol A solution of (3aR,5R,6S,7R,7aR)-6,7-bis(4-methoxybenzyloxy)-5-((S)-1-methoxyethyl)-N,N-dimethyl-5,6,7,7a-tetrahydro-3aH-pyrano[3,2-d]thiazol-2-amine (200 mg, 0.4 mmol) in dichloromethane (5 ml) was treated with trifluoroacetic acid (0.5 mL) for 1 hour at room temperature. Removal of volatiles gave a residue, which was dissolved into methanol (5 mL) and neutralized with concentrated NH$_4$OH (2 mL). After concentrated under reduced pressure, the crude product was purified by a silica gel column, eluted with 5%-20% methanol in dichloromethane to give a mixture of the above two compounds. Separation by Prep-HPLC with the following conditions (Column, Sun fire prep. C18; mobile phase, water with 0.03% NH$_4$OH and CH$_3$CN (15% up to 45% in 8 min); Detector, UV 220 nm) gave (3aR,5S,6S,7R,7aR)-2-(dimethylamino)-5-((R)-1-methoxyethyl)-5,6,7,7a-tetrahydro-3aH-pyrano[3,2-d]thiazole-6,7-diol as white solid (6.8 mg, 7%, faster eluting isomer); (ES, m/z): [M+H]$^+$ 277.0; $^1$H NMR (300 MHz, D$_2$O) δ 6.24 (d, J=6.6 Hz, 1H), 4.16 (t, J=6.3 Hz, 1H), 3.98 (t, J=4.2 Hz, 1H), 3.65-3.58 (m, 2H), 3.54-3.52 (m, 1H), 3.28 (s, 3H), 2.93 (s, 6H), 1.12 (d, J=6.3 Hz, 3H); and (3aR,5S,6S,7R,7aR)-2-(dimethylamino)-5-((S)-1-methoxyethyl)-5,6,7,7a-tetrahydro-3aH-pyrano[3,2-d]thiazole-6,7-diol as white solid (58 mg, 56%, slower eluting isomer). (ES, m/z): [M+H]$^+$ 277.0; $^1$H NMR (300 MHz, D$_2$O) δ 6.19 (d, J=6.6 Hz, 1H), 4.12 (t, J=5.7 Hz, 1H), 3.94 (t, J=5.1 Hz, 1H), 3.54-3.66 (m, 2H), 3.32-3.36 (m, 1H), 3.28 (s, 3H), 2.90 (s, 6H), 1.12 (d, J=6.3 Hz, 3H)

Examples 12 & 13

(3aR,5R,6S,7R,7aR)-5-((R)-1-(cyclopentylamino)ethyl)-2-(methylamino)-5,6,7,7a-tetrahydro-3aH-pyrano[3,2-d]thiazole-6,7-diol & (3aR,5R,6S,7R,7aR)-5-((S)-1-(cyclopentylamino)ethyl)-2-(methylamino)-5,6,7,7a-tetrahydro-3aH-pyrano[3,2-d]thiazole-6,7-diol

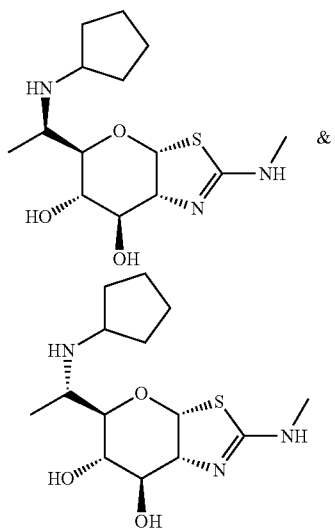

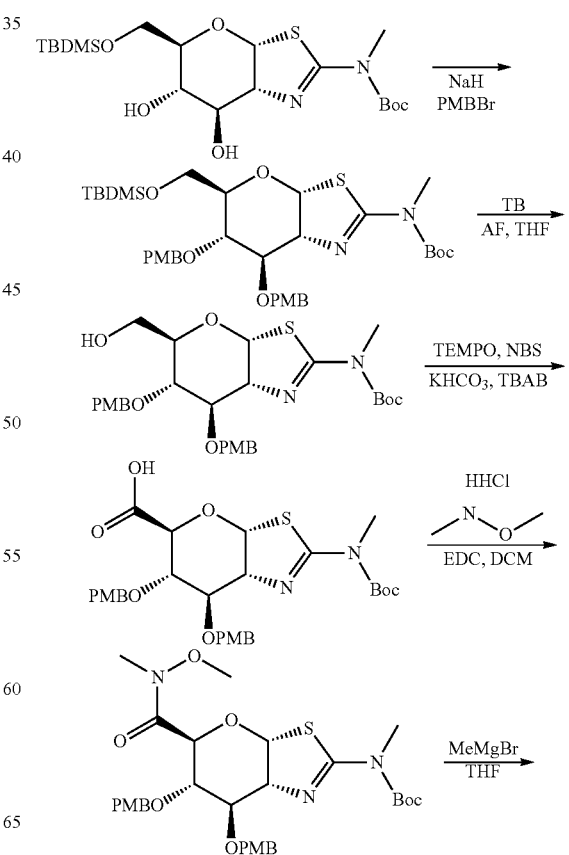

-continued

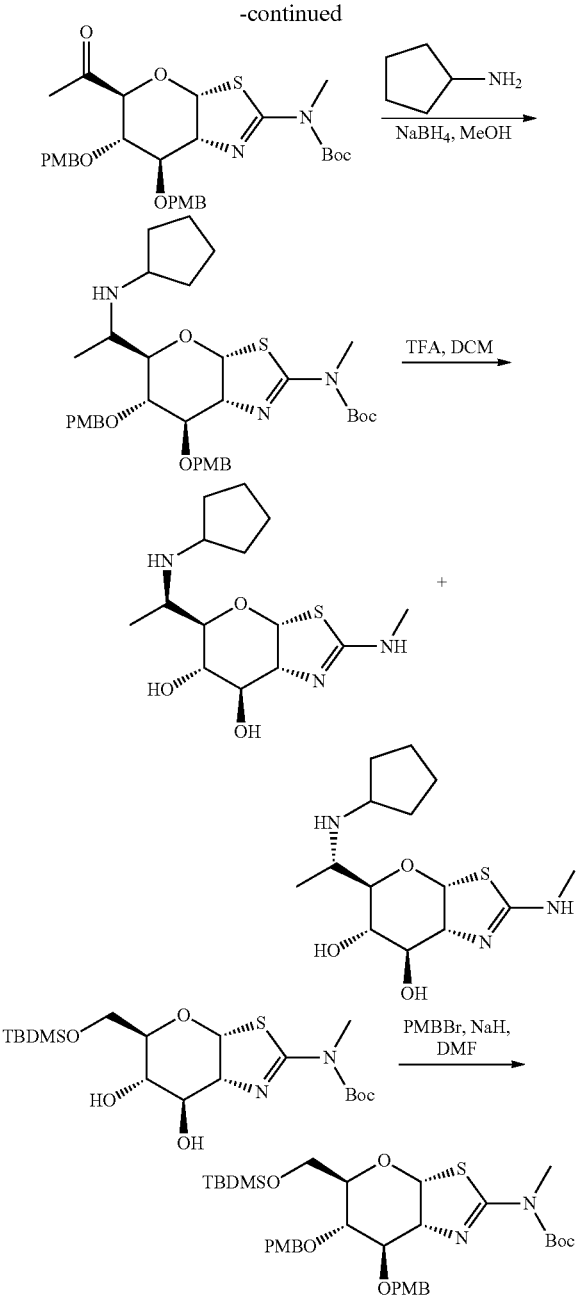

tert-Butyl (3aR,5R,6S,7R,7aR)-5-((tert-butyldimeth-ylsilyloxy)methyl)-6,7-bis(4-methoxybenzyloxy)-5,6,7,7a-tetrahydro-3aH-pyrano[3,2-d]thiazol-2-yl(methyl)carbamate To a solution of (3aR,5R,6S,7R,7aR)-5-((tert-butyldimethylsilyloxy)methyl)-6,7-dihydroxy-5,6,7,7a-tetrahydro-3aH-pyrano[3,2-d]thiazol-2-yl(methyl)carbamate (20 g, 45 mmol) in DMF (150 mL) was added sodium hydride (10.7 g, 446 mmol) in portion at 0° C., and followed by addition of 1-(bromomethyl)-4-methoxybenzene (36 g, 179 mmol). The resulting solution was stirred for 2 h at room temperature, quenched with cold water (200 mL), and extracted with ethyl acetate (3×500 mL). The combined organic layers were washed with brine (5×200 mL), dried over anhydrous magnesium sulfate, and concentrated under vacuum to afford a residue, which was purified by silica gel column, eluted with 10% ethyl acetate in petroleum ether to give the product as a yellow liquid (21 g, 68%). (ES, m/z): [M+H]+ 689.1. $^1$H NMR (300 MHz, CDCl$_3$) δ 7.31-7.37 (m, 2H), 7.22-7.28 (m, 2H), 6.10-6.12 (d, J=6.9 Hz, 1H), 4.60-4.74 (m, 4H), 4.20-4.47 (m, 4H), 3.82 (s, 6H), 3.69 (s, 3H), 3.33-3.37 (m, 2H), 1.56 (s, 9H), 0.89 (s, 9H), 0.05 (s, 6H).

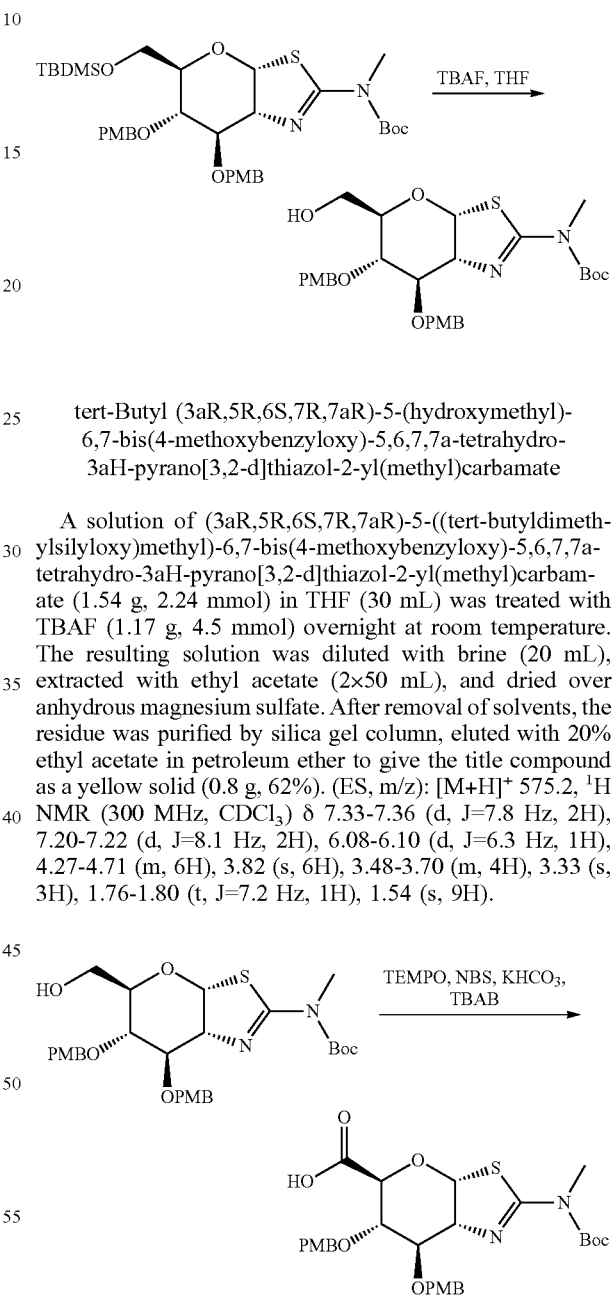

tert-Butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl(methyl)carbamate A solution of (3aR,5R,6S,7R,7aR)-5-((tert-butyldimethylsilyloxy)methyl)-6,7-bis(4-methoxybenzyloxy)-5,6,7,7a-tetrahydro-3aH-pyrano[3,2-d]thiazol-2-yl(methyl)carbamate (1.54 g, 2.24 mmol) in THF (30 mL) was treated with TBAF (1.17 g, 4.5 mmol) overnight at room temperature. The resulting solution was diluted with brine (20 mL), extracted with ethyl acetate (2×50 mL), and dried over anhydrous magnesium sulfate. After removal of solvents, the residue was purified by silica gel column, eluted with 20% ethyl acetate in petroleum ether to give the title compound as a yellow solid (0.8 g, 62%). (ES, m/z): [M+H]+ 575.2, $^1$H NMR (300 MHz, CDCl$_3$) δ 7.33-7.36 (d, J=7.8 Hz, 2H), 7.20-7.22 (d, J=8.1 Hz, 2H), 6.08-6.10 (d, J=6.3 Hz, 1H), 4.27-4.71 (m, 6H), 3.82 (s, 6H), 3.48-3.70 (m, 4H), 3.33 (s, 3H), 1.76-1.80 (t, J=7.2 Hz, 1H), 1.54 (s, 9H).

(3aR,5S,6S,7R,7aR)-2-(tert-Butoxycarbonyl(methyl)amino)-6,7-bis(4-methoxybenzyloxy)-5,6,7,7a-tetrahydro-3aH-pyrano[3,2-d]thiazole-5-carboxylic acid A mixture of tert-butyl (3aR,5R,6S,7R,7aR)-5-(hydroxymethyl)-6,7-bis(4-methoxybenzyloxy)-5,6,7,7a-tetrahydro-3aH-pyrano[3,2-d]thiazol-2-yl(methyl)carbamate (1 g, 1.74 mmol), KHCO₃ (780 mg, 7.8 mmol), TBAB (28 mg, 0.09 mmol) and TEMPO (14 mg, 0.09 mmol) in dichloromethane (30 mL) and H₂O (6 mL) was treated with NBS (620 mg, 3.5 mmol) overnight at room temperature. The reaction mixture was adjusted to acidic (pH at 3) with hydrochloric acid, and then extracted with dichloromethane (3×20 mL). The combined organic layers were dried over anhydrous sodium sulfate and concentrated under vacuum to provide a residue, which was purified by a silica gel column, eluted with 20~50% ethyl acetate in petroleum ether to give the title compound as a white solid (600 mg, 58%). (ES, m/z): [M+H]⁺ 589.0, ¹H NMR (300 MHz, CDCl₃) δ 7.25-7.32 (m, 2H), 6.85-6.90 (m, 2H), 6.08-6.10 (d, J=6.3 Hz, 1H), 4.50-4.62 (m, 5H), 4.22-4.29 (m, 2H), 3.97 (m, 1H), 3.81 (s, 6H), 3.34 (s, 3H), 1.54 (s, 9H).

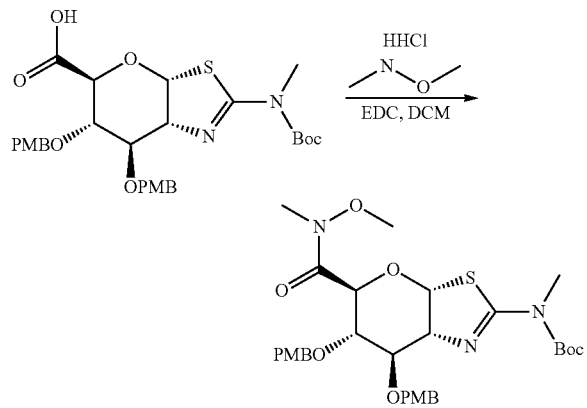

tert-butyl (3aR,5S,6S,7R,7aR)-5-(methoxy(methyl) carbamoyl)-6,7-bis(4-methoxybenzyloxy)-5,6,7,7a-tetrahydro-3aH-pyrano[3,2-d]thiazol-2-yl(methyl) carbamate A solution of (3aR,5S,6S,7R,7aR)-6,7-bis(4-methoxybenzyloxy)-2-(tert-butoxycarbonyl)-5,6,7,7a-tetrahydro-3aH-pyrano[3,2-d]thiazole-5-carboxylic acid (600 mg, 1 mmol), N-methoxymethanamine hydrochloride (198 mg, 2 mmol) and triethylamine (0.7 mL) in dichloromethane (30 mL) was treated with EDC (392 mg, 2 mmol) for 2 hours at room temperature. The reaction was quenched by brine (30 mL) and extracted with dichloromethane (3×30 mL). The combined organic layer was dried over anhydrous magnesium sulfate and concentrated under vacuum to give a residue, which was purified by a silica gel column, eluted with 10%-20% ethyl acetate in petroleum ether to give the title compound as a white solid (550 mg, 85%). (ES, m/z): [M+H]⁺ 632.1; ¹H NMR (300 MHz, CDCl₃) δ 7.29-7.21 (m, 4H), 6.91-6.83 (m, 4H), 6.08 (d, J=5.7 Hz, 1H), 4.61-4.48 (m, 4H), 4.31-4.30 (m, 1H), 4.29-4.22 (m, 2H), 4.19-4.17 (t, J=4.8 Hz, 1H), 3.82 (s, 6H), 3.71 (s, 3H), 3.67 (s, 3H), 3.30 (s, 3H), 1.54 (s, 9H).

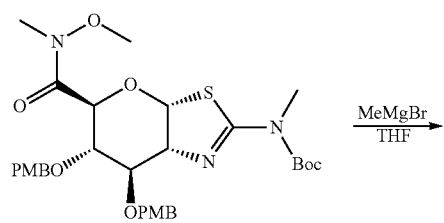

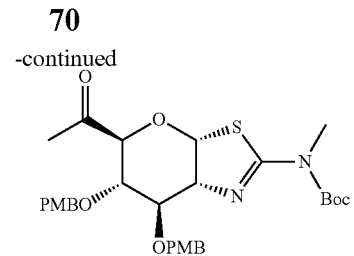

tert-butyl (3aR,5S,6S,7R,7aR)-5-acetyl-6,7-bis(4-methoxybenzyloxy)-5,6,7,7a-tetrahydro-3aH-pyrano[3,2-d]thiazol-2-yl(methyl)carbamate A solution of tert-butyl (3aR,5S,6S,7R,7aR)-5-(methoxy (methyl)carbamoyl)-6,7-bis(4-methoxybenzyloxy)-5,6,7,7a-tetrahydro-3aH-pyrano[3,2-d]thiazol-2-yl(methyl)carbamate (631 mg, 1 mmol) in THF (10 mL) was treated with methylmagnesium bromide (0.6 mL, 1.2 mmol, 2M in THF) for 1 hour at room temperature. The reaction was quenched by saturated aqueous NH₄Cl solution (20 mL) and extracted with ethyl acetate (3×20 mL). The combined organic layer was washed with brine (2×20 mL), dried over anhydrous magnesium sulfate, and concentrated under vacuum to give the title compound as a light yellow syrup (410 mg, 70%). (ES, m/z): [M+H]⁺ 587.0; ¹H NMR (300 MHz, CDCl₃) δ 7.31-7.23 (m, 4H), 6.94-6.87 (m, 4H), 6.21 (d, J=6.6 Hz, 1H), 4.63-4.51 (m, 4H), 4.33-4.31 (m, 1H), 4.28-4.23 (m, 2H), 4.21-4.18 (m, 1H), 3.84 (s, 6H), 3.30 (s, 3H), 2.45 (s, 3H), 1.54 (s, 9H)

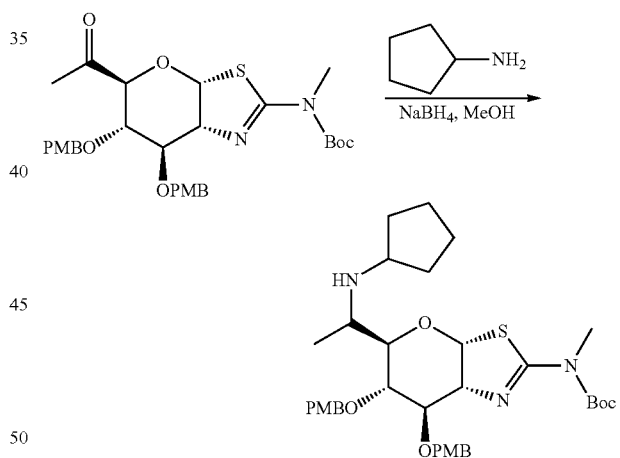

tert-butyl (3aR,5R,6S,7R,7aR)-5-((S)-1-(cyclopentylamino)ethyl)-6,7-bis(4-methoxybenzyloxy)-5,6,7,7a-tetrahydro-3aH-pyrano[3,2-d]thiazol-2-yl (methyl)carbamate A solution of tert-butyl (3aR,5S,6S,7R,7aR)-5-acetyl-6,7-bis(4-methoxybenzyloxy)-5,6,7,7a-tetrahydro-3aH-pyrano[3,2-d]thiazol-2-yl(methyl)carbamate (117 mg, 0.2 mmol) and cyclopentanamine (145 mg, 1.7 mmol) in methanol (10 mL) was stirred for 2 hours at 50° C., and followed by addition of NaBH₄ (19 mg, 0.5 mmol). After additional 2 hours, the reaction was quenched by water (20 mL) and extracted with ethyl acetate (3×50 mL). The organic layers were dried over magnesium sulfate, and concentrated under vacuum to give the crude product as a yellow syrup, which was used in the next step without further purification. (ES, m/z): [M+H]+ 656.0.

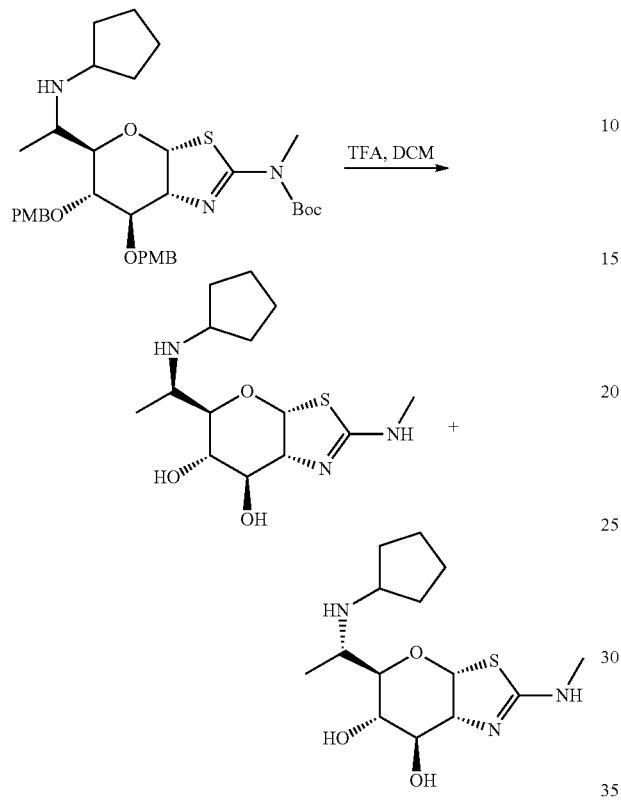

(3aR,5R,6S,7R,7aR)-5-((R)-1-(cyclopentylamino)
ethyl)-2-(methylamino)-5,6,7,7a-tetrahydro-3aH-
pyrano[3,2-d]thiazole-6,7-diol & (3aR,5R,6S,7R,
7aR)-5-((S)-1-(cyclopentylamino)ethyl)-2-
(methylamino)-5,6,7,7a-tetrahydro-3aH-pyrano[3,2-
d]thiazole-6,7-diol The resulting crude tert-butyl (3aR,5R,6S,7R,7aR)-5-((S)-1-(cyclopentylamino)ethyl)-6,7-bis(4-methoxybenzyloxy)-5,6,7,7a-tetrahydro-3aH-pyrano[3,2-d]thiazol-2-yl (methyl)carbamate in dichloromethane (10 mL) was treated with TFA (1 mL) overnight at room temperature. Removal of volatiles gave a residue, which was dissolved into methanol (5 mL) and neutralized with concentrated NH4OH (2 mL). After concentrated under reduced pressure, the crude product was purified by a silica gel column, eluted with 5%-20% methanol in dichloromethane to give a mixture of the above two compounds. Separation by Prep-HPLC with the following conditions [(Agilent 1200 prep HPLC): Column, SunFire Prep C18,19*50 mm 5um; mobile phase, WATER with 0.03% NH4OH and CH3CN (10% CH3CN up to 45% in 10 min); Detector, UV 220 nm.] gave (3aR,5R,6S,7R,7aR)-5-((R)-1-(cyclopentylamino)ethyl)-2-(methylamino)-5,6,7,7a-tetrahydro-3aH-pyrano[3,2-d]thiazole-6,7-diol as a white solid (5.7 mg, 5%, faster eluting isomer); (ES, m/z): [M+H]+ 316.0; 1H NMR (300 MHz, D2O) δ 6.56 (d, J=6.3 Hz, 1H), 4.20-4.15 (m, 1H), 3.98-3.88 (m, 2H), 3.67-3.53 (m, 3H), 2.92 (s, 3H), 2.00 (s, 2H), 1.66-1.51 (m, 6H), 1.24 (d, J=6.9 Hz, 3H); and (3aR,5R,6S,7R,7aR)-5-((S)-1-(cyclopentylamino)ethyl)-2-(methylamino)-5,6,7,7a-tetrahydro-3aH-pyrano[3,2-d]thiazole-6,7-diol as white solid (10.4 mg, 10%); (ES, m/z): [M+H]+ 316.0; 1H NMR (300 MHz, D2O) δ 6.48 (d, J=6.9 Hz, 1H), 4.38-4.34 (m, 1H), 4.05-4.04 (m, 1H), 3.75-3.49 (m, 4H), 2.94-2.92 (m, 3H), 1.99-1.98 (m, 2H), 1.65-1.42 (m, 6H), 1.32 (d, J=6.6 Hz, 3H).

Examples 14 & 15

(3aR,5R,6S,7R,7aR)-5-((S)-1-amino-2,2,2-trifluoro-
ethyl)-2-(dimethylamino)-5,6,7,7a-tetrahydro-3aH-
pyrano[3,2-d]thiazole-6,7-diol & (3aR,5R,6S,7R,
7aR)-5-((R)-1-amino-2,2,2-trifluoroethyl)-2-
(dimethylamino)-5,6,7,7a-tetrahydro-3aH-pyrano[3,
2-d]thiazole-6,7-diol

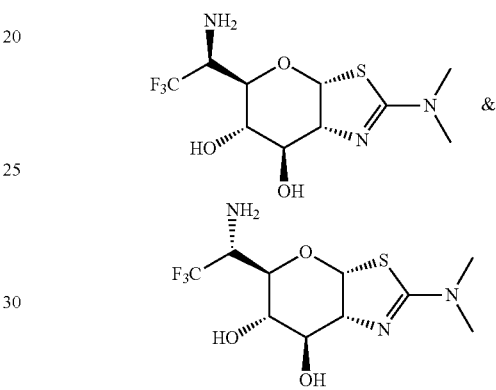

Scheme X

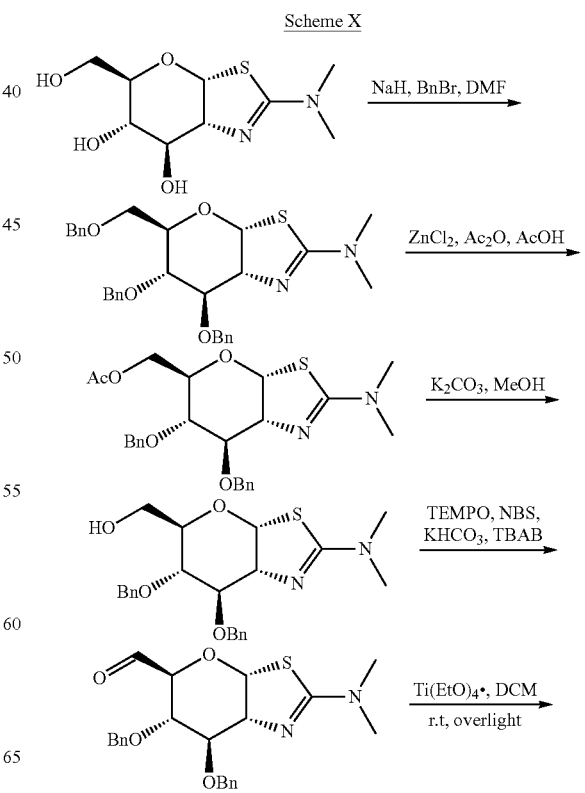

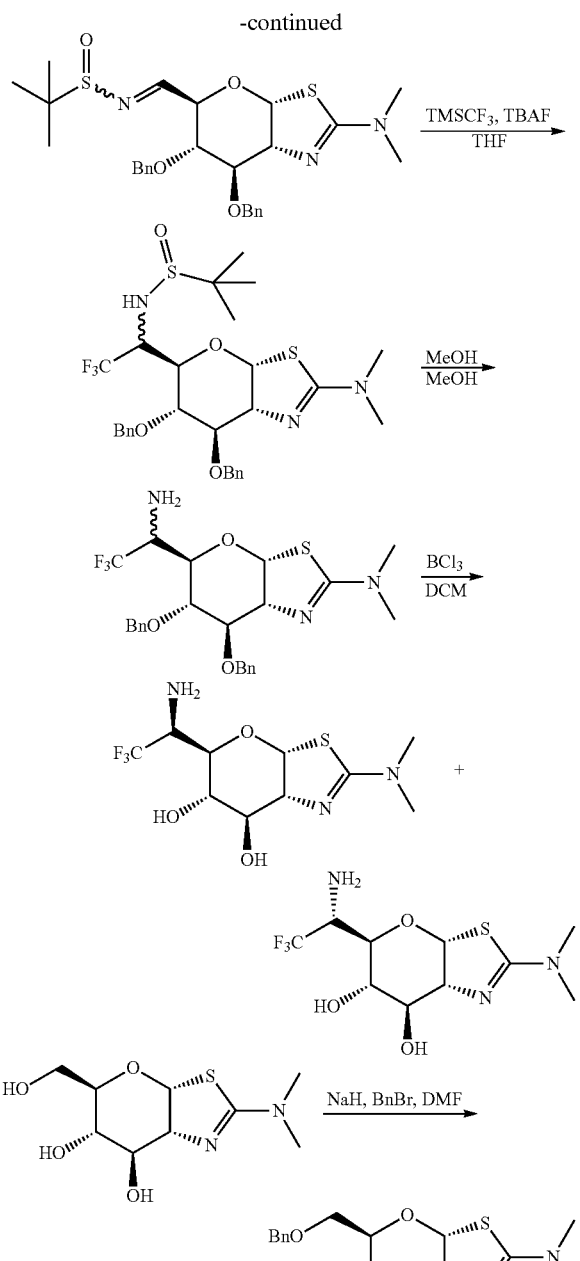

(3aR,5R,6S,7R,7aR)-6,7-bis(benzyloxy)-5-(benzyloxymethyl)-N,N-dimethyl-5,6,7,7a-tetrahydro-3aH-pyrano[3,2-d]thiazol-2-amine A solution of (3aR,5R,6S,7R,7aR)-2-(dimethylamino)-5-(hydroxymethyl)-5,6,7,7a-tetrahydro-3aH-pyrano[3,2-d]thiazole-6,7-diol (100 g, 0.4 mol) in DMF (600 mL) was treated with NaH (110 g, 3.2 mol, 70% dispersed by mineral oil) at 0° C. for 30 min, followed by the addition of BnBr (410 g, 2.4 mol) dropwise. After kept additional 2 hours at room temperature, the mixture was poured into ice-water (1.5 kg) slowly and extracted with ethyl acetate (3×500 mL). The organic layers were combined, washed with brine (3×300 mL), dried over anhydrous sodium sulfate and concentrated under reduced pressure to give a residue, which was purified by a silica gel column, eluted with 10%-30% ethyl acetate in petroleum ether to afford the title compound (166 g, 80%) as a yellow oil; (ES, m/z) [M+H]⁺ 519.0; ¹H NMR (300 MHz, CDCl₃) δ 7.26-7.48 (m, 15H), 6.40 (d, J=6.6 Hz, 1H), 4.54-4.86 (m, 6H), 4.41 (d, J=4.8 Hz, 1H), 4.17-4.18 (m, 1H), 3.60-3.79 (m, 4H), 3.12 (s, 6H).

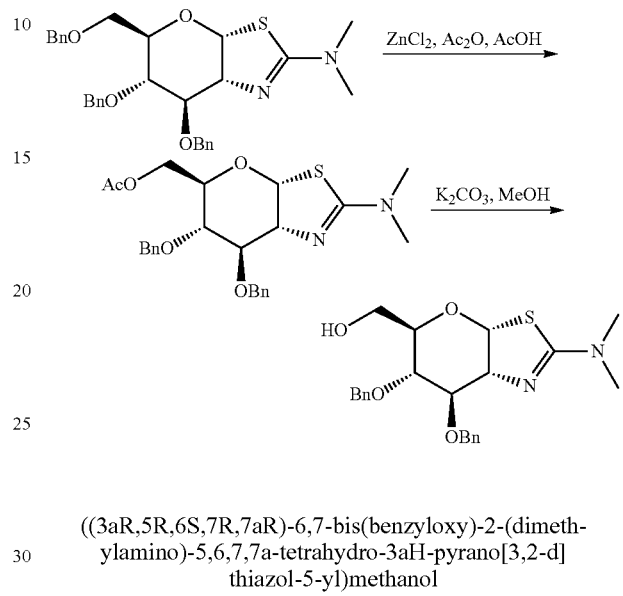

((3aR,5R,6S,7R,7aR)-6,7-bis(benzyloxy)-2-(dimethylamino)-5,6,7,7a-tetrahydro-3aH-pyrano[3,2-d]thiazol-5-yl)methanol To a solution of (3aR,5R,6S,7R,7aR)-6,7-bis(benzyloxy)-5-(benzyloxymethyl)-N,N-dimethyl-5,6,7,7a-tetrahydro-3aH-pyrano[3,2-d]thiazol-2-amine (166 g, 0.3 mol) in Ac₂O (1 L) and AcOH (100 mL) was added anhydrous ZnCl₂ (353 g, 2.6 mol) at 0° C. After kept additional 2 hours at room temperature, the reaction was poured into ice-cold H₂O (1.5 kg) slowly and extracted with dichloromethane (3×500 mL). The organic layers combined, washed with brine (3×200 mL) and dried over anhydrous sodium sulfate. After filtration, volatiles were distilled out by high vacuum to give the crude acetate (160 g, (ES, m/z) [M+H]⁺ 471.0) as a brown oil. A solution of the above crude acetate in methanol (1 L) was treated with K₂CO₃ (18 g, 0.13 mol) at 30° C. for 8 hours, after filtration, the solvent was distilled out under vacuum to give a residue, which was purified by a silica gel column with 20%-30% ethyl acetate in petroleum ether to afford the title compound (108 g, 79% 2 steps) as a yellow syrup; (ES, m/z) [M+H]⁺ 429.0; ¹H NMR (300 MHz, CDCl₃) δ 7.26-7.43 (m, 10H), 6.29 (d, J=6.6 Hz, 1H), 4.54-4.81 (m, 4H), 4.41 (d, J=4.8 Hz, 1H), 4.17-4.18 (m, 1H), 3.57-3.79 (m, 4H), 3.02 (s, 6H).

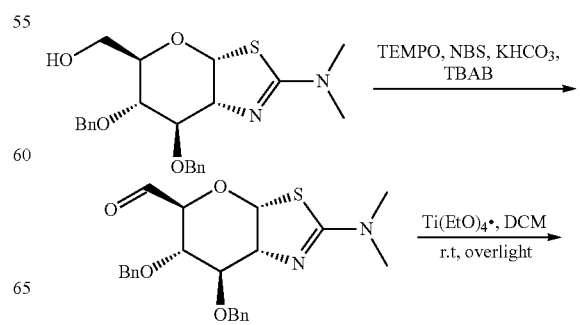

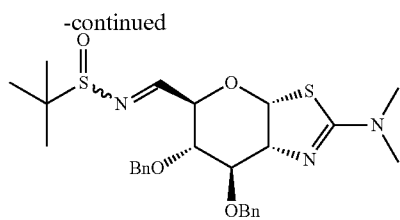

N-(((3aR,5R,6S,7R,7aR)-6,7-bis(benzyloxy)-2-(dimethylamino)-5,6,7,7a-tetrahydro-3aH-pyrano[3,2-d]thiazol-5-yl)methylene)-2-methylpropane-2-sulfinamide To a vigorous stirred mixture of ((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (1.5 g, 3.5 mmol), TEMPO (24 mg, 0.15 mmol), KHCO$_3$ (1.4 g, 13.8 mmol) and TBAB (50 mg, 0.16 mmol) in dichloromethane (50 mL) and H$_2$O (20 mL) was added NBS (654 mg, 3.7 mmol) at 0° C. The resulting mixture was stirred at room temperature for 1 hour, quenched by Na$_2$SO$_3$ (500 mg, 4.0 mmol), and extracted with dichloromethane (2×50 mL). The combined organic layer was dried over anhydrous magnesium sulfate, and concentrated under vacuum to give the crude aldehyde, which was treated with 2-methylpropane-2-sulfinamide (450 mg, 3.6 mmol) and Ti(OEt)$_4$ (1.5 g, 6.6 mmol) in dichloromethane (50 mL). After stirred overnight at room temperature, the resulting solution was concentrated under vacuum to give a residue, which was purified by a silica gel column, eluted with 20% ethyl acetate in petroleum ether to give the product as yellow oil (1.16 g, 63%, E/Z=1:1 determined by $^1$H NMR). (ES, m/z) [M+H]$^+$ 530.0; $^1$H NMR (300 MHz, CDCl$_3$) δ 8.09-8.07 (m, 1H), 7.55-7.21 (m, 10H), 6.23-6.21 (m, 1H), 4.79-4.61 (m, 4H), 4.55-4.23 (m, 3H), 3.89-3.87 (m, 1H), 3.03 (s, 6H), 1.19 (s, 9H)

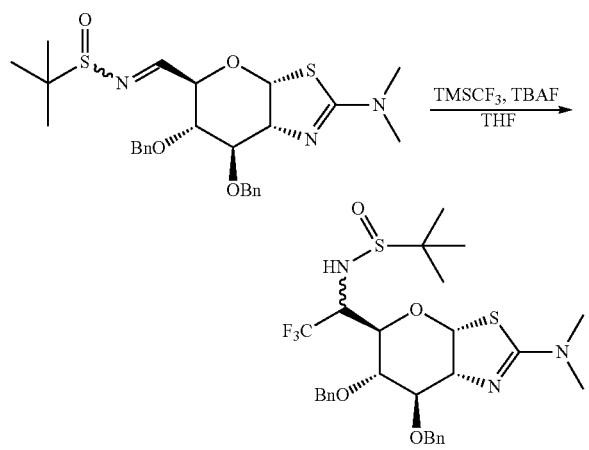

N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)-2,2,2-trifluoroethyl)-2-methylpropane-2-sulfinamide A mixture of TBAF (173 mg, 0.7 mmol) and 4 Å Molecular sieves (500 mg) in THF (50 mL) was stirred for 30 min at −20° C., and followed by addition of a solution of N-(((3aR,5R,6S,7R,7aR)-6,7-bis(benzyloxy)-2-(dimethylamino)-5,6,7,7a-tetrahydro-3aH-pyrano[3,2-d]thiazol-5-yl)methylene)-2-methylpropane-2-sulfinamide (700 mg, 1.3 mmol) and TMSCF$_3$ (939 mg, 6.6 mmol) in THF (30 mL). The resulting mixture was stirred for 2 hours at room temperature, quenched with water (120 mL), and extracted with ethyl acetate (4×50 mL). The combined organic layer was washed with brine (2×50 mL), dried over anhydrous magnesium sulfate, and concentrated under vacuum to give a residue, which was purified by a silica gel column, eluted with 20%-30% ethyl acetate in petroleum ether to give the title compound (300 mg, 38%, two isomers, 1:1 by $^1$H NMR) as yellow oil. (ES, m/z) [M+H]$^+$ 600.0; $^1$H NMR (300 MHz, CDCl$_3$) δ 7.21-7.55 (m, 10H), 6.25-6.27 (m, 1H), 4.58-4.82 (m, 4H), 4.30-4.34 (m, 3H), 3.89-3.98 (m, 2H), 3.03 (s, 6H), 1.18 (s, 9H).

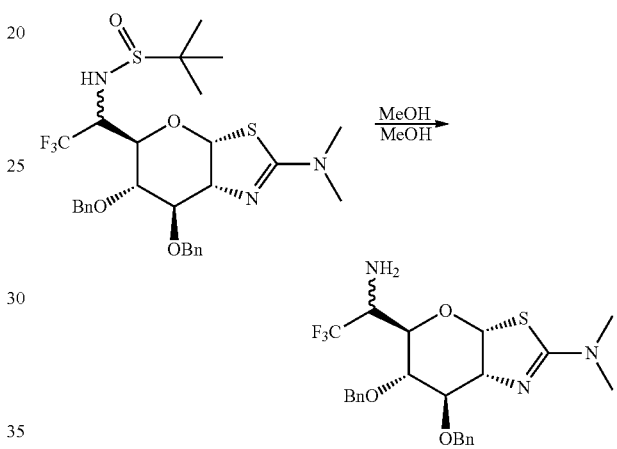

(3aR,5R,6S,7R,7aR)-5-(1-amino-2,2,2-trifluoroethyl)-6,7-bis(benzyloxy)-N,N-dimethyl-5,6,7,7a-tetrahydro-3aH-pyrano[3,2-d]thiazol-2-amine To a solution of N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)-2,2,2-trifluoroethyl)-2-methylpropane-2-sulfinamide (300 mg, 0.5 mmol) in methanol (10 mL) was added acetyl chloride (5 mL). After stirred for 2 hours at room temperature, the resulting solution was poured into saturated aqueous NaHCO$_3$ solution (50 mL) and extracted with dichloromethane (3×50 mL). The combined organic layer was washed with brine (30 mL), dried over magnesium sulfate and concentrated under vacuum to give the product as light yellow syrup (210 mg, 85%). (ES, m/z): [M+H]$^+$ 496.0. $^1$H NMR (300 MHz, CDCl$_3$) δ 7.55-7.21 (m, 10H), 6.28-6.26 (m, 1H), 4.79-4.53 (m, 4H), 4.34-4.31 (m, 3H), 3.90-3.78 (m, 2H), 3.02 (s, 6H)

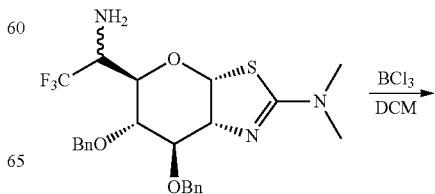

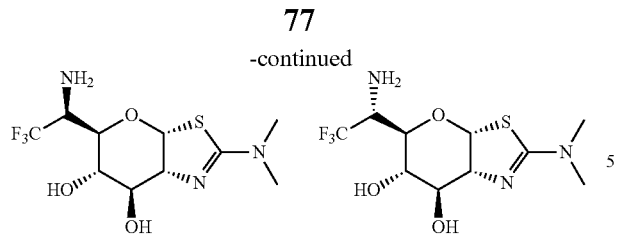

(3aR,5R,6S,7R,7aR)-5-((S)-1-amino-2,2,2-trifluoro-ethyl)-2-(dimethylamino)-5,6,7,7a-tetrahydro-3aH-pyrano[3,2-d]thiazole-6,7-diol & (3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol A solution of (3aR,5R,6S,7R,7aR)-5-(1-amino-2,2,2-trifluoroethyl)-6,7-bis(benzyloxy)-N,N-dimethyl-5,6,7,7a-tetrahydro-3aH-pyrano[3,2-d]thiazol-2-amine (280 mg, 0.05 mmol) in dichloromethane (10 mL) was treated with $BCl_3$ (2 mL, 2 mmol, 1M in dichloromethane) for 30 min at 0° C. The reaction was quenched by methanol (5 mL). Removal of volatiles gave a residue, which was dissolved into methanol (5 mL) and neutralized with concentrated $NH_4OH$ (2 mL). After concentrated under reduced pressure, the crude product was purified by a silica gel column, eluted with 5%-20% methanol in dichloromethane to give a mixture of the above two compounds. Separation by Prep-HPLC with the following conditions (Agilent 1200 prep HPLC): Column, X-Bridge C18; mobile phase, 50 mmol/L $NH_4HCO_3$ in water with 0.05% $NH_4OH$ and $CH_3CN$ (15% up to 28% in 7 mins); Detector, 220 nm) gave (3aR,5R,6S,7R,7aR)-5-((S)-1-amino-2,2,2-trifluoroethyl)-2-(dimethylamino)-5,6,7,7a-tetrahydro-3aH-pyrano[3,2-d]thiazole-6,7-diol as a white solid (50.7 mg, 28%, Faster eluting isomer); (ES, m/z): [M+H]$^+$ 315.9; $^1$H NMR (300 MHz, $D_2O$) δ 6.23 (d, J=6.6 Hz, 1H), 4.19 (t, J=5.7 Hz, 1H), 3.97 (t, J=4.5 Hz, 1H), 3.83 (dd, J=4.5 Hz, 4.2 Hz, 1H), 3.71-3.65 (m, 1H), 3.55-3.60 (m, 1H), 2.93 (s, 6H); and (3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol as a white solid (56.5 mg, 32%, Slower eluting isomer); (ES, m/z) [M+H]$^+$ 315.9; $^1$H NMR (300 MHz, $D_2O$) δ 6.24 (d, J=6.3 Hz, 1H), 4.15-4.05 (m, 1H), 3.98-3.92 (m, 1H), 3.82-3.74 (m, 1H), 3.58-3.50 (m, 1H), 3.49-3.42 (m, 1H), 2.88 (s, 6H)

Examples 16 & 17

(3aR,5R,6S,7R,7aR)-2-(dimethylamino)-5-((R)-2,2,2-trifluoro-1-(methylamino)ethyl)-5,6,7,7a-tetrahydro-3aH-pyrano[3,2-d]thiazole-6,7-diol & (3aR,5R,6S,7R,7aR)-2-(dimethylamino)-5-((R)-1-(dimethylamino)-2,2,2-trifluoroethyl)-5,6,7,7a-tetrahydro-3aH-pyrano[3,2-d]thiazole-6,7-diol

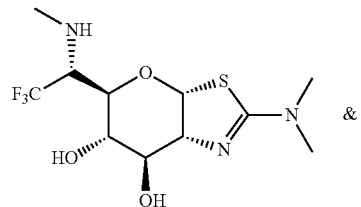

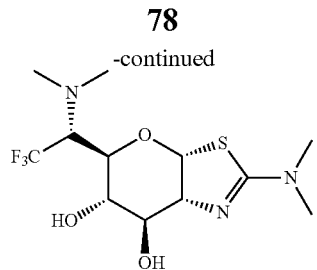

Scheme XI

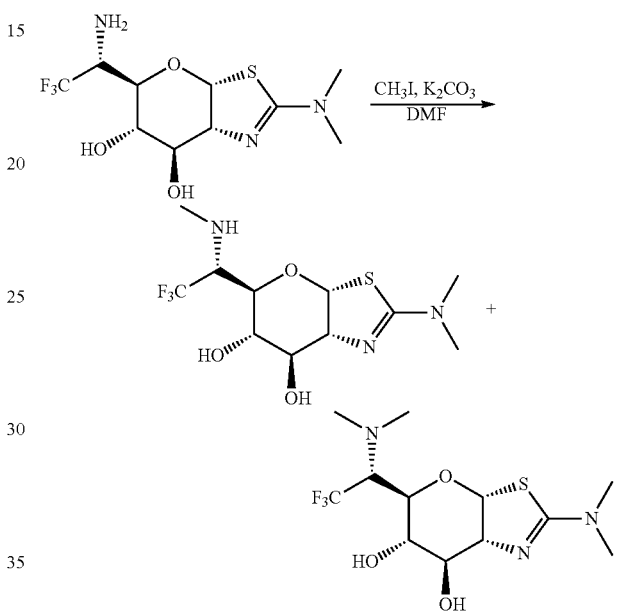

(3aR,5R,6S,7R,7aR)-2-(dimethylamino)-5-((R)-2,2,2-trifluoro-1-(methylamino)ethyl)-5,6,7,7a-tetrahydro-3aH-pyrano[3,2-d]thiazole-6,7-diol & (3aR,5R,6S,7R,7aR)-2-(dimethylamino)-5-((R)-1-(dimethylamino)-2,2,2-trifluoroethyl)-5,6,7,7a-tetrahydro-3aH-pyrano[3,2-d]thiazole-6,7-diol A mixture of (3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol (50 mg, 0.16 mmol) and potassium carbonate (125 mg, 0.9 mmol) in DMF (6 mL) was treated with $CH_3I$ (258 mg, 1.8 mmol) for overnight at room temperature. The reaction was then quenched by dimethylamine (2 mL, 4 mmol, 2M in THF). Removal of volatiles gave a residue, which was dissolved into methanol (50 mL) and filtered through a short silica gel column to get a mixture of the above two compounds. Separation by Prep-HPLC with the following conditions: (Agilent 1200 Prep-HPLC): Column, X-Bridge Prep C18, 19*150 mm; mobile phase, water and $CH_3CN$ (15%-45% in 10 mins); Detector, UV 200 nm) gave (3aR,5R,6S,7R,7aR)-2-(dimethylamino)-5-((R)-2,2,2-trifluoro-1-(methylamino)ethyl)-5,6,7,7a-tetrahydro-3aH-pyrano[3,2-d]thiazole-6,7-diol as a white solid (10.2 mg, 20%). (ES, m/z) [M+H]$^+$ 330.0; $^1$H NMR (300 MHz, $D_2O$) δ 6.26 (d, J=6.6 Hz, 1H), 4.09-4.07 (m, 1H), 3.95-3.91 (m, 1H), 3.86-3.83 (m, 1H), 3.71-3.67 (m, 1H), 3.42-3.34 (m, 1H), 2.92 (s, 6H), 2.44 (s, 3H); and (3aR,5R,6S,7R,7aR)-2-(dimethylamino)-5-((R)-1-(dimethylamino)-2,2,2-trifluoroethyl)-5,6,7,7a-tetrahydro-3aH-pyrano[3,2-d]thiazole-6,7-diol as a white solid (15.9 mg, 29%). (ES, m/z) [M+H]+ 344.0; 1H NMR (300 MHz, D2O) δ 6.22 (d, J=6.6 Hz, 1H), 4.17-4.13 (m, 1H), 3.98-3.95 (m, 1H), 3.79-3.73 (m, 2H), 3.52-3.41 (m, 1H), 2.89 (s, 6H), 2.42 (s, 6H).
Examples 18 & 19
(3aR,5R,6S,7R,7aR)-5-((R)-1-aminoethyl)-2-(dimethylamino)-5,6,7,7a-tetrahydro-3aH-pyrano[3,2-d]thiazole-6,7-diol & (3aR,5R,6S,7R,7aR)-5-((S)-1-aminoethyl)-2-(dimethylamino)-5,6,7,7a-tetrahydro-3aH-pyrano[3,2-d]thiazole-6,7-diol
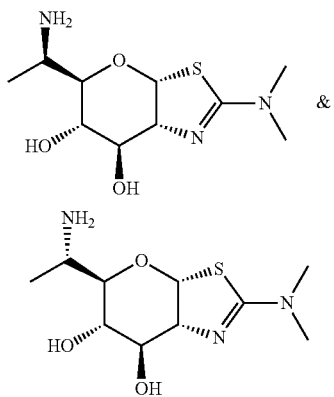
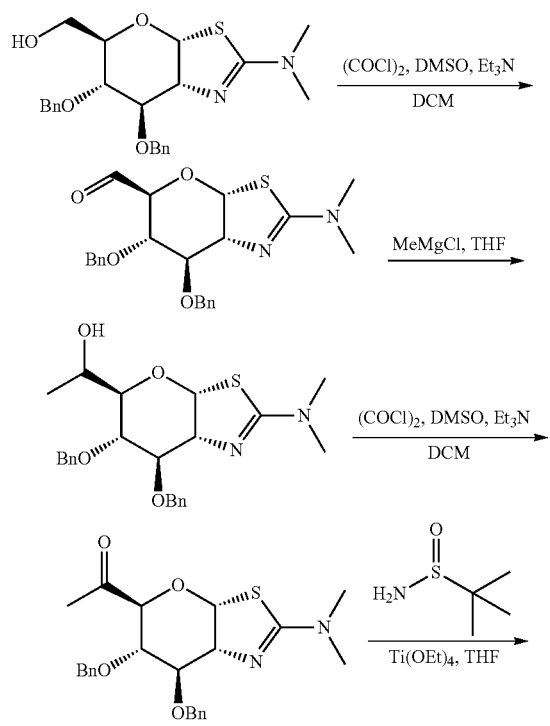
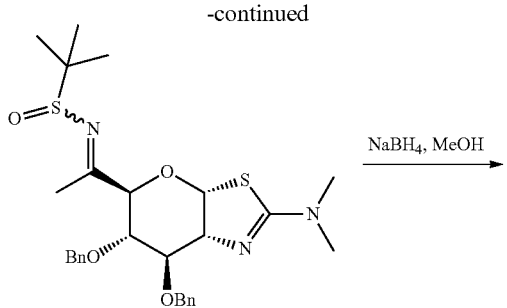
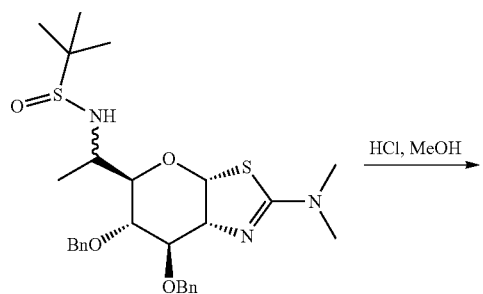
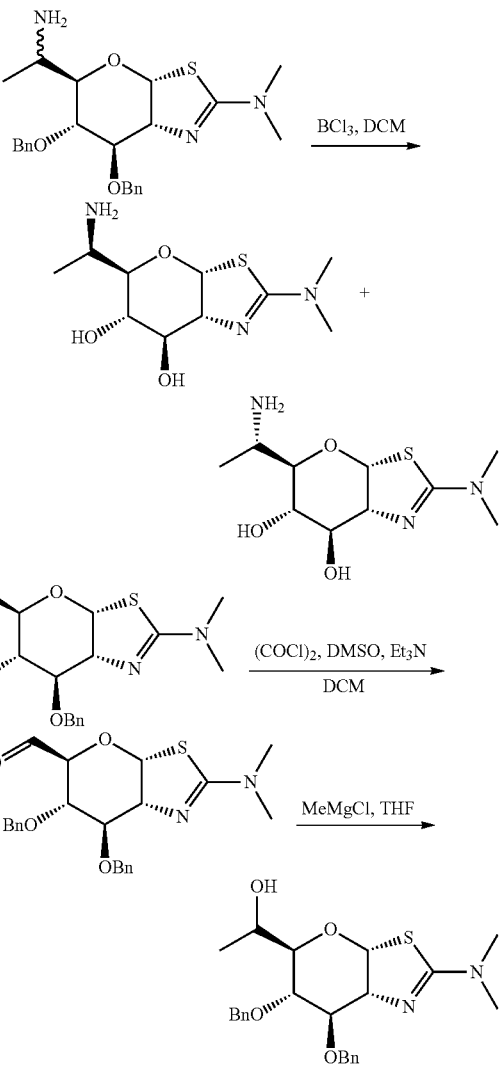

(S)-1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethanol A solution of DMSO (51.1 g, 0.66 mol) in anhydrous dichloromethane (800 mL) was treated with oxalyl dichloride (61.7 g, 0.49 mol) at −78° C. for 1 hour, and followed by addition of ((3aR,5R,6S,7R,7aR)-6,7-bis(benzyloxy)-2-(dimethylamino)-5,6,7,7a-tetrahydro-3aH-pyrano[3,2-d]thiazol-5-yl)methanol (35 g, 82 mmol) in anhydrous dichloromethane (200 mL). The resulting solution was stirred for 4 hours at −30° C., and followed by addition of triethylamine (99.2 g, 0.98 mol) at −78° C. After 1 hour at −30° C., the reaction was quenched by H$_2$O (800 mL), and extracted with dichloromethane (3×300 mL). The combined organic layer was washed with brine (3×200 mL), dried over anhydrous sodium sulfate and concentrated under vacuum to afford crude aldehyde, which was treated with methylmagnesium chloride (68 mL, 204 mmol, 3M in THF) in THF (600 mL) at 0° C. After 5 hours at 20° C., the reaction was quenched by saturated aqueous NH$_4$Cl solution (400 mL) and extracted with ethyl acetate (4×300 mL). The combined organic layer was washed with brine (3×200 mL), dried over anhydrous sodium sulfate and concentrated under vacuum. The crude residue was purified by a silica gel column, eluted with 5%-40% ethyl acetate in petroleum ether to afford the title compound (19.6 g, 54%, two isomers, the ratio was 1:4 by $^1$HNMR) as a light yellow syrup. (ES, m/z): [M+H]$^+$ 443.0; $^1$H NMR (300 MHz, CDCl$_3$) δ 7.41-7.30 (m, 10H), 6.35-6.32 (m, 1H), 4.80-4.65 (m, 4H), 4.42-4.15 (m, 2H), 3.89-3.77 (m, 2H), 3.39-3.35 (m, 1H), 3.00 (s, 6H), 1.26-1.20 (m, 3H).

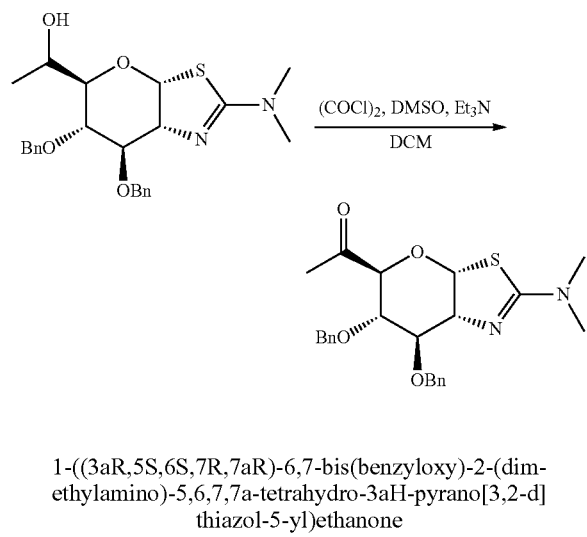

1-((3aR,5S,6S,7R,7aR)-6,7-bis(benzyloxy)-2-(dimethylamino)-5,6,7,7a-tetrahydro-3aH-pyrano[3,2-d]thiazol-5-yl)ethanone A solution of DMSO (25.4 g, 325 mmol) in anhydrous dichloromethane (400 mL) was treated with oxalyl dichloride (30.8 g, 244 mmol) at −78° C. for 1 hour, and followed by addition of (S)-1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethanol (18 g, 40 mmol) in anhydrous dichloromethane (100 mL). The resulting solution was stirred for 4 hours at −50° C. and then treated with triethylamine (49.3 g, 488 mmol) at −78° C. After 1 hour at −30° C., the reaction was quenched by H$_2$O (500 mL) and extracted with dichloromethane (3×200 mL). The combined organic layer was washed with brine (3×150 mL), dried over anhydrous sodium sulfate and concentrated under vacuum. The crude residue was purified by a silica gel column, eluted with 5%-30% ethyl acetate in petroleum ether to afford the title compound (11.3 g, 63%) as a light yellow syrup. (ES, m/z) [M+H]$^+$ 441.0; $^1$H NMR (300 MHz, CDCl$_3$) δ 7.44-7.31 (m, 10H), 6.29 (d, J=6.3 Hz, 1H), 4.81-4.55 (m, 4H), 4.35-4.17 (m, 2H), 4.18-3.99 (m, 2H), 3.12 (s, 3H), 3.11 (s, 3H), 2.15 (s, 3H).

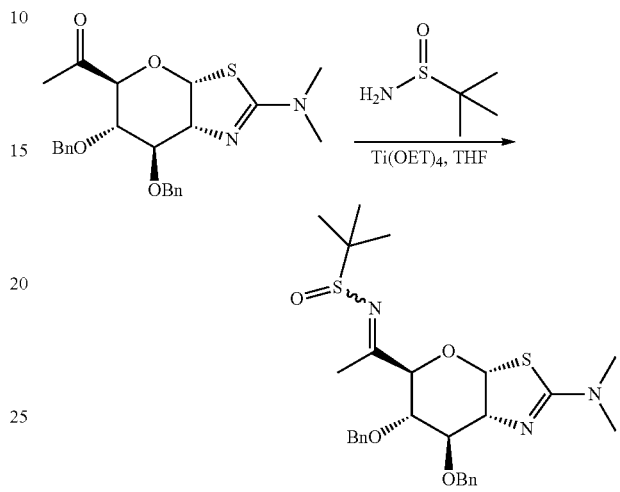

N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethylidene)-2-methylpropane-2-sulfinamide To a solution of 1-((3aR,5S,6S,7R,7aR)-6,7-bis(benzyloxy)-2-(dimethylamino)-5,6,7,7a-tetrahydro-3aH-pyrano[3,2-d]thiazol-5-yl)ethanone (1.4 g, 3.2 mmol) in THF (60 mL) was added Ti(OEt)$_4$ (1.8 g, 7.9 mmol) and 2-methylpropane-2-sulfinamide (760 mg, 6.3 mmol). After stirred for 12 hours at 60° C., the reaction was quenched by water (60 mL), and extracted with ethyl acetate (3×100 mL). The combined organic layer was washed with brine (3×70 mL), dried over anhydrous sodium sulfate and concentrated under vacuum. The crude residue was purified by a silica gel column, eluted with 3%-10% ethyl acetate in petroleum ether to afford the title compound (1.1 g, 64%, E/Z=1:1 determined by $^1$H NMR) as a light yellow syrup. (ES, m/z) [M+H]$^+$ 544.0; $^1$H NMR (300 MHz, CDCl$_3$) δ 7.42-7.29 (m, 10H), 6.39-6.28 (m, 1H), 4.80-4.58 (m, 4H), 4.55-4.19 (m, 2H), 4.18-4.04 (m, 2H), 3.10 (s, 3H), 3.08 (s, 3H), 2.35-2.33 (m, 3H), 1.36-1.30 (m, 9H).

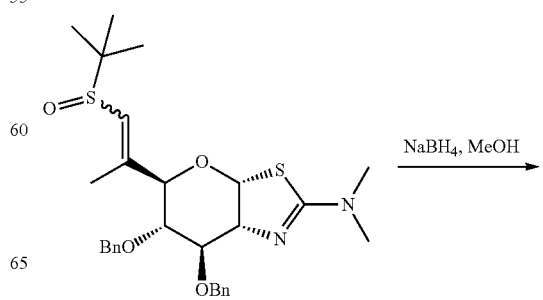

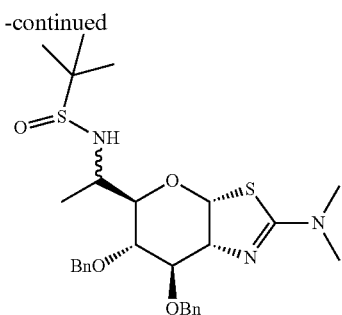

N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethyl)-2-methylpropane-2-sulfinamide To a solution of N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethylidene)-2-methylpropane-2-sulfinamide (900 mg, 1.7 mmol) in methanol (20 mL) was added NaBH₄ (129 mg, 3.4 mmol). After additional 1 hour at 25° C., the reaction was quenched by water (30 mL) and extracted with ethyl acetate (3×40 mL). The combined organic layer was dried over anhydrous sodium sulfate and concentrated under vacuum. The residue was purified by a silica gel column, eluted with 5%-15% ethyl acetate in petroleum ether to afford the title compound (785 mg, 87%, two isomers, the ratio was 2:3 by ¹HNMR) as a light yellow syrup. (ES, m/z) [M+H]⁺ 546.0; ¹H NMR (300 MHz, CDCl₃) δ 7.43-7.29 (m, 10H), 6.32-6.27 (m, 1H), 4.77-4.61 (m, 4H), 4.42-4.18 (m, 2H), 3.83-3.73 (m, 1H), 3.63-3.59 (m, 1H), 3.42-3.37 (m, 1H), 3.04 (s, 3H), 3.00 (s, 3H), 1.39-1.30 (m, 9H), 1.17-1.15 (m, 3H).

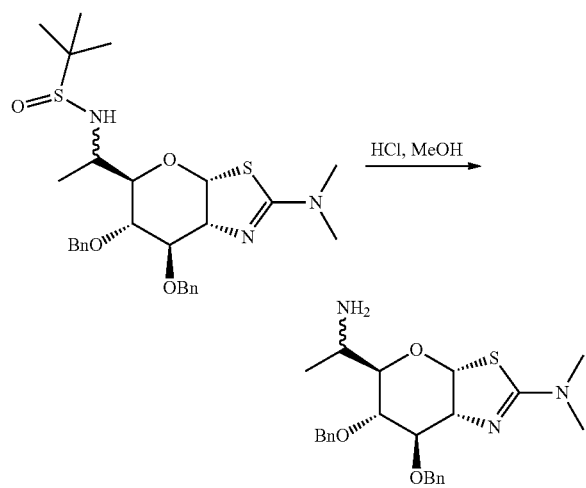

(3aR,5R,6S,7R,7aR)-5-(1-aminoethyl)-6,7-bis(benzyloxy)-N,N-dimethyl-5,6,7,7a-tetrahydro-3aH-pyrano[3,2-d]thiazol-2-amine A solution of N-(1-((3aR,5R,6S,7R,7aR)-6,7-bis(benzyloxy)-2-(dimethylamino)-5,6,7,7a-tetrahydro-3aH-pyrano[3,2-d]thiazol-5-yl)ethyl)-2-methylpropane-2-sulfinamide (685 mg, 1.3 mmol) in methanol was bubbled with dry hydrogen chloride gas for 10 mins at 0° C. After additional 2 hours at room temperature, volatiles were distilled out to give a residue, which was dissolved into methanol (10 mL) and neutralized with concentrated NH₄OH (3 mL). After concentrated under vacuum, the residue was purified by a silica gel column, eluted with 20%-50% ethyl acetate in petroleum ether to afford the title compound (416 mg, 75%, two isomers, the ratio was 2:3 by ¹HNMR) as a light yellow syrup. (ES, m/z) [M+H]⁺ 442.0; ¹H NMR (300 MHz, CDCl₃) δ 7.44-7.31 (m, 10H), 6.33-6.30 (m, 1H), 4.81-4.62 (m, 4H), 4.58-4.26 (m, 2H), 3.70-3.65 (m, 1H), 3.47-3.45 (m, 1H), 3.31-3.28 (m, 1H), 3.11 (s, 3H), 3.10 (s, 3H), 1.15 (d, J=5.7 Hz, 1.2H), 0.99 (d, J=5.7 Hz, 1.8H).

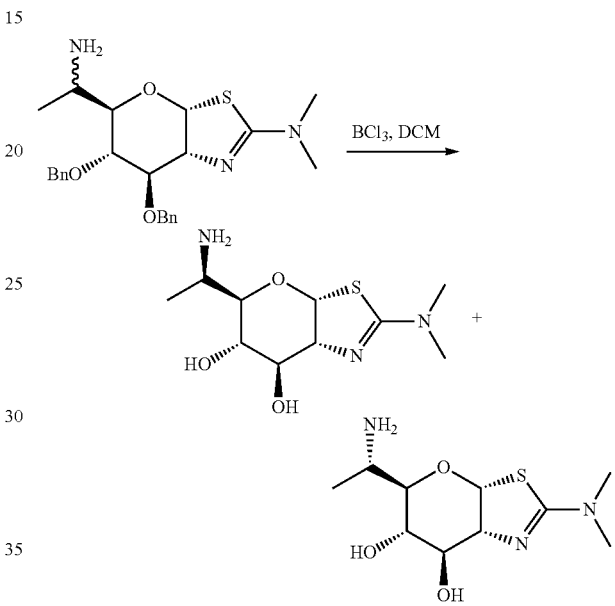

(3aR,5R,6S,7R,7aR)-5-((R)-1-aminoethyl)-2-(dimethylamino)-5,6,7,7a-tetrahydro-3aH-pyrano[3,2-d]thiazole-6,7-diol & (3aR,5R,6S,7R,7aR)-5-((S)-1-aminoethyl)-2-(dimethylamino)-5,6,7,7a-tetrahydro-3aH-pyrano[3,2-d]thiazole-6,7-diol A solution of (3aR,5R,6S,7R,7aR)-5-(1-aminoethyl)-6,7-bis(benzyloxy)-N,N-dimethyl-5,6,7,7a-tetrahydro-3aH-pyrano[3,2-d]thiazol-2-amine (350 mg, 0.8 mmol) in dichloromethane (30 mL) was treated with BCl₃ in dichloromethane (8 mL, 8 mmol, 1M in dichloromethane) for 2 hours at −78° C. The reaction was quenched by methanol (30 mL). Removal of volatiles gave a residue, which was dissolved into methanol (10 mL) and neutralized with concentrated NH₄OH (4 mL). After concentrated under reduced pressure, the crude product was purified by a silica gel column, eluted with 5%-20% methanol in dichloromethane to give a mixture of the above two compounds. Separation by Prep-HPLC with the following conditions (Agilent Prep 1200 Detecl): Column, SunFire Prep C18; mobile phase, Water with 0.05% ammonia and CH₃CN (10% up to 30% in 10 mins); Detector, 220 nm) gave (3aR,5R,6S,7R,7aR)-5-((R)-1-aminoethyl)-2-(dimethylamino)-5,6,7,7a-tetrahydro-3aH-pyrano[3,2-d]thiazole-6,7-diol as a white solid: (31.9 mg, 15%, faster eluting isomer); (ES, m/z): [M+H]⁺ 262.0; ¹HNMR (300 MHz, D₂O) δ 6.19 (d, J=6.6 Hz, 1H), 4.22 (t, J=5.4 Hz, 1H), 4.02-4.05 (m, 1H), 3.58-3.62 (m, 1H), 3.21-3.25 (m, 1H), 3.03-3.19 (m, 1H), 2.99 (s, 6H), 1.09 (d, J=6.6 Hz, 3H); and (3aR,5R,6S,7R,7aR)-5-((S)-1-aminoethyl)-2-(dimethylamino)-5,6,7,7a-tetrahydro-3aH-pyrano[3,2-d]thiazole-6,7-diol as a white solid (49.3 mg, 24%, slower eluting isomer); (ES, m/z): [M+H]+ 262.0; ¹HNMR (300 MHz, D₂O) δ 6.25 (d, J=6.6 Hz, 1H), 4.13 (t, J=5.4 Hz, 1H), 3.92-4.08 (m, 1H), 3.55-3.61 (m, 2H), 3.37-3.42 (m, 1H), 2.99 (s, 6H), 1.11 (d, J=6.9 Hz, 3H).

Example 20

(3aR,5S,6S,7R,7aR)-5-((R)-1-(4-(allyloxy)benzyloxy)-2,2,2-trifluoroethyl)-2-(dimethylamino)-5,6,7,7a-tetrahydro-3aH-pyrano[3,2-d]thiazole-6,7-diol

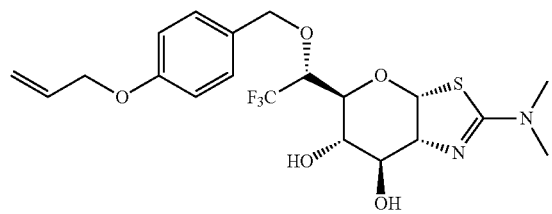 [SMILES: C=CCOc1ccc(CO[C@H]([C@H]2O[C@@H]3SC(N(C)C)=N[C@@H]3[C@@H](O)[C@@H]2O)C(F)(F)F)cc1]

Scheme XIII

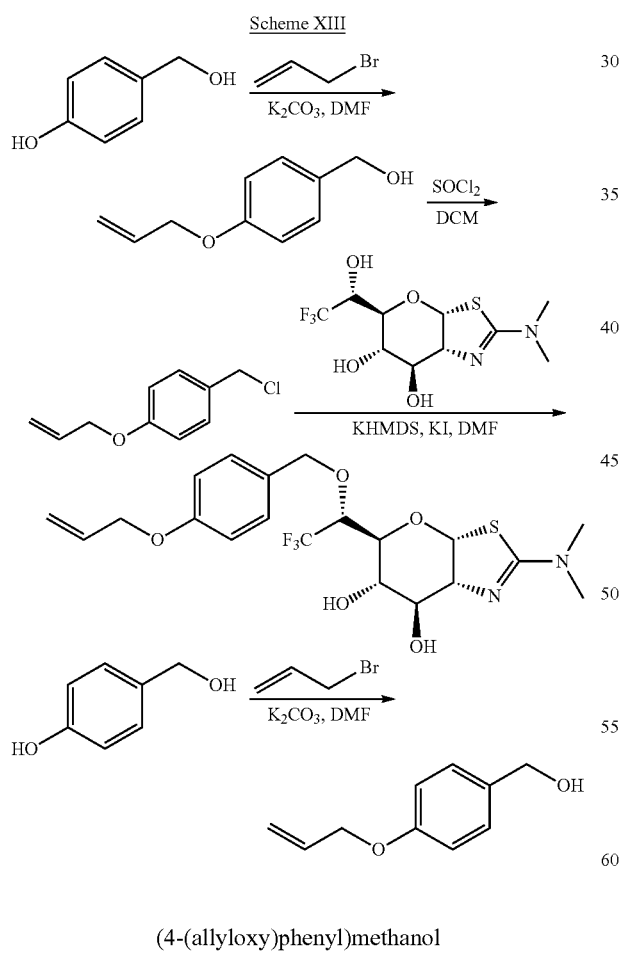

(4-(allyloxy)phenyl)methanol

To a solution of 4-(hydroxymethyl)phenol (5 g, 40 mmol) in DMF (50 mL) was added potassium carbonate (7.5 g, 54 mmol) and 3-bromoprop-1-ene (5 g, 41 mmol). The resulting solution was stirred overnight at 25° C., then quenched by the addition of water (200 mL) and extracted with ethyl acetate (3×100 mL). The combined organic layer was washed with brine (3×50 mL), dried over anhydrous magnesium sulfate and concentrated under vacuum to give a residue, which was purified by a silica gel column, eluted with 5%-10% ethyl acetate in petroleum ether to give the title compound as light yellow oil (4.5 g, 68%). (ES, m/z) [M+H]+: 165.0; ¹H NMR (300 MHz, CD₃OD) δ 7.29 (d, J=4.8 Hz, 2H), 6.92 (d, J=4.8 Hz, 2H), 6.13-6.05 (m, 1H), 5.44-5.37 (m, 1H), 5.27-5.22 (m, 1H), 4.54 (s, 2H), 4.49-4.46 (m, 2H).

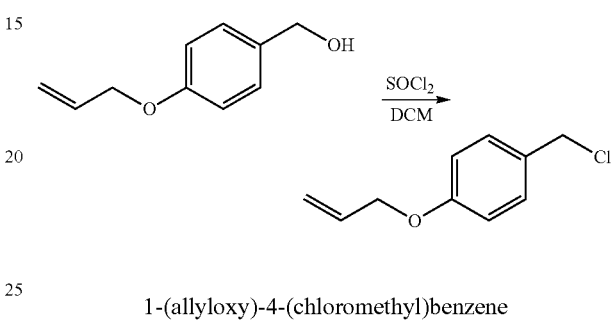

1-(allyloxy)-4-(chloromethyl)benzene

A solution of (4-(allyloxy)phenyl)methanol (4 g, 24 mmol) in dichloromethane (20 mL) was treated with SOCl₂ (6 g, 50 mmol) for 30 min at room temperature. Volatiles were distilled out to give a residue, which was purified by a silica gel column, eluted with 1%-5% ethyl acetate in petroleum ether to give 2 as light yellow oil (2 g, 45%). ¹H NMR (300 MHz, CDCl₃) δ 7.34 (d, J=4.8 Hz, 2H), 6.91 (d, J=4.8 Hz, 2H), 6.14-6.02 (m, 1H), 5.48-5.41 (m, 1H), 5.35-5.30 (m, 1H), 4.59 (s, 2H), 4.56-4.54 (m, 2H).

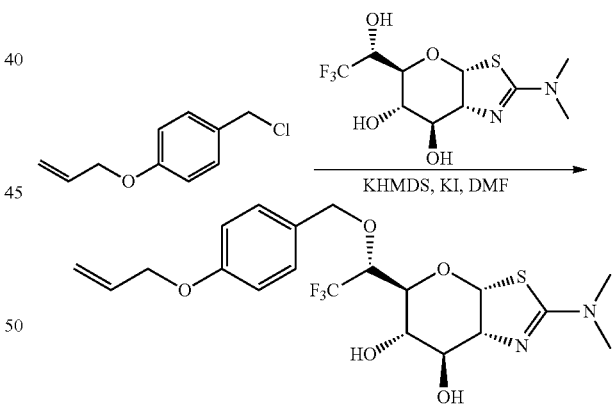

(3aR,5S,6S,7R,7aR)-5-((R)-1-(4-(allyloxy)benzyloxy)-2,2,2-trifluoroethyl)-2-(dimethylamino)-5,6,7,7a-tetrahydro-3aH-pyrano[3,2-d]thiazole-6,7-diol A solution of (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol (100 mg, 0.3 mmol) in DMF (5 mL) was treated with 1N solution of KHMDS (0.33 ml, 0.33 mmol) in THF at 0° C. for 30 min, followed by the addition of 1-(allyloxy)-4-(chloromethyl)benzene (144 mg, 0.79 mmol) and KI (26.6 mg, 0.16 mmol). After additional 1 hour at room temperature, the reaction was quenched by the addition of water (1 mL) and concentrated. The crude residue filtered through a short silica gel column and purified by Prep-HPLC with the following conditions: [(Agilent 1200 Prep-HPLC): Column, X-Bridge Prep C18, 19*150 mm; mobile phase, water with 0.05% $NH_4H_2O$ and $CH_3CN$ (30%-60% in 8 min); Detector, UV 200 nm] to give the title compound as a white solid (50 mg, 33%). (ES, m/z) [M+H]$^+$: 463.1; $^1$H NMR (300 MHz, CDCl$_3$) δ 7.31 (d, J=6.6 Hz, 2H), 6.92 (d, J=6.6 Hz, 2H), 6.37 (d, J=6.6 Hz, 1H), 6.15-6.02 (m, 1H), 5.48-5.40 (m, 1H), 5.33-5.29 (m, 1H), 4.90-4.86 (m, 1H), 4.65-4.61 (m, 1H), 4.57-4.55 (m, 2H), 4.29-4.25 (m, 1H), 4.17-4.15 (m, 1H), 4.08-4.06 (m, 1H), 3.96-3.93 (m, 1H), 3.79-3.77 (m, 1H), 3.16 (s, 6H).

Example 21

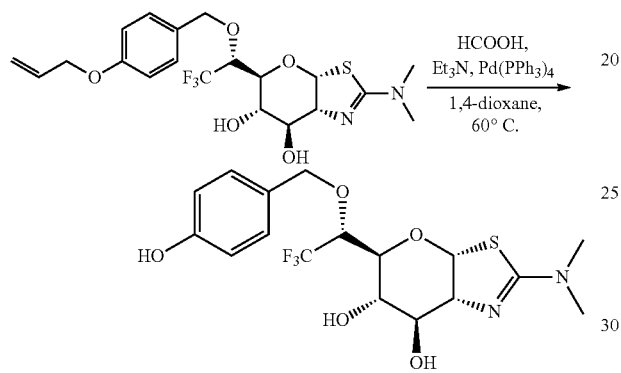

(3aR,5S,6S,7R,7aR)-5-((R)-1-(4-hydroxybenzyloxy)-2,2,2-trifluoroethyl)-2-(dimethylamino)-5,6,7,7a-tetrahydro-3aH-pyrano[3,2-d]thiazole-6,7-diol To a solution of (3aR,5S,6S,7R,7aR)-5-((R)-1-(4-(allyloxy)benzyloxy)-2,2,2-trifluoroethyl)-2-(dimethylamino)-5,6,7,7a-tetrahydro-3aH-pyrano[3,2-d]thiazole-6,7-diol (300 mg, 0.65 mmol) in 1,4-dioxane (50 mL) was added HCOOH (35.8 mg, 0.78 mmol), triethylamine (163 mg, 1.6 mmol) and Pd(PPh$_3$)$_4$ (75 mg, 0.06 mmol) at 0° C. under nitrogen atmosphere. After kept for 20 min at 60° C., additional HCOOH (358 mg, 7.8 mmol) was added. The resulting solution was stirred for another 1 h at 60° C. and then cooled to room temperature. Volatiles were distilled out to give a residue, which was purified by a silica gel column, eluted with 1%-3% methanol in dichloromethane to give (3aR,5S,6S,7R,7aR)-5-((R)-1-(4-hydroxybenzyloxy)-2,2,2-trifluoroethyl)-2-(dimethylamino)-5,6,7,7a-tetrahydro-3aH-pyrano[3,2-d]thiazole-6,7-diol as a white solid (100 mg, 36%). (ES, m/z) [M+H]$^+$: 423.1; $^1$H NMR (300 MHz, CD$_3$OD) δ 7.24 (d, J=8.7 Hz, 2H), 6.78 (d, J=8.7 Hz, 2H), 6.28 (d, J=6.3 Hz, 1H), 4.76 (d, J=10.5 Hz, 1H), 4.63 (d, J=10.5 Hz, 1H), 4.32-4.25 (m, 1H), 4.02 (t, J=6.3 Hz, 1H), 3.86-3.82 (m, 2H), 3.76-3.71 (m, 1H), 3.00 (s, 6H).

The compounds in Table 1 were prepared by methods substantially similar to those described above.

TABLE 1

| Example | Structure | Name | MH+ |
|---|---|---|---|
| 22 | 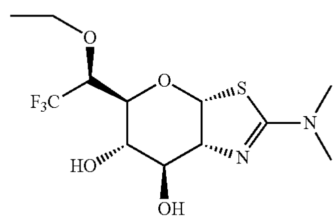 [SMILES: CCO[C@@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol | 345.0 |
| 23 | 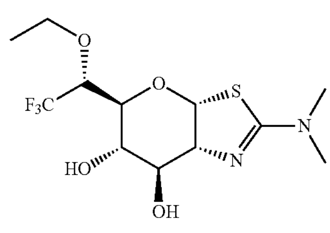 [SMILES: CCO[C@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((R)-1-ethoxy-2,2,2-trifluoroethyl)-5,6,7,7a-tetrahydro-3aH-pyrano[3,2-d]thiazole-6,7-diol | 345.0 |
| 24 | 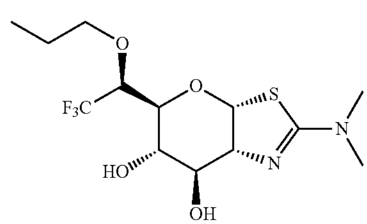 [SMILES: CCCO[C@@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol | 359.0 |

TABLE 1-continued

| Example | Structure | Name | MH+ |
|---|---|---|---|
| 25 | 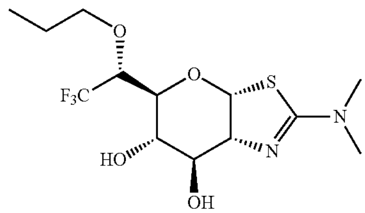 [SMILES: CCCO[C@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((R)-2,2,2-trifluoro-1-propoxyethyl)-5,6,7,7a-tetrahydro-3aH-pyrano[3,2-d]thiazole-6,7-diol | 359.0 |
| 26 | 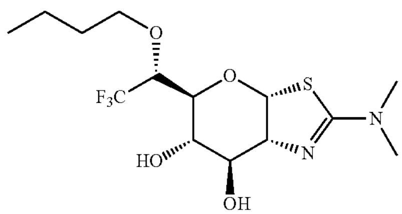 [SMILES: CCCCO[C@H]([C@H]1O[C@@H]2SC(N(C)C)=N[C@@H]2[C@@H](O)[C@@H]1O)C(F)(F)F] | (3aR,5S,6S,7R,7aR)-5-((R)-1-butoxy-2,2,2-trifluoroethyl)-2-(dimethylamino)-5,6,7,7a-tetrahydro-3aH-pyrano[3,2-d]thiazole-6,7-diol | 373.0 |
| 27 | 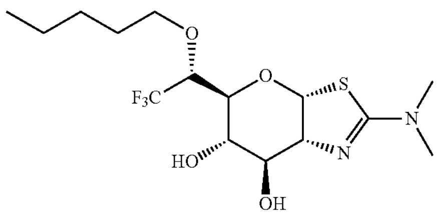 [SMILES: CCCCCO[C@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((R)-2,2,2-trifluoro-1-(pentyloxy)ethyl)-5,6,7,7a-tetrahydro-3aH-pyrano[3,2-d]thiazole-6,7-diol | 387.0 |
| 28 | 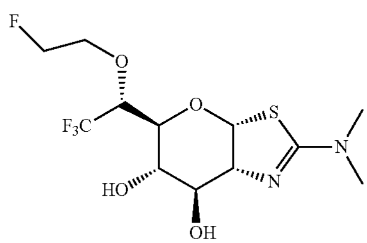 [SMILES: CN(C)C1=N[C@@H]2[C@@H](O)[C@H](O)[C@@H]([C@@H](OCCF)C(F)(F)F)O[C@@H]2S1] | (3aR,5S,6S,7R,7aR)-2-(dimethylamino)-5-((R)-2,2,2-trifluoro-1-(2-fluoroethoxy)ethyl)-5,6,7,7a-tetrahydro-3aH-pyrano[3,2-d]thiazole-6,7-diol | 363.0 |
| 29 | 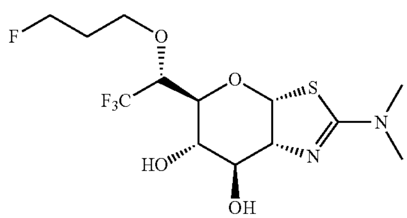 [SMILES: CN(C)C1=N[C@@H]2[C@@H](O)[C@H](O)[C@@H]([C@@H](OCCCF)C(F)(F)F)O[C@@H]2S1] | (3aR,5S,6S,7R,7aR)-2-(dimethylamino)-5-((R)-2,2,2-trifluoro-1-(3-fluoropropoxy)ethyl)-5,6,7,7a-tetrahydro-3aH-pyrano[3,2-d]thiazole-6,7-diol | 377.0 |
| 30 | 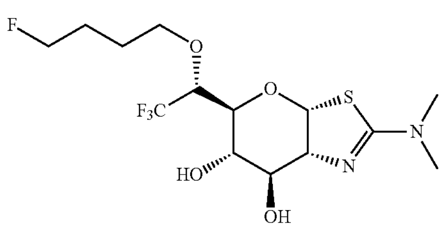 [SMILES: CN(C)C1=N[C@@H]2[C@@H](O)[C@H](O)[C@@H]([C@@H](OCCCCF)C(F)(F)F)O[C@@H]2S1] | (3aR,5S,6S,7R,7aR)-2-(dimethylamino)-5-((R)-2,2,2-trifluoro-1-(4-fluorobutoxy)ethyl)-5,6,7,7a-tetrahydro-3aH-pyrano[3,2-d]thiazole-6,7-diol | 391.0 |
| 31 | 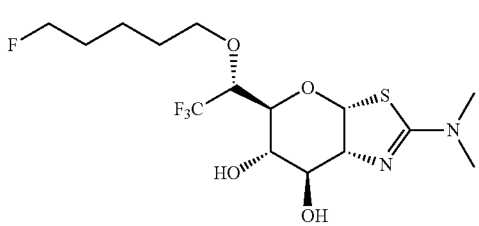 [SMILES: CN(C)C1=N[C@@H]2[C@@H](O)[C@H](O)[C@@H]([C@@H](OCCCCCF)C(F)(F)F)O[C@@H]2S1] | (3aR,5S,6S,7R,7aR)-2-(dimethylamino)-5-((R)-2,2,2-trifluoro-1-(5-fluoropentyloxy)ethyl)-5,6,7,7a-tetrahydro-3aH-pyrano[3,2-d]thiazole-6,7-diol | 405.0 |

TABLE 1-continued

| Example | Structure | Name | MH+ |
|---|---|---|---|
| 32 | 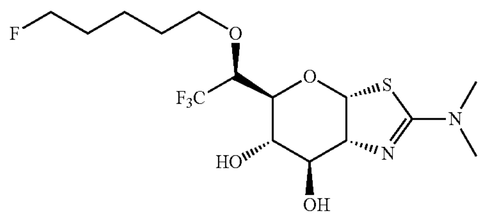 [SMILES: CN(C)C1=N[C@@H]2[C@@H](O)[C@H](O)[C@@H]([C@H](OCCCCCF)C(F)(F)F)O[C@@H]2S1] | (3aR,5S,6S,7R,7aR)-2-(dimethylamino)-5-((S)-2,2,2-trifluoro-1-(5-fluoropentyloxy)ethyl)-5,6,7,7a-tetrahydro-3aH-pyrano[3,2-d]thiazole-6,7-diol | 405.0 |
| 33 | 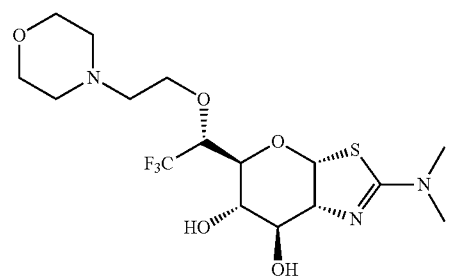 [SMILES: CN(C)C1=N[C@@H]2[C@@H](O)[C@H](O)[C@@H]([C@@H](OCCN3CCOCC3)C(F)(F)F)O[C@@H]2S1] | (3aR,5S,6S,7R,7aR)-2-(dimethylamino)-5-((R)-2,2,2-trifluoro-1-(2-morpholinoethoxy)ethyl)-5,6,7,7a-tetrahydro-3aH-pyrano[3,2-d]thiazole-6,7-diol | 430.0 |
| 34 | 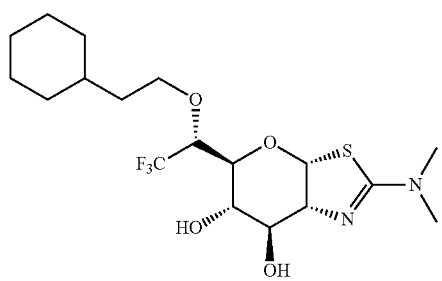 [SMILES: CN(C)C1=N[C@@H]2[C@@H](O)[C@H](O)[C@@H]([C@@H](OCCC3CCCCC3)C(F)(F)F)O[C@@H]2S1] | (3aR,5S,6S,7R,7aR)-5-((R)-1-(2-cyclohexylethoxy)-2,2,2-trifluoroethyl)-2-(dimethylamino)-5,6,7,7a-tetrahydro-3aH-pyrano[3,2-d]thiazole-6,7-diol | 427.0 |
| 35 | 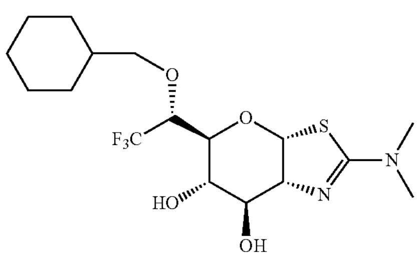 [SMILES: CN(C)C1=N[C@@H]2[C@@H](O)[C@H](O)[C@@H]([C@@H](OCC3CCCCC3)C(F)(F)F)O[C@@H]2S1] | (3aR,5S,6S,7R,7aR)-5-((R)-1-(cyclohexylmethoxy)-2,2,2-trifluoroethyl)-2-(dimethylamino)-5,6,7,7a-tetrahydro-3aH-pyrano[3,2-d]thiazole-6,7-diol | 413.0 |
| 36 | 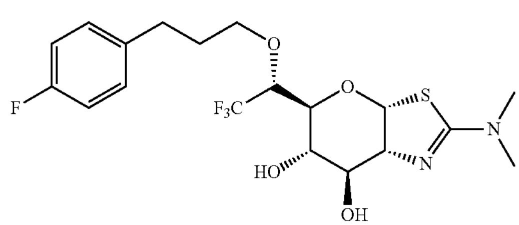 [SMILES: CN(C)C1=N[C@@H]2[C@@H](O)[C@H](O)[C@@H]([C@@H](OCCCc3ccc(F)cc3)C(F)(F)F)O[C@@H]2S1] | (3aR,5S,6S,7R,7aR)-2-(dimethylamino)-5-((R)-2,2,2-trifluoro-1-(3-(4-fluorophenyl)propoxy)ethyl)-5,6,7,7a-tetrahydro-3aH-pyrano[3,2-d]thiazole-6,7-diol | 453.0 |
| 37 | 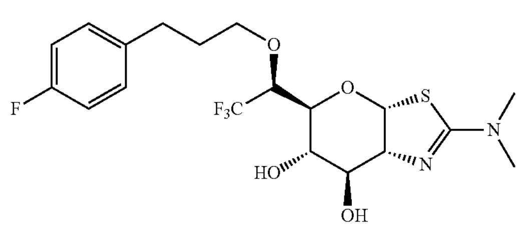 [SMILES: CN(C)C1=N[C@@H]2[C@@H](O)[C@H](O)[C@@H]([C@H](OCCCc3ccc(F)cc3)C(F)(F)F)O[C@@H]2S1] | (3aR,5S,6S,7R,7aR)-2-(dimethylamino)-5-((S)-2,2,2-trifluoro-1-(3-(4-fluorophenyl)propoxy)ethyl)-5,6,7,7a-tetrahydro-3aH-pyrano[3,2-d]thiazole-6,7-diol | 453.0 |

TABLE 1-continued

| Example | Structure | Name | MH+ |
|---|---|---|---|
| 38 | 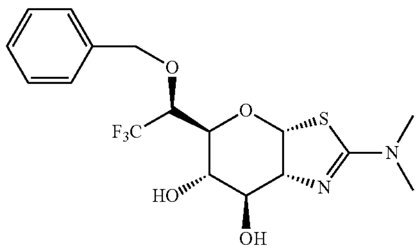 [SMILES: CN(C)C1=N[C@@H]2[C@@H](O)[C@H](O)[C@@H]([C@H](OCc3ccccc3)C(F)(F)F)O[C@@H]2S1] | (3aR,5S,6S,7R,7aR)-5-((S)-1-(benzyloxy)-2,2,2-trifluoroethyl)-2-(dimethylamino)-5,6,7,7a-tetrahydro-3aH-pyrano[3,2-d]thiazole-6,7-diol | 407.0 |
| 39 | 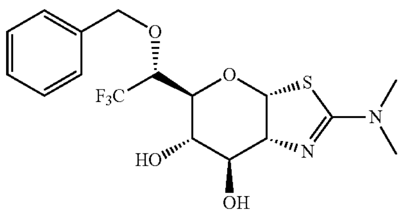 [SMILES: CN(C)C1=N[C@@H]2[C@@H](O)[C@H](O)[C@@H]([C@@H](OCc3ccccc3)C(F)(F)F)O[C@@H]2S1] | (3aR,5S,6S,7R,7aR)-5-((R)-1-(benzyloxy)-2,2,2-trifluoroethyl)-2-(dimethylamino)-5,6,7,7a-tetrahydro-3aH-pyrano[3,2-d]thiazole-6,7-diol | 407.0 |
| 40 | 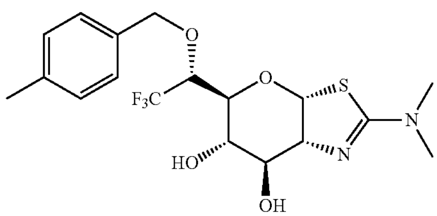 | (3aR,5S,6S,7R,7aR)-2-(dimethylamino)-5-((R)-2,2,2-trifluoro-1-(4-methylbenzyloxy)ethyl)-5,6,7,7a-tetrahydro-3aH-pyrano[3,2-d]thiazole-6,7-diol | 421.0 |
| 41 | 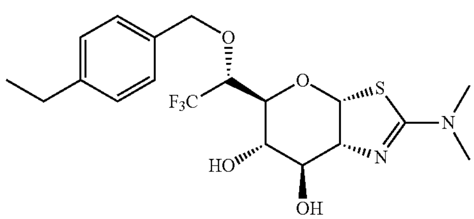 [SMILES: CCc1ccc(CO[C@H]([C@H]2O[C@@H]3SC(N(C)C)=N[C@@H]3[C@@H](O)[C@@H]2O)C(F)(F)F)cc1] | (3aR,5S,6S,7R,7aR)-2-(dimethylamino)-5-((R)-1-(4-ethylbenzyloxy)-2,2,2-trifluoroethyl)-5,6,7,7a-tetrahydro-3aH-pyrano[3,2-d]thiazole-6,7-diol | 435.0 |
| 42 | 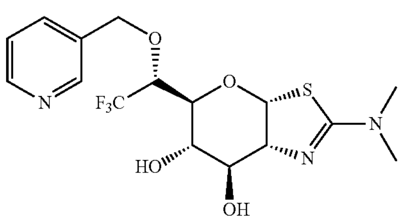 [SMILES: CN(C)C1=N[C@@H]2[C@@H](O)[C@H](O)[C@@H]([C@@H](OCc3cccnc3)C(F)(F)F)O[C@@H]2S1] | (3aR,5S,6S,7R,7aR)-2-(dimethylamino)-5-((R)-2,2,2-trifluoro-1-(pyridin-3-ylmethoxy)ethyl)-5,6,7,7a-tetrahydro-3aH-pyrano[3,2-d]thiazole-6,7-diol | 408.0 |
| 43 | 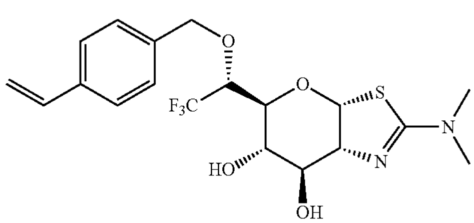 [SMILES: C=Cc1ccc(CO[C@H]([C@H]2O[C@@H]3SC(N(C)C)=N[C@@H]3[C@@H](O)[C@@H]2O)C(F)(F)F)cc1] | (3aR,5S,6S,7R,7aR)-2-(dimethylamino)-5-((R)-2,2,2-trifluoro-1-(4-vinylbenzyloxy)ethyl)-5,6,7,7a-tetrahydro-3aH-pyrano[3,2-d]thiazole-6,7-diol | 433.0 |
| 44 | 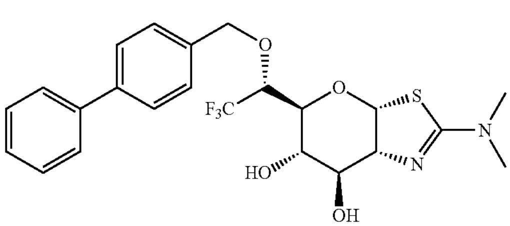 [SMILES: CN(C)C1=N[C@@H]2[C@@H](O)[C@H](O)[C@@H]([C@@H](OCc3ccc(-c4ccccc4)cc3)C(F)(F)F)O[C@@H]2S1] | (3aR,5S,6S,7R,7aR)-5-((R)-1-(biphenyl-4-ylmethoxy)-2,2,2-trifluoroethyl)-2-(dimethylamino)-5,6,7,7a-tetrahydro-3aH-pyrano[3,2-d]thiazole-6,7-diol | 483.0 |

TABLE 1-continued

| Example | Structure | Name | MH+ |
|---|---|---|---|
| 45 | 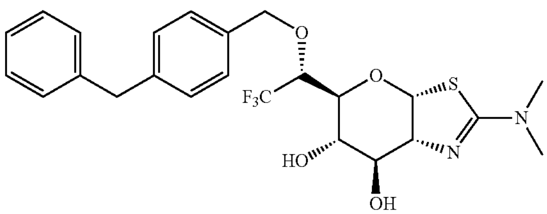 [SMILES: CN(C)C1=N[C@@H]2[C@@H](O)[C@H](O)[C@@H]([C@@H](OCc3ccc(Cc4ccccc4)cc3)C(F)(F)F)O[C@@H]2S1] | (3aR,5S,6S,7R,7aR)-5-((R)-1-(4-benzylbenzyloxy)-2,2,2-trifluoroethyl)-2-(dimethylamino)-5,6,7,7a-tetrahydro-3aH-pyrano[3,2-d]thiazole-6,7-diol | 497.0 |
| 46 | 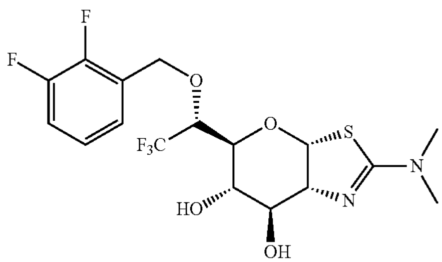 [SMILES: CN(C)C1=N[C@@H]2[C@@H](O)[C@H](O)[C@@H]([C@@H](OCc3cccc(F)c3F)C(F)(F)F)O[C@@H]2S1] | (3aR,5S,6S,7R,7aR)-5-((R)-1-(2,3-difluorobenzyloxy)-2,2,2-trifluoroethyl)-2-(dimethylamino)-5,6,7,7a-tetrahydro-3aH-pyrano[3,2-d]thiazole-6,7-diol | 443.0 |
| 47 | 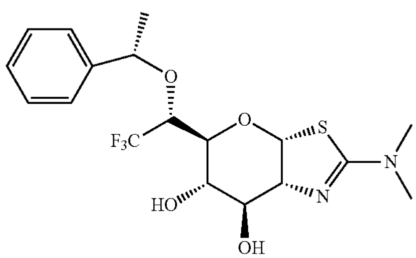 [SMILES: C[C@H](O[C@H]([C@H]1O[C@@H]2SC(N(C)C)=N[C@@H]2[C@@H](O)[C@@H]1O)C(F)(F)F)c1ccccc1] | (3aR,5S,6S,7R,7aR)-2-(dimethylamino)-5-((R)-2,2,2-trifluoro-1-((S)-1-phenylethoxy)ethyl)-5,6,7,7a-tetrahydro-3aH-pyrano[3,2-d]thiazole-6,7-diol (Less-polar epimer on TLC) | 421.0 |
| 48 | 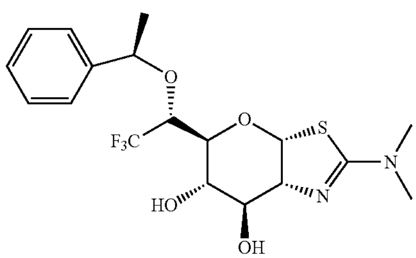 [SMILES: C[C@@H](O[C@H]([C@H]1O[C@@H]2SC(N(C)C)=N[C@@H]2[C@@H](O)[C@@H]1O)C(F)(F)F)c1ccccc1] | (3aR,5S,6S,7R,7aR)-2-(dimethylamino)-5-((R)-2,2,2-trifluoro-1-((R)-1-phenylethoxy)ethyl)-5,6,7,7a-tetrahydro-3aH-pyrano[3,2-d]thiazole-6,7-diol (More-polar epimer on TLC) | 421.0 |
| 49 | 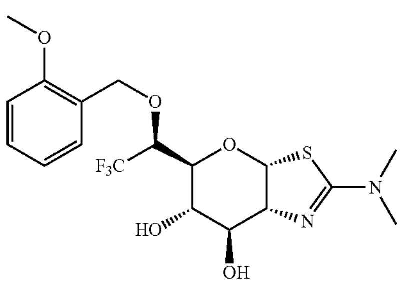 [SMILES: COc1ccccc1CO[C@@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((S)-2,2,2-trifluoro-1-(2-methoxybenzyloxy)ethyl)-5,6,7,7a-tetrahydro-3aH-pyrano[3,2-d]thiazole-6,7-diol | 437.0 |
| 50 | 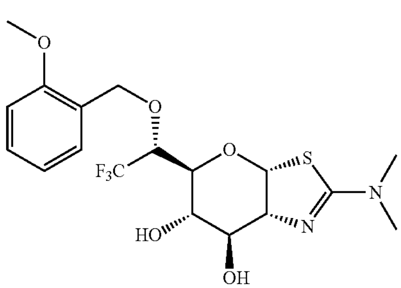 [SMILES: COc1ccccc1CO[C@H]([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((R)-2,2,2-trifluoro-1-(2-methoxybenzyloxy)ethyl)-5,6,7,7a-tetrahydro-3aH-pyrano[3,2-d]thiazole-6,7-diol | 437.0 |

TABLE 1-continued

| Example | Structure | Name | MH+ |
| --- | --- | --- | --- |
| 51 | 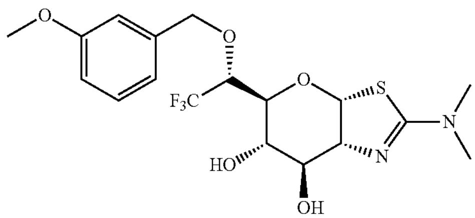 | (3aR,5S,6S,7R,7aR)-2-(dimethylamino)-5-((R)-2,2,2-trifluoro-1-(3-methoxybenzyloxy)ethyl)-5,6,7,7a-tetrahydro-3aH-pyrano[3,2-d]thiazole-6,7-diol | 437.0 |
| 52 | 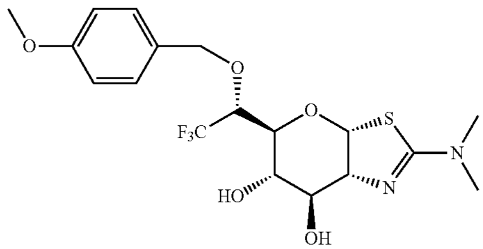 | (3aR,5S,6S,7R,7aR)-2-(dimethylamino)-5-((R)-2,2,2-trifluoro-1-(4-methoxybenzyloxy)ethyl)-5,6,7,7a-tetrahydro-3aH-pyrano[3,2-d]thiazole-6,7-diol | 437.0 |
| 53 | 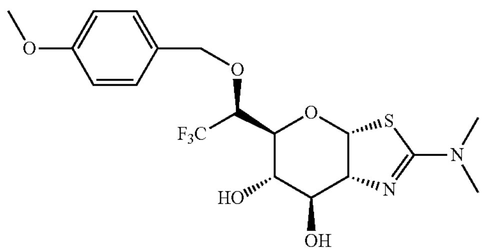 | (3aR,5S,6S,7R,7aR)-2-(dimethylamino)-5-((R)-2,2,2-trifluoro-1-(4-methoxybenzyloxy)ethyl)-5,6,7,7a-tetrahydro-3aH-pyrano[3,2-d]thiazole-6,7-diol | 437.0 |
| 54 | 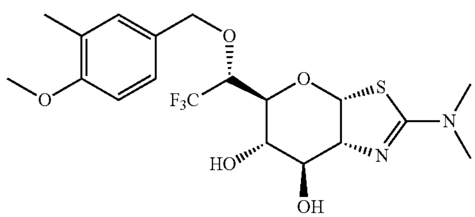 | (3aR,5S,6S,7R,7aR)-2-(dimethylamino)-5-((R)-2,2,2-trifluoro-1-(4-methoxy-3-methylbenzyloxy)ethyl)-5,6,7,7a-tetrahydro-3aH-pyrano[3,2-d]thiazole-6,7-diol | 451.0 |
| 55 | 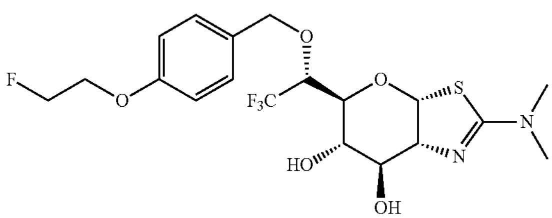 | (3aR,5S,6S,7R,7aR)-2-(dimethylamino)-5-((R)-2,2,2-trifluoro-1-(4-(2-fluoroethoxy)benzyloxy)ethyl)-5,6,7,7a-tetrahydro-3aH-pyrano[3,2-d]thiazole-6,7-diol | 469.0 |
| 56 | 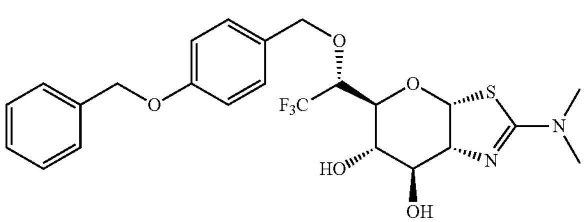 [SMILES: CN(C)C1=N[C@@H]2[C@@H](O)[C@H](O)[C@@H]([C@@H](OCc3ccc(OCc4ccccc4)cc3)C(F)(F)F)O[C@@H]2S1] | (3aR,5S,6S,7R,7aR)-5-((R)-1-(4-(benzyloxy)benzyloxy)-2,2,2-trifluoroethyl)-2-(dimethylamino)-5,6,7,7a-tetrahydro-3aH-pyrano[3,2-d]thiazole-6,7-diol | 513.0 |

TABLE 1-continued

| Example | Structure | Name | MH+ |
|---|---|---|---|
| 57 | 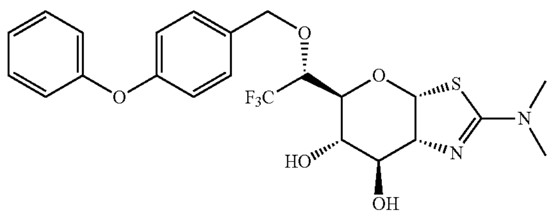 [SMILES: CN(C)C1=N[C@@H]2[C@@H](O)[C@H](O)[C@@H]([C@@H](OCc3ccc(Oc4ccccc4)cc3)C(F)(F)F)O[C@@H]2S1] | (3aR,5S,6S,7R,7aR)-2-(dimethylamino)-5-((R)-2,2,2-trifluoro-1-(4-phenoxybenzyloxy)ethyl)-5,6,7,7a-tetrahydro-3aH-pyrano[3,2-d]thiazole-6,7-diol | 499.0 |
| 58 | 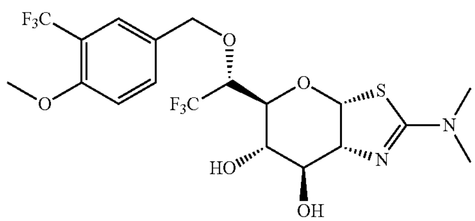 | (3aR,5S,6S,7R,7aR)-2-(dimethylamino)-5-((R)-2,2,2-trifluoro-1-(4-methoxy-3-(trifluoromethyl)benzyloxy)ethyl)-5,6,7,7a-tetrahydro-3aH-pyrano[3,2-d]thiazole-6,7-diol | 505.0 |
| 59 | 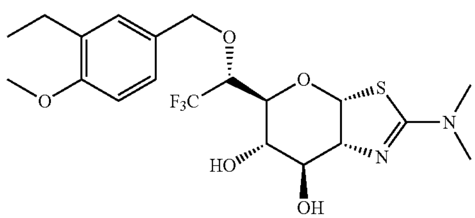 [SMILES: CCc1cc(CO[C@H]([C@H]2O[C@@H]3SC(N(C)C)=N[C@@H]3[C@@H](O)[C@@H]2O)C(F)(F)F)ccc1OC] | (3aR,5S,6S,7R,7aR)-2-(dimethylamino)-5-((R)-1-(3-ethyl-4-methoxybenzyloxy)-2,2,2-trifluoroethyl)-5,6,7,7a-tetrahydro-3aH-pyrano[3,2-d]thiazole-6,7-diol | 465.0 |
| 60 | 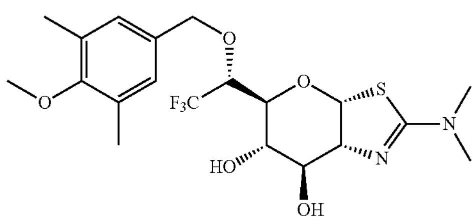 | (3aR,5S,6S,7R,7aR)-2-(dimethylamino)-5-((R)-2,2,2-trifluoro-1-(4-methoxy-3,5-dimethylbenzyloxy)ethyl)-5,6,7,7a-tetrahydro-3aH-pyrano[3,2-d]thiazole-6,7-diol | 465.0 |
| 61 | 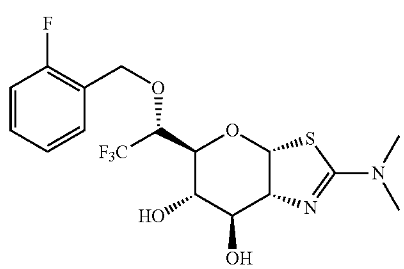 [SMILES: CN(C)C1=N[C@@H]2[C@@H](O)[C@H](O)[C@@H]([C@@H](OCc3ccccc3F)C(F)(F)F)O[C@@H]2S1] | (3aR,5S,6S,7R,7aR)-2-(dimethylamino)-5-((R)-2,2,2-trifluoro-1-(2-fluorobenzyloxy)ethyl)-5,6,7,7a-tetrahydro-3aH-pyrano[3,2-d]thiazole-6,7-diol | 425.0 |
| 62 | 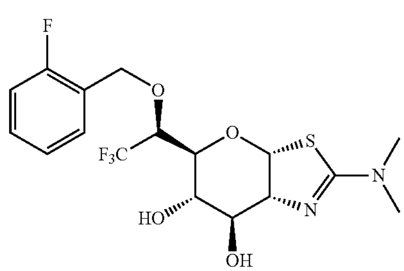 [SMILES: CN(C)C1=N[C@@H]2[C@@H](O)[C@H](O)[C@@H]([C@H](OCc3ccccc3F)C(F)(F)F)O[C@@H]2S1] | (3aR,5S,6S,7R,7aR)-2-(dimethylamino)-5-((S)-2,2,2-trifluoro-1-(2-fluorobenzyloxy)ethyl)-5,6,7,7a-tetrahydro-3aH-pyrano[3,2-d]thiazole-6,7-diol | 425.0 |

TABLE 1-continued

| Example | Structure | Name | MH+ |
|---|---|---|---|
| 63 | 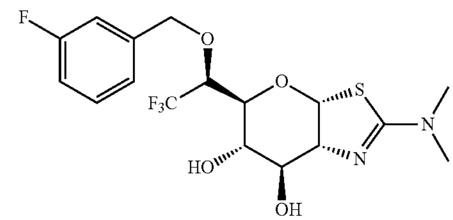 [SMILES: CN(C)C1=N[C@@H]2[C@@H](O)[C@H](O)[C@@H]([C@H](OCc3cccc(F)c3)C(F)(F)F)O[C@@H]2S1] | (3aR,5S,6S,7R,7aR)-2-(dimethylamino)-5-((S)-2,2,2-trifluoro-1-(3-fluorobenzyloxy)ethyl)-5,6,7,7a-tetrahydro-3aH-pyrano[3,2-d]thiazole-6,7-diol | 425.0 |
| 64 | 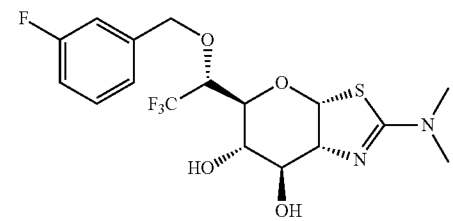 [SMILES: CN(C)C1=N[C@@H]2[C@@H](O)[C@H](O)[C@@H]([C@@H](OCc3cccc(F)c3)C(F)(F)F)O[C@@H]2S1] | (3aR,5S,6S,7R,7aR)-2-(dimethylamino)-5-((S)-2,2,2-trifluoro-1-(3-fluorobenzyloxy)ethyl)-5,6,7,7a-tetrahydro-3aH-pyrano[3,2-d]thiazole-6,7-diol | 425.0 |
| 65 | 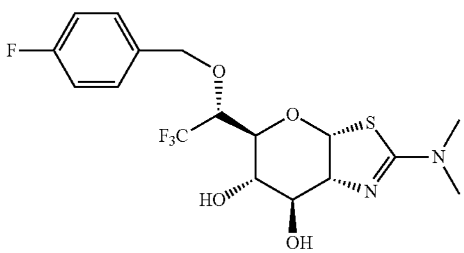 [SMILES: CN(C)C1=N[C@@H]2[C@@H](O)[C@H](O)[C@@H]([C@@H](OCc3ccc(F)cc3)C(F)(F)F)O[C@@H]2S1] | (3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol | 425.0 |
| 66 | 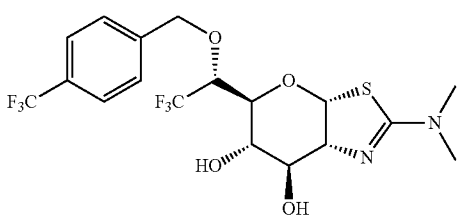 [SMILES: CN(C)C1=N[C@@H]2[C@@H](O)[C@H](O)[C@@H]([C@@H](OCc3ccc(C(F)(F)F)cc3)C(F)(F)F)O[C@@H]2S1] | (3aR,5S,6S,7R,7aR)-2-(dimethylamino)-5-((R)-2,2,2-trifluoro-1-(4-(trifluoromethyl)benzyloxy)ethyl)-5,6,7,7a-tetrahydro-3aH-pyrano[3,2-d]thiazole-6,7-diol | 475.0 |
| 67 | 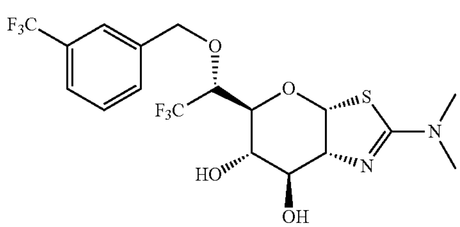 [SMILES: CN(C)C1=N[C@@H]2[C@@H](O)[C@H](O)[C@@H]([C@@H](OCc3cccc(C(F)(F)F)c3)C(F)(F)F)O[C@@H]2S1] | (3aR,5S,6S,7R,7aR)-2-(dimethylamino)-5-((R)-2,2,2-trifluoro-1-(3-(trifluoromethyl)benzyloxy)ethyl)-5,6,7,7a-tetrahydro-3aH-pyrano[3,2-d]thiazole-6,7-diol | 475.0 |
| 68 | 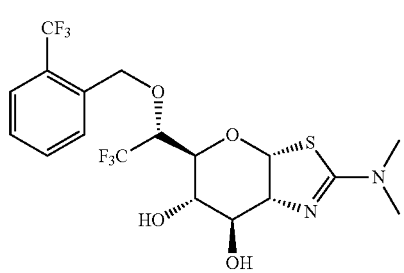 | (3aR,5S,6S,7R,7aR)-2-(dimethylamino)-5-((R)-2,2,2-trifluoro-1-(2-(trifluoromethyl)benzyloxy)ethyl)-5,6,7,7a-tetrahydro-3aH-pyrano[3,2-d]thiazole-6,7-diol | 475.0 |

TABLE 1-continued

| Example | Structure | Name | MH+ |
|---|---|---|---|
| 69 | 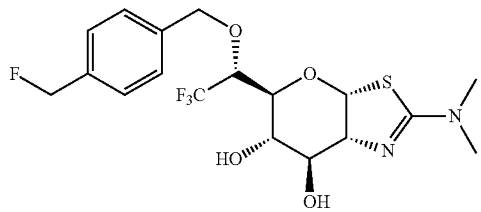 [SMILES: CN(C)C1=N[C@@H]2[C@@H](O)[C@H](O)[C@@H]([C@@H](OCc3ccc(CF)cc3)C(F)(F)F)O[C@@H]2S1] | (3aR,5S,6S,7R,7aR)-2-(dimethylamino)-5-((R)-2,2,2-trifluoro-1-(4-(fluoromethyl)benzyloxy)ethyl)-5,6,7,7a-tetrahydro-3aH-pyrano[3,2-d]thiazole-6,7-diol | 439.0 |
| 70 | 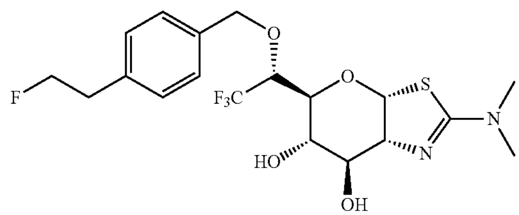 [SMILES: CN(C)C1=N[C@@H]2[C@@H](O)[C@H](O)[C@@H]([C@@H](OCc3ccc(CCF)cc3)C(F)(F)F)O[C@@H]2S1] | (3aR,5S,6S,7R,7aR)-2-(dimethylamino)-5-((R)-2,2,2-trifluoro-1-(4-(2-fluoroethyl)benzyloxy)ethyl)-5,6,7,7a-tetrahydro-3aH-pyrano[3,2-d]thiazole-6,7-diol | 453.0 |
| 71 | 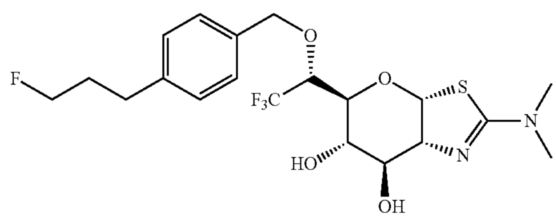 [SMILES: CN(C)C1=N[C@@H]2[C@@H](O)[C@H](O)[C@@H]([C@@H](OCc3ccc(CCCF)cc3)C(F)(F)F)O[C@@H]2S1] | (3aR,5S,6S,7R,7aR)-2-(dimethylamino)-5-((R)-2,2,2-trifluoro-1-(4-(3-fluoropropyl)benzyloxy)ethyl)-5,6,7,7a-tetrahydro-3aH-pyrano[3,2-d]thiazole-6,7-diol | 467.0 |
| 72 | 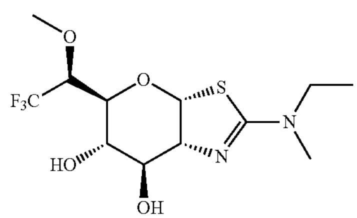 [SMILES: CCN(C)C1=N[C@@H]2[C@@H](O)[C@H](O)[C@@H]([C@H](OC)C(F)(F)F)O[C@@H]2S1] | (3aR,5S,6S,7R,7aR)-2-(ethyl(methyl)amino)-5-((S)-2,2,2-trifluoro-1-methoxyethyl)-5,6,7,7a-tetrahydro-3aH-pyrano[3,2-d]thiazole-6,7-diol | 345.0 |
| 73 | 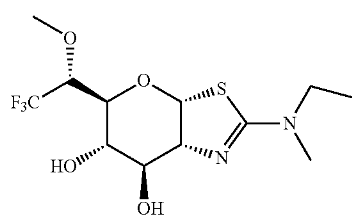 [SMILES: CCN(C)C1=N[C@@H]2[C@@H](O)[C@H](O)[C@@H]([C@@H](OC)C(F)(F)F)O[C@@H]2S1] | (3aR,5S,6S,7R,7aR)-2-(ethyl(methyl)amino)-5-((R)-2,2,2-trifluoro-1-methoxyethyl)-5,6,7,7a-tetrahydro-3aH-pyrano[3,2-d]thiazole-6,7-diol | 345.0 |
| 74 | 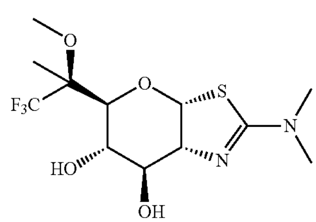 [SMILES: CO[C@@](C)([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-((S)-1,1,1-trifluoro-2-methoxypropan-2-yl)-5,6,7,7a-tetrahydro-3aH-pyrano[3,2-d]thiazole-6,7-diol (Faster eluting isomer by HPLC) | 345.0 |
| 75 | 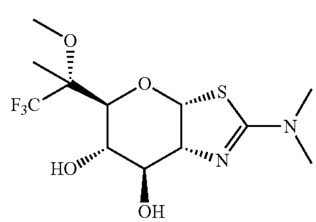 [SMILES: CO[C@](C)([C@H]1O[C@@H]2SC(N(C)C)=N[C@@H]2[C@@H](O)[C@@H]1O)C(F)(F)F] | (3aR,5S,6S,7R,7aR)-2-(dimethylamino)-5-(1,1,1-trifluoro-2-methoxypropan-2-yl)-5,6,7,7a-tetrahydro-3aH-pyrano[3,2-d]thiazole-6,7-diol (Slower eluting isomer by HPLC) | 345.0 |

TABLE 1-continued

| Example | Name | MH+ |
|---|---|---|
| 76 | (3aR,5S,6S,7R,7aR)-5-((R)-2-(benzyloxy)-1,1,1-trifluoro-4-phenylbutan-2-yl)-2-(dimethylamino)-5,6,7,7a-tetrahydro-3aH-pyrano[3,2-d]thiazole-6,7-diol | 511.0 |
| 77 | (3aR,5S,6S,7R,7aR)-2-(methylamino)-5-((S)-2,2,2-trifluoro-1-methoxyethyl)-5,6,7,7a-tetrahydro-3aH-pyrano[3,2-d]thiazole-6,7-diol | 317.0 |
| 78 | (3aR,5S,6S,7R,7aR)-5-((R)-1-ethoxy-2,2,2-trifluoroethyl)-2-(methylamino)-5,6,7,7a-tetrahydro-3aH-pyrano[3,2-d]thiazole-6,7-diol | 331.0 |
| 79 | (3aR,5S,6S,7R,7aR)-2-(methylamino)-5-((R)-2,2,2-trifluoro-1-propoxyethyl)-5,6,7,7a-tetrahydro-3aH-pyrano[3,2-d]thiazole-6,7-diol | 345.0 |
| 80 | (3aR,5S,6S,7R,7aR)-5-((R)-1-(2-cyclohexylethoxy)-2,2,2-trifluoroethyl)-2-(methylamino)-5,6,7,7a-tetrahydro-3aH-pyrano[3,2-d]thiazole-6,7-diol | 413.0 |
| 81 | (3aR,5S,6S,7R,7aR)-2-(methylamino)-5-((R)-2,2,2-trifluoro-1-(2-fluoroethoxy)ethyl)-5,6,7,7a-tetrahydro-3aH-pyrano[3,2-d]thiazole-6,7-diol | 349.0 |

TABLE 1-continued

| Example | Structure | Name | MH+ |
|---|---|---|---|
| 82 | 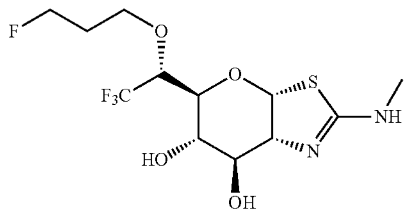 [SMILES: CNC1=N[C@@H]2[C@@H](O)[C@H](O)[C@@H]([C@@H](OCCCF)C(F)(F)F)O[C@@H]2S1] | (3aR,5S,6S,7R,7aR)-2-(methylamino)-5-((R)-2,2,2-trifluoro-1-(3-fluoropropoxy)ethyl)-5,6,7,7a-tetrahydro-3aH-pyrano[3,2-d]thiazole-6,7-diol | 363.0 |
| 83 | 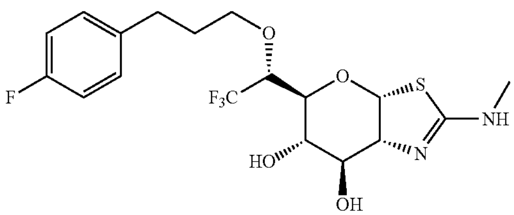 [SMILES: CNC1=N[C@@H]2[C@@H](O)[C@H](O)[C@@H]([C@@H](OCCCc3ccc(F)cc3)C(F)(F)F)O[C@@H]2S1] | (3aR,5S,6S,7R,7aR)-2-(methylamino)-5-((R)-2,2,2-trifluoro-1-(3-(4-fluorophenyl)propoxy)ethyl)-5,6,7,7a-tetrahydro-3aH-pyrano[3,2-d]thiazole-6,7-diol | 439.0 |
| 84 | 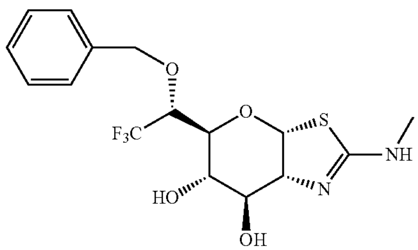 [SMILES: CNC1=N[C@@H]2[C@@H](O)[C@H](O)[C@@H]([C@@H](OCc3ccccc3)C(F)(F)F)O[C@@H]2S1] | (3aR,5S,6S,7R,7aR)-5-((R)-1-(benzyloxy)-2,2,2-trifluoroethyl)-2-(methylamino)-5,6,7,7a-tetrahydro-3aH-pyrano[3,2-d]thiazole-6,7-diol | 393.0 |
| 85 | 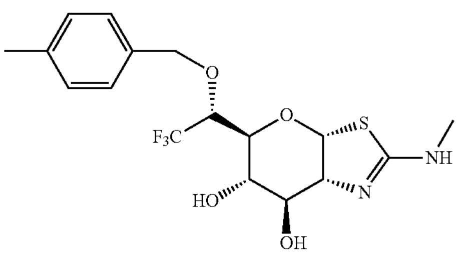 | (3aR,5S,6S,7R,7aR)-2-(methylamino)-5-((R)-2,2,2-trifluoro-1-(4-methylbenzyloxy)ethyl)-5,6,7,7a-tetrahydro-3aH-pyrano[3,2-d]thiazole-6,7-diol | 407.0 |
| 86 | 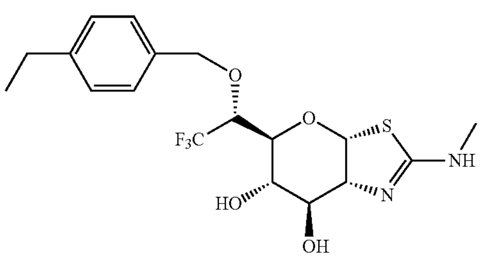 [SMILES: CCc1ccc(CO[C@H]([C@H]2O[C@@H]3SC(NC)=N[C@@H]3[C@@H](O)[C@@H]2O)C(F)(F)F)cc1] | (3aR,5S,6S,7R,7aR)-5-((R)-1-(4-ethylbenzyloxy)-2,2,2-trifluoroethyl)-2-(methylamino)-5,6,7,7a-tetrahydro-3aH-pyrano[3,2-d]thiazole-6,7-diol | 421.0 |
| 87 | 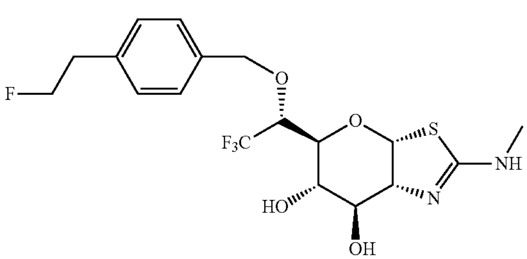 [SMILES: CNC1=N[C@@H]2[C@@H](O)[C@H](O)[C@@H]([C@@H](OCc3ccc(CCF)cc3)C(F)(F)F)O[C@@H]2S1] | (3aR,5S,6S,7R,7aR)-2-(methylamino)-5-((R)-2,2,2-trifluoro-1-(4-(2-fluoroethyl)benzyloxy)ethyl)-5,6,7,7a-tetrahydro-3aH-pyrano[3,2-d]thiazole-6,7-diol | 439.0 |

TABLE 1-continued

| Example | Structure | Name | MH+ |
|---|---|---|---|
| 88 | 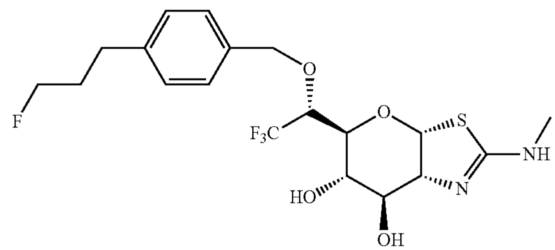 [SMILES: CNC1=N[C@@H]2[C@@H](O)[C@H](O)[C@@H]([C@@H](OCc3ccc(CCCF)cc3)C(F)(F)F)O[C@@H]2S1] | (3aR,5S,6S,7R,7aR)-2-(methylamino)-5-((R)-2,2,2-trifluoro-1-(4-(3-fluoropropyl)benzyloxy)ethyl)-5,6,7,7a-tetrahydro-3aH-pyrano[3,2-d]thiazole-6,7-diol | 453.0 |
| 89 | 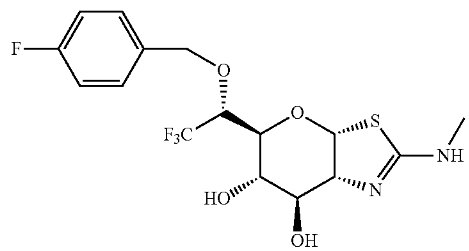 [SMILES: CNC1=N[C@@H]2[C@@H](O)[C@H](O)[C@@H]([C@@H](OCc3ccc(F)cc3)C(F)(F)F)O[C@@H]2S1] | (3aR,5S,6S,7R,7aR)-2-(methylamino)-5-((R)-2,2,2-trifluoro-1-(4-fluorobenzyloxy)ethyl)-5,6,7,7a-tetrahydro-3aH-pyrano[3,2-d]thiazole-6,7-diol | 411.0 |
| 90 | 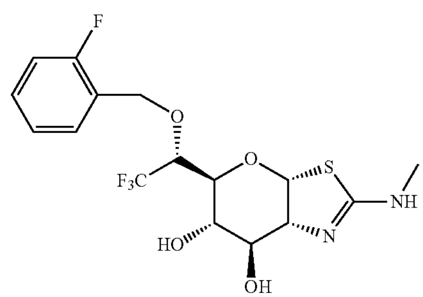 [SMILES: CNC1=N[C@@H]2[C@@H](O)[C@H](O)[C@@H]([C@@H](OCc3ccccc3F)C(F)(F)F)O[C@@H]2S1] | (3aR,5S,6S,7R,7aR)-2-(methylamino)-5-((R)-2,2,2-trifluoro-1-(2-fluorobenzyloxy)ethyl)-5,6,7,7a-tetrahydro-3aH-pyrano[3,2-d]thiazole-6,7-diol | 411.0 |
| 91 | 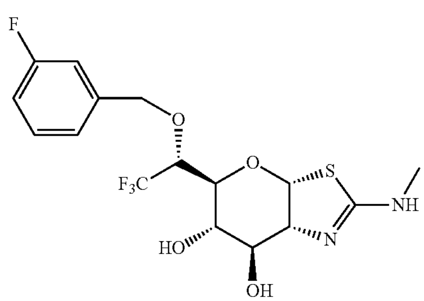 [SMILES: CNC1=N[C@@H]2[C@@H](O)[C@H](O)[C@@H]([C@@H](OCc3cccc(F)c3)C(F)(F)F)O[C@@H]2S1] | (3aR,5S,6S,7R,7aR)-2-(methylamino)-5-((R)-2,2,2-trifluoro-1-(3-fluorobenzyloxy)ethyl)-5,6,7,7a-tetrahydro-3aH-pyrano[3,2-d]thiazole-6,7-diol | 411.0 |
| 92 | 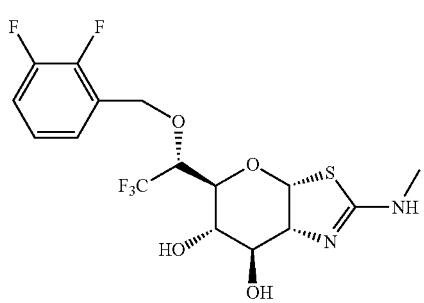 [SMILES: CNC1=N[C@@H]2[C@@H](O)[C@H](O)[C@@H]([C@@H](OCc3cccc(F)c3F)C(F)(F)F)O[C@@H]2S1] | (3aR,5S,6S,7R,7aR)-5-((R)-1-(2,3-difluorobenzyloxy)-2,2,2-trifluoroethyl)-2-(methylamino)-5,6,7,7a-tetrahydro-3aH-pyrano[3,2-d]thiazole-6,7-diol | 429.0 |

TABLE 1-continued

| Example | Structure | Name | MH+ |
|---|---|---|---|
| 93 | 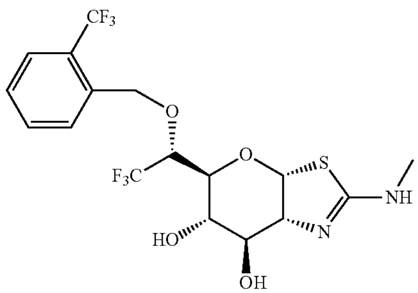 [SMILES: CNC1=N[C@@H]2[C@@H](O)[C@H](O)[C@@H]([C@@H](OCc3ccccc3C(F)(F)F)C(F)(F)F)O[C@@H]2S1] | (3aR,5S,6S,7R,7aR)-2-(methylamino)-5-((R)-2,2,2-trifluoro-1-(2-(trifluoromethyl)benzyloxy)ethyl)-5,6,7,7a-tetrahydro-3aH-pyrano[3,2-d]thiazole-6,7-diol | 461.0 |
| 94 | 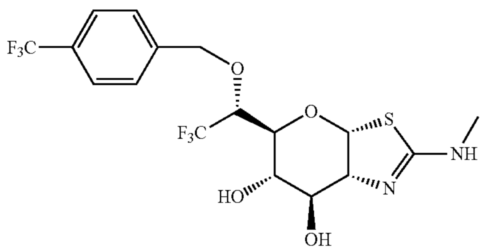 [SMILES: CNC1=N[C@@H]2[C@@H](O)[C@H](O)[C@@H]([C@@H](OCc3ccc(C(F)(F)F)cc3)C(F)(F)F)O[C@@H]2S1] | (3aR,5S,6S,7R,7aR)-2-(methylamino)-5-((R)-2,2,2-trifluoro-1-(4-(trifluoromethyl)benzyloxy)ethyl)-5,6,7,7a-tetrahydro-3aH-pyrano[3,2-d]thiazole-6,7-diol | 461.0 |
| 95 | 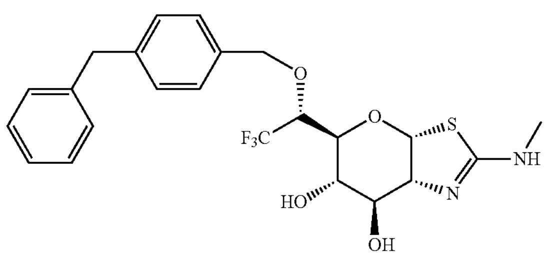 | (3aR,5S,6S,7R,7aR)-5-((R)-1-(4-benzylbenzyloxy)-2,2,2-trifluoroethyl)-2-(methylamino)-5,6,7,7a-tetrahydro-3aH-pyrano[3,2-d]thiazole-6,7-diol | 483.0 |
| 96 | 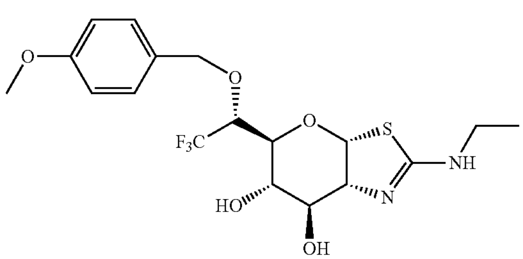 [SMILES: CCNC1=N[C@@H]2[C@@H](O)[C@H](O)[C@@H]([C@@H](OCc3ccc(OC)cc3)C(F)(F)F)O[C@@H]2S1] | (3aR,5S,6S,7R,7aR)-2-(ethylamino)-5-((R)-2,2,2-trifluoro-1-(4-methoxybenzyloxy)ethyl)-5,6,7,7a-tetrahydro-3aH-pyrano[3,2-d]thiazole-6,7-diol | 437.0 |
| 97 | 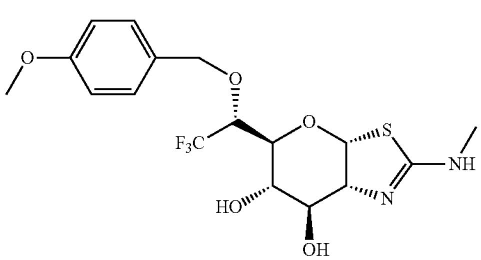 | 2-(methylamino)-5-(2,2,2-trifluoro-1-(4-methoxybenzyloxy)ethyl)-5,6,7,7a-tetrahydro-3aH-pyrano[3,2-d]thiazole-6,7-diol | 423.0 |

TABLE 1-continued

| Example | Structure | Name | MH+ |
|---|---|---|---|
| 98 | 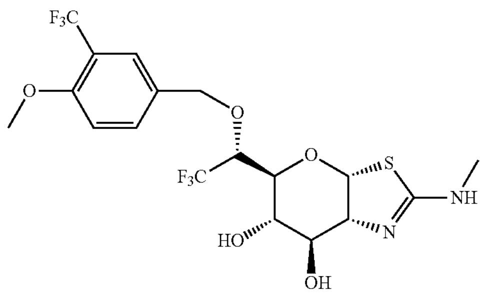 | (3aR,5S,6S,7R,7aR)-2-(methylamino)-5-((R)-2,2,2-trifluoro-1-(4-methoxy-3-(trifluoromethyl)benzyloxy)ethyl)-5,6,7,7a-tetrahydro-3aH-pyrano[3,2-d]thiazole-6,7-diol | 491.0 |
| 99 | 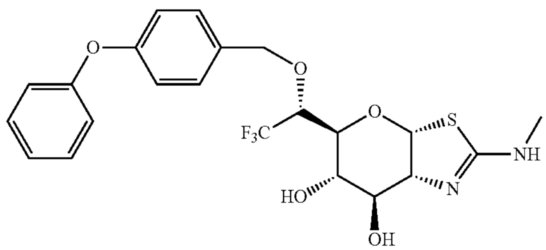 | (3aR,5S,6S,7R,7aR)-2-(methylamino)-5-((R)-2,2,2-trifluoro-1-(4-phenoxybenzyloxy)ethyl)-5,6,7,7a-tetrahydro-3aH-pyrano[3,2-d]thiazole-6,7-diol | 485.0 |
| 100 | 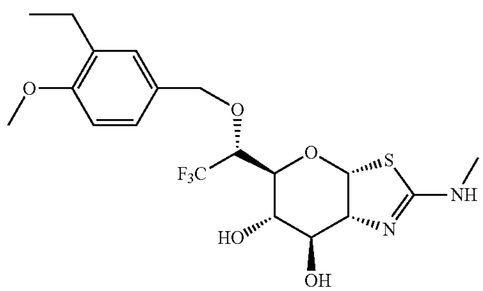 | (3aR,5S,6S,7R,7aR)-5-((R)-1-(3-ethyl-4-methoxybenzyloxy)-2,2,2-trifluoroethyl)-2-(methylamino)-5,6,7,7a-tetrahydro-3aH-pyrano[3,2-d]thiazole-6,7-diol | 451.0 |
| 101 | 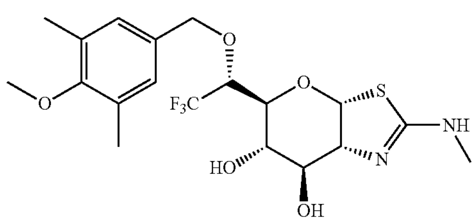 | (3aR,5S,6S,7R,7aR)-2-(methylamino)-5-((R)-2,2,2-trifluoro-1-(4-methoxy-3,5-dimethylbenzyloxy)ethyl)-5,6,7,7a-tetrahydro-3aH-pyrano[3,2-d]thiazole-6,7-diol | 451.0 |
| 102 | 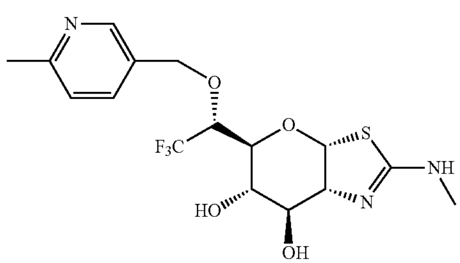 | (3aR,5S,6S,7R,7aR)-2-(methylamino)-5-((R)-2,2,2-trifluoro-1-((6-methylpyridin-3-yl)methoxy)ethyl)-5,6,7,7a-tetrahydro-3aH-pyrano[3,2-d]thiazole-6,7-diol | 408.0 |
| 103 | 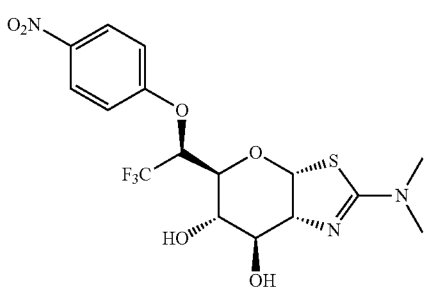 [SMILES: CN(C)C1=N[C@@H]2[C@@H](O)[C@H](O)[C@@H]([C@H](Oc3ccc([N+](=O)[O-])cc3)C(F)(F)F)O[C@@H]2S1] | (3aR,5S,6S,7R,7aR)-2-(dimethylamino)-5-((S)-2,2,2-trifluoro-1-(4-nitrophenoxy)ethyl)-5,6,7,7a-tetrahydro-3aH-pyrano[3,2-d]thiazole-6,7-diol | 438.0 |

TABLE 1-continued

| Example | Structure | Name | MH+ |
|---|---|---|---|
| 104 | 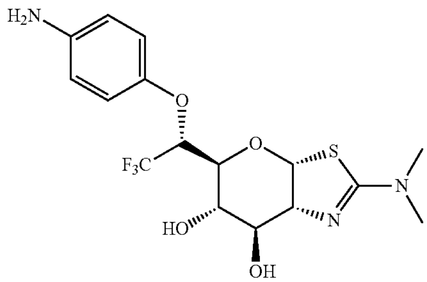 [SMILES: CN(C)C1=N[C@@H]2[C@@H](O)[C@H](O)[C@@H]([C@@H](Oc3ccc(N)cc3)C(F)(F)F)O[C@@H]2S1] | (3aR,5S,6S,7R,7aR)-5-((R)-1-(4-aminophenoxy)-2,2,2-trifluoroethyl)-2-(dimethylamino)-5,6,7,7a-tetrahydro-3aH-pyrano[3,2-d]thiazole-6,7-diol | 408.0 |
| 105 | 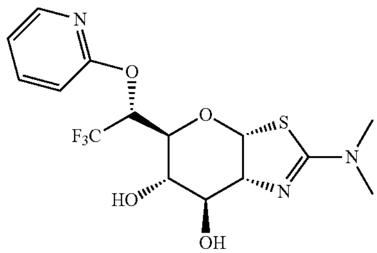 [SMILES: CN(C)C1=N[C@@H]2[C@@H](O)[C@H](O)[C@@H]([C@@H](Oc3ccccn3)C(F)(F)F)O[C@@H]2S1] | (3aR,5S,6S,7R,7aR)-2-(dimethylamino)-5-((R)-2,2,2-trifluoro-1-(pyridin-2-yloxy)ethyl)-5,6,7,7a-tetrahydro-3aH-pyrano[3,2-d]thiazole-6,7-diol | 394.0 |
| 106 | 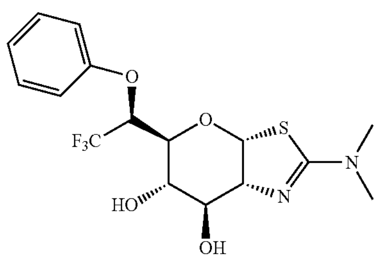 [SMILES: CN(C)C1=N[C@@H]2[C@@H](O)[C@H](O)[C@@H]([C@H](Oc3ccccc3)C(F)(F)F)O[C@@H]2S1] | (3aR,5S,6S,7R,7aR)-2-(dimethylamino)-5-((S)-2,2,2-trifluoro-1-phenoxyethyl)-5,6,7,7a-tetrahydro-3aH-pyrano[3,2-d]thiazole-6,7-diol | 393.0 |
| 107 | 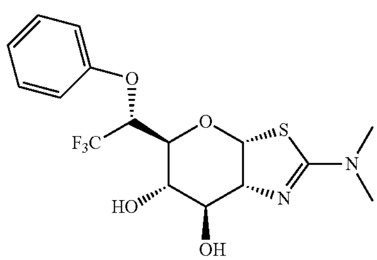 [SMILES: CN(C)C1=N[C@@H]2[C@@H](O)[C@H](O)[C@@H]([C@@H](Oc3ccccc3)C(F)(F)F)O[C@@H]2S1] | (3aR,5S,6S,7R,7aR)-2-(dimethylamino)-5-((R)-2,2,2-trifluoro-1-phenoxyethyl)-5,6,7,7a-tetrahydro-3aH-pyrano[3,2-d]thiazole-6,7-diol | 393.0 |
| 108 | 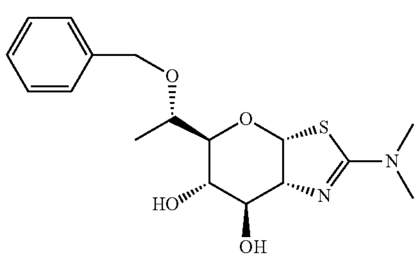 [SMILES: C[C@H](OCc1ccccc1)[C@H]1O[C@@H]2SC(N(C)C)=N[C@@H]2[C@@H](O)[C@@H]1O] | (3aR,5S,6S,7R,7aR)-5-((S)-1-(benzyloxy)ethyl)-2-(dimethylamino)-5,6,7,7a-tetrahydro-3aH-pyrano[3,2-d]thiazole-6,7-diol | 353.0 |
| 109 | 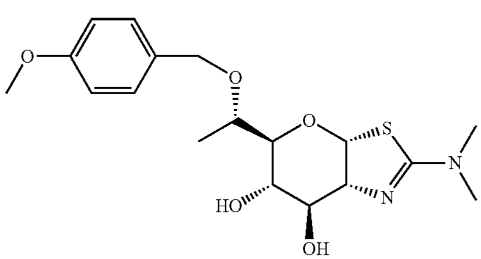 | (3aR,5S,6S,7R,7aR)-2-(dimethylamino)-5-((S)-1-(4-methoxybenzyloxy)ethyl)-5,6,7,7a-tetrahydro-3aH-pyrano[3,2-d]thiazole-6,7-diol | 383.0 |

TABLE 1-continued

| Example | Structure | Name | MH+ |
|---|---|---|---|
| 110 | 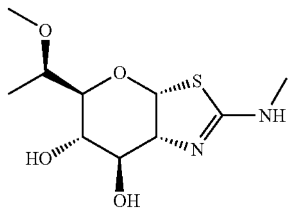 [SMILES: CNC1=N[C@@H]2[C@@H](O)[C@H](O)[C@@H]([C@@H](C)OC)O[C@@H]2S1] | (3aR,5S,6S,7R,7aR)-5-((R)-1-methoxyethyl)-2-(methylamino)-5,6,7,7a-tetrahydro-3aH-pyrano[3,2-d]thiazole-6,7-diol | 263.0 |
| 111 | 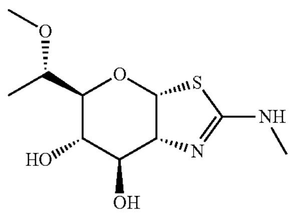 [SMILES: CNC1=N[C@@H]2[C@@H](O)[C@H](O)[C@@H]([C@H](C)OC)O[C@@H]2S1] | (3aR,5S,6S,7R,7aR)-5-((S)-1-methoxyethyl)-2-(methylamino)-5,6,7,7a-tetrahydro-3aH-pyrano[3,2-d]thiazole-6,7-diol | 263.0 |
| 112 | 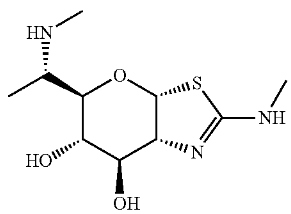 [SMILES: CNC1=N[C@@H]2[C@@H](O)[C@H](O)[C@@H]([C@H](C)NC)O[C@@H]2S1] | (3aR,5R,6S,7R,7aR)-2-(methylamino)-5-((S)-1-(methylamino)ethyl)-5,6,7,7a-tetrahydro-3aH-pyrano[3,2-d]thiazole-6,7-diol(Slower eluting isomer) | 261.9 |
| 113 | 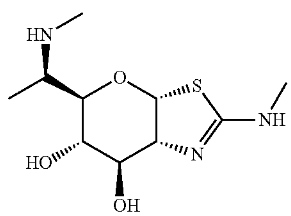 [SMILES: CNC1=N[C@@H]2[C@@H](O)[C@H](O)[C@@H]([C@@H](C)NC)O[C@@H]2S1] | (3aR,5R,6S,7R,7aR)-2-(methylamino)-5-((R)-1-(methylamino)ethyl)-5,6,7,7a-tetrahydro-3aH-pyrano[3,2-d]thiazole-6,7-diol(Faster eluting isomer) | 261.9 |
| 114 | 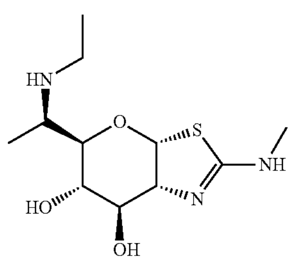 [SMILES: CCN[C@H](C)[C@H]1O[C@@H]2SC(NC)=N[C@@H]2[C@@H](O)[C@@H]1O] | (3aR,5R,6S,7R,7aR)-5-((R)-1-(ethylamino)ethyl)-2-(methylamino)-5,6,7,7a-tetrahydro-3aH-pyrano[3,2-d]thiazole-6,7-diol(Faster eluting isomer) | 276.0 |
| 115 | 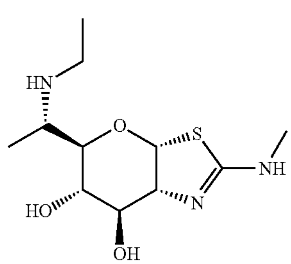 [SMILES: CCN[C@@H](C)[C@H]1O[C@@H]2SC(NC)=N[C@@H]2[C@@H](O)[C@@H]1O] | (3aR,5R,6S,7R,7aR)-5-((S)-1-(ethylamino)ethyl)-2-(methylamino)-5,6,7,7a-tetrahydro-3aH-pyrano[3,2-d]thiazole-6,7-diol(Slower eluting isomer) | 276.0 |

TABLE 1-continued

| Example | Structure | Name | MH+ |
|---|---|---|---|
| 116 | 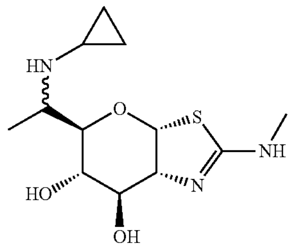 [SMILES: CNC1=N[C@@H]2[C@@H](O)[C@H](O)[C@@H](C(C)NC3CC3)O[C@@H]2S1] | (3aR,5R,6S,7R,7aR)-5-(1-(cyclopropylamino)ethyl)-2-(methylamino)-5,6,7,7a-tetrahydro-3aH-pyrano[3,2-d]thiazole-6,7-diol(Faster eluting isomer: Slower eluting isomer = 2:1) | 288.2 |

Example 117

(1R,2R,6R,8S,9S)—N,11,11-trimethyl-8-[(1S)-2,2,2-trifluoro-1-[(4-fluorophenyl)methoxy]ethyl]-7,10,12-trioxa-5-thia-3-azatricyclo[7.3.0.0[2,6]]dodec-3-en-4-amine

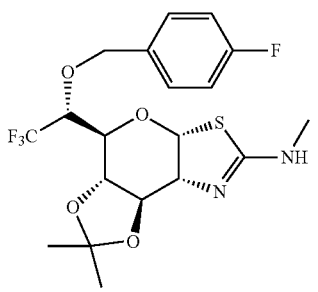 [SMILES: CNC1=N[C@@H]2[C@H]3OC(C)(C)O[C@@H]3[C@@H]([C@@H](OCc3ccc(F)cc3)C(F)(F)F)O[C@@H]2S1]

Scheme XIV

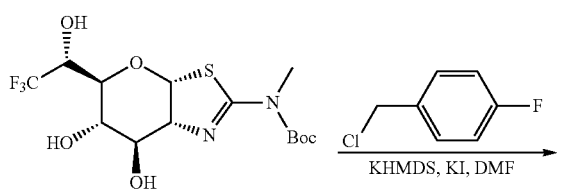

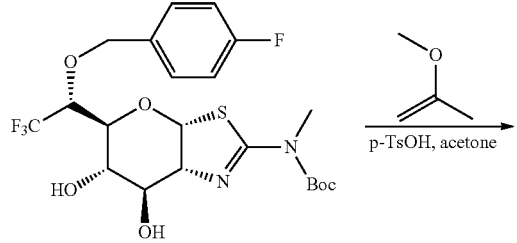

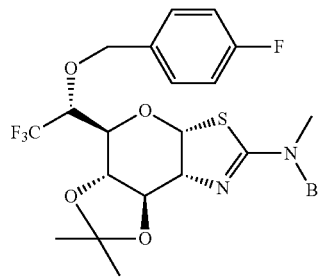

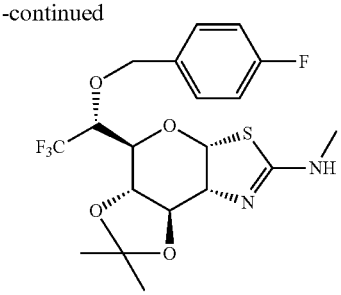

tert-butyl (3aR,5S,6S,7R,7aR)-5-((R)-1-(4-fluorobenzyloxy)-2,2,2-trifluoroethyl)-6,7-dihydroxy-5,6,7,7a-tetrahydro-3aH-pyrano[3,2-d]thiazol-2-yl(methyl)carbamate A solution of tert-butyl (3aR,5S,6S,7R,7aR)-6,7-dihydroxy-5-((R)-2,2,2-trifluoro-1-hydroxyethyl)-5,6,7,7a-tetrahydro-3aH-pyrano[3,2-d]thiazol-2-yl(methyl)carbamate (350 mg, 0.87 mmol) in DMF (20 mL) was treated with 1N solution of KHMDS (1.3 mL, 1.30 mmol) in THF at 0° C. for 30 min, followed by the addition of 1-(chloromethyl)-4-fluorobenzene (250 mg, 1.73 mmol) and KI (73 mg, 0.44 mmol). After additional 1 hour at room temperature, the reaction was quenched by the addition of water (1 mL) and concentrated to give a residue, which was purified by a silica gel column, eluted with 20%-40% ethyl acetate in petroleum ether to give the title compound as a yellow syrup (220 mg, 50%). (ES, m/z) [M+H]+ 511.1; $^1$H NMR (300 MHz, CD$_3$Cl) δ 7.33-7.27 (m, 2H), 7.14-7.05 (m, 2H), 6.15 (d, J=5.7 Hz, 1H), 4.96-4.93 (m, 1H), 4.68-4.64 (m, 1H), 4.26-4.24 (m, 1H), 4.17-4.11 (m, 1H), 3.93-3.87 (m, 1H), 3.83-3.74 (m, 2H), 3.25 (s, 3H), 1.52 (s, 9H).

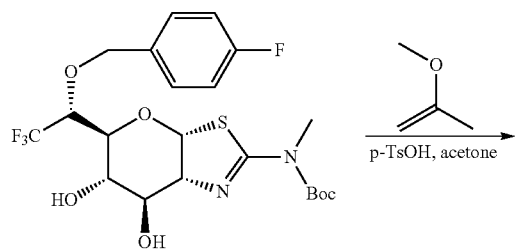

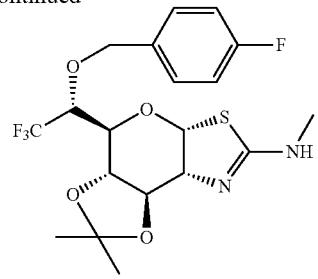

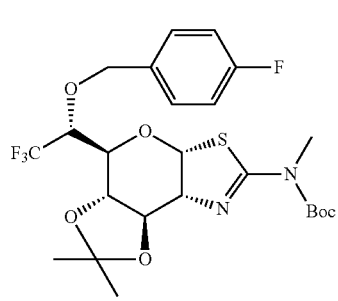

tert-butyl N-[(1R,2R,6R,8S,9S)-11,11-dimethyl-8-[(1S)-2,2,2-trifluoro-1-[(4-fluorophenyl)methoxy]ethyl]-7,10,12-trioxa-5-thia-3-azatricyclo[7.3.0.0[2,6]]dodec-3-en-4-yl]-N-methylcarbamate To a solution of tert-butyl (3aR,5S,6S,7R,7aR)-5-((R)-1-(4-fluorobenzyloxy)-2,2,2-trifluoroethyl)-6,7-dihydroxy-5,6,7,7a-tetrahydro-3aH-pyrano[3,2-d]thiazol-2-yl(methyl)carbamate (70 mg, 0.14 mmol) in acetone (10 mL) was added 2-methoxyprop-1-ene (198 mg, 2.75 mmol) and p-TsOH (4.8 mg, 0.03 mmol) at 25° C. After stirring 1 hour at this temperature, the reaction was quenched by saturated aqueous sodium bicarbonate (50 mL) solution and extracted with ethyl acetate (3×50 mL). The combined organic layer was washed with brine (20 mL), dried over anhydrous sodium sulfate and concentrated under vacuum to give a residue, which was purified by a silica gel column, eluted with 8%-10% ethyl acetate in petroleum ether to give the product as a yellow syrup (40 mg, 53%). (ES, m/z) [M+H]$^+$ 551.1; $^1$H NMR (300 MHz, CD$_3$Cl) δ 7.34-7.26 (m, 2H), 7.17-7.05 (m, 2H), 5.98 (d, J=5.7 Hz, 1H), 4.93 (d, J=10.5 Hz, 1H), 4.62 (d, J=10.5 Hz, 1H), 4.25-4.21 (m, 1H), 4.16-4.11 (m, 1H), 3.93-3.87 (m, 1H), 3.83-3.74 (m, 2H), 3.23 (s, 3H), 1.51 (s, 9H), 1.44 (s, 3H), 1.41 (s, 3H).

(1R,2R,6R,8S,9S)—N,11,11-trimethyl-8-[(1S)-2,2,2-trifluoro-1-[(4-fluorophenyl)methoxy]ethyl]-7,10,12-trioxa-5-thia-3-azatricyclo[7.3.0.0[2,6]]dodec-3-en-4-amine A solution of tert-butyl N-[(1R,2R,6R,8S,9S)-11,11-dimethyl-8-[(1S)-2,2,2-trifluoro-1-[(4-fluorophenyl)methoxy]ethyl]-7,10,12-trioxa-5-thia-3-azatricyclo[7.3.0.0[2,6]]dodec-3-en-4-yl]-N-methylcarbamate (120 mg, 0.22 mmol) in THF (20 mL) was treated with 1N of bromomethylmagnesium (1.5 mL, 1.5 mmol) in THF for 1 hour at 25° C. The reaction was quenched by water (50 mL) and extracted with ethyl acetate (3×30 mL). The combined organic layer was washed with brine (20 mL), dried over anhydrous sodium sulfate and concentrated under vacuum to give a residue, which was purified by Prep-HPLC with the following conditions [(Agilent 1200 prep HPLC); Column: Sun Fire Prep C18,19*50 mm 5 um; mobile phase: water with 0.03% NH$_4$OH and CH$_3$CN (10% CH$_3$CN up to 45% in 10 min); Detector: UV 220 nm)] to give the product as a white solid (52 mg, 53%). (ES, m/z) [M+H]$^+$ 451.1; $^1$HNMR (300 MHz, CDCl$_3$) δ 7.36-7.31 (m, 2H), 7.10-7.04 (m, 2H), 6.23 (d, J=5.7 Hz, 1H), 4.90 (d, J=11.4 Hz, 1H), 4.62 (d, J=11.4 Hz, 1H), 4.30-4.28 (m, 1H), 4.17 (d, J=8.4 Hz, 1H), 3.98-3.92 (m, 1H), 3.87-3.81 (m, 1H), 3.73-3.67 (m, 1H), 2.93 (s, 3H), 1.41 (s, 3H), 1.37 (s, 3H).

Example 118

(3aR,5S,6S,7R,7aR)-2-(dimethylamino)-5-((R)-2,2,2-trifluoro-1-[$^{11}$C]methoxyethyl)-5,6,7,7a-tetrahydro-3aH-pyrano[3,2-d]thiazole-6,7-diol

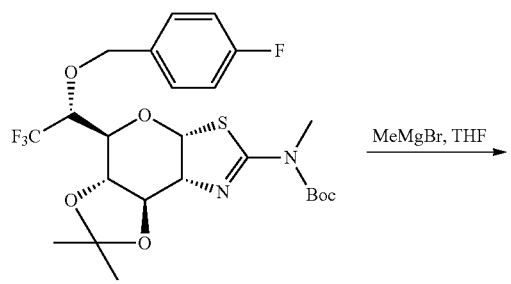

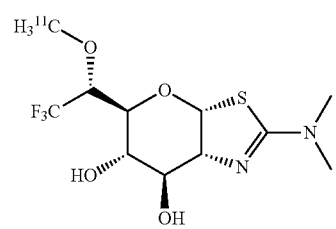 [SMILES: CN(C)C1=N[C@@H]2[C@@H](O)[C@H](O)[C@@H]([C@@H](O[11CH3])C(F)(F)F)O[C@@H]2S1]

Scheme XV

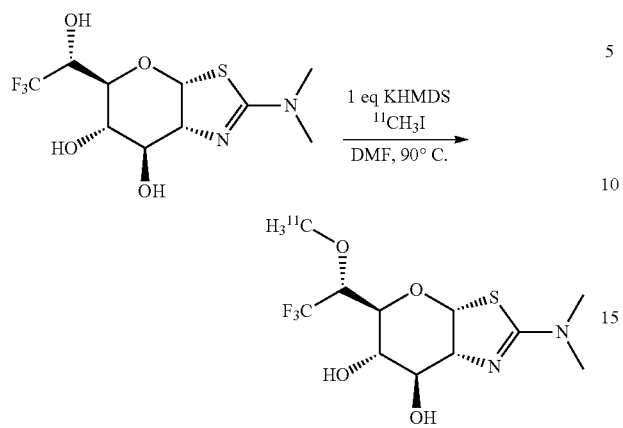

Step 1: Synthesis of [¹¹C]iodomethane. [¹¹C]CO$_2$ was produced using a Siemens RDS-111 cyclotron and the [¹¹C]CO$_2$ was converted to [¹¹C]MeI using a GE Medical Systems TRACERlab FCX system.

Step 2: [¹¹C]MeI (from Step 1, 297 mCi) was trapped in a 0° C. mixture of (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol (0.42 mg) in DMF (0.25 mL) containing 1 µl of KHMDS (1 M in THF). The reaction mixture was transferred to a 2 mL v-vial at 90° C., heated for 5 minutes, diluted with H$_2$O (0.8 mL) and injected onto the HPLC (XBridge C18, 10×150 mm, Waters). The desired peak (retention time 12.1 min) was eluted with a solvent system consisting 20% A 80% B to 80% A 20% B under 20-min linear gradient at 3 mL/min (A=MeCN, B=0.1% ammonium hydroxide), and collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 51 mCi of (3aR,5S,6S,7R,7aR)-2-(dimethylamino)-5-((R)-2,2,2-trifluoro-1-[¹¹C]methoxyethyl)-5,6,7,7a-tetrahydro-3aH-pyrano[3,2-d]thiazole-6,7-diol.

Example 119

(3aR,5S,6S,7R,7aR)-2-(dimethylamino)-5-((R)-2,2,2-trifluoro-1-[¹¹C](4-methoxybenzyloxy)ethyl)-5,6,7,7a-tetrahydro-3aH-pyrano[3,2-d]thiazole-6,7-diol

Scheme XVI

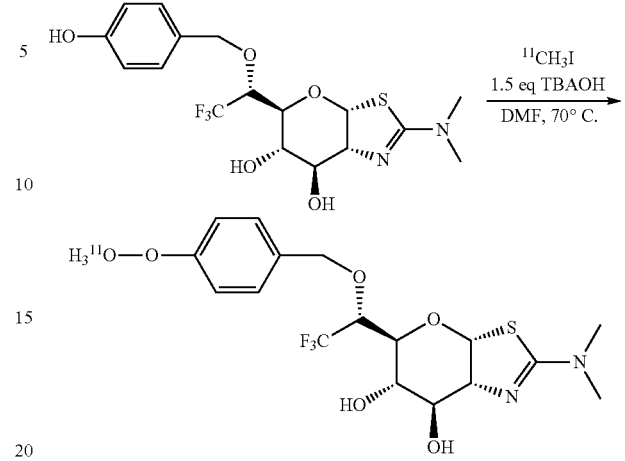

[¹¹C]MeI (494 mCi) (synthesized by the same procedure disclosed in Example 118) was trapped in a 0° C. mixture of (3aR,5S,6S,7R,7aR)-2-(dimethylamino)-5-((R)-2,2,2-trifluoro-1-(4-hydroxybenzyloxy)ethyl)-5,6,7,7a-tetrahydro-3aH-pyrano[3,2-d]thiazole-6,7-diol (Example 21) in DMF (0.42 mg, 0.25 mL) containing 1.5 µl of TBAOH (1 M in methanol). The reaction mixture was transferred to a 2 mL v-vial at 70° C., heated for 5 minutes, diluted with H$_2$O (0.8 mL) and injected onto the HPLC (XBridge C18, 10×150 mm, Waters). The mobile phase consisted of acetonitrile (CH$_3$CN) (A) and 0.1% ammonium hydroxide (pH 10) (B). The solvent system started with 35% A and 65% B for 0-8 min at 3 mL/min, and then a gradient method was followed. A linear gradient of 35% A to 60% A over 6 min, holding at 60% A for 10 min with a run time of 25 min at 3 mL/min was used. The preparative run was monitored at 254 nm with an Amersham Bioscience (Piscataway, N.J.) UV-M II detector and a Bioscan (Missisauga, Ontario, Canada) FlowCount radioactivity detector.

The desired peak (retention time 15.7 min) was collected in a heated round bottom flask on a rotary evaporator. The solution was concentrated and vacuum transferred to a septum capped 5 mL v-vial. The round bottom flask was rinsed with ethanol (0.1 mL) and saline (1-2 mL) and vacuum transferred to the same v-vial to give 31.9 mCi of (3aR,5S,6S,7R,7aR)-2-(dimethylamino)-5-((R)-2,2,2-trifluoro-1-[¹¹C](4-methoxybenzyloxy)ethyl)-5,6,7,7a-tetrahydro-3aH-pyrano[3,2-d]thiazole-6,7-diol.

Example 120

[¹¹C](3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol

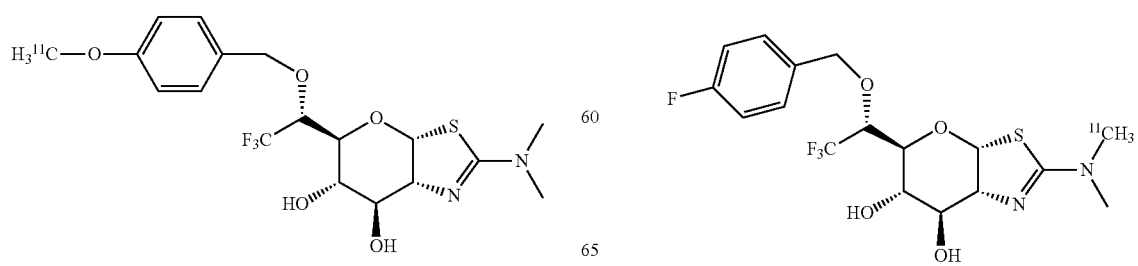

Scheme XVII

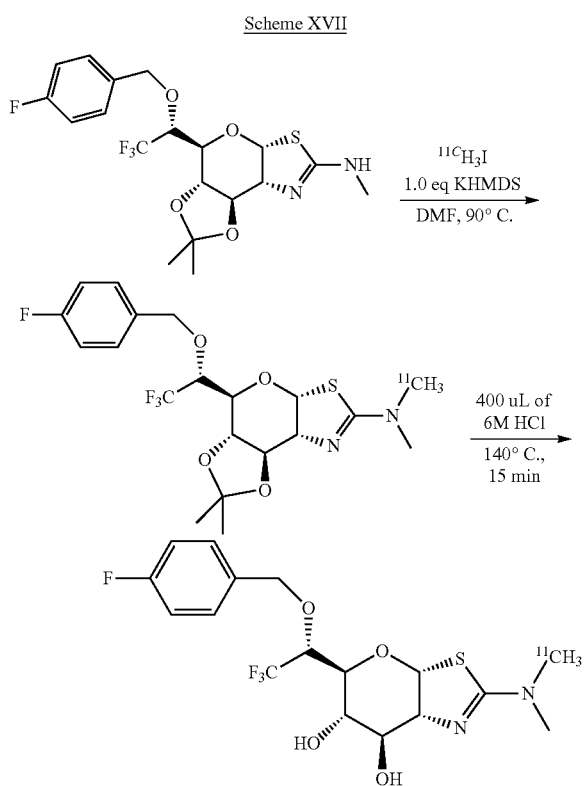

[$^{11}$C]MeI (235 mCi) (synthesized by the same procedure disclosed in Example 118) was trapped in a 0° C. mixture of (1R,2R,6R,8S,9S)—N,11,11-trimethyl-8-[(1S)-2,2,2-trifluoro-1-[(4-fluorophenyl)methoxy]ethyl]-7,10,12-trioxa-5-thia-3-azatricyclo[7.3.0.0[2,6]]dodec-3-en-4-amine in DMF (0.45 mg, 0.45 mL) containing 1 µl of KHMDS (1 M in THF). The reaction mixture was transferred to a 2 mL v-vial at 90° C., heated for 4 minutes. The reaction mixture was allowed to cool for 2 min. Hydrogen chloride (400 µL, 6M) was added to the crude reaction mixture. The mixture was heated at 140° C. for 15 min. After cooling for 5 min, the mixture was diluted with water (800 µL) and loaded onto an Xbridge C-18 semi-preparative HPLC column. The mobile phase consisted of acetonitrile ($CH_3CN$) (A) and 0.1% ammonium hydroxide (pH 10) (B). A linear gradient of 30% A 70% B to 90% A 10% B over 15 min at 3 mL/min was used. The peak corresponding to [$^{11}$C](3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol eluting at 10.6 min was collected, and most of the solvent was evaporated, and transferred into a sterile vial for animal studies.

Biological Activity

Assay for Determination of $K_I$ Values for Inhibition of O-GlcNAcase Activity Experimental Procedure for Kinetic Analyses Enzymatic reactions were carried out in a reaction containing 50 mM $NaH_2PO_4$, 100 mM NaCl and 0.1% BSA (pH 7.0) using 2 mM 4-Methylumbelliferyl N-acetyl-β-D-glucosaminide dihydrate (Sigma M2133) dissolved in dd$H_2O$, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data was determined.

Ki values were determined using the Cheng-Prusoff equation; the Km of O-GlcNAcase for substrate was 0.2 mM. Examples 1 to 120 were tested in the above described assay and exhibited $K_i$ values for inhibition of O-GlcNAcase in the range 0.1 nM-10 µM. Representative data from the assay described above are shown in Table 2 (Example 117 is a synthetic intermediate and does not possess inhibitory activity in the aforementioned range).

Assay for Determination of Cellular Activity for Compounds that Inhibit O-GlcNAcase Activity Inhibition of O-GlcNAcase, which removes O-GlcNAc from cellular proteins, results in an increase in the level of O-GlcNAcylated protein in cells. An increase in O-GlcNAcylated protein can be measured by an antibody, such as RL-2, that binds to O-GlcNAcylated protein. The amount of O-GlcNAcylated protein:RL2 antibody interaction can be measured by enzyme linked immunosorbant assay (ELISA) procedures.

A variety of tissue culture cell lines, expressing endogenous levels of O-GlcNAcase, can be utilized; examples include rat PC-12, and human U-87, or SK-N-SH cells. In this assay, rat PC-12 cells were plated in 96-well plates with approximately 10,000 cells/well. Compounds to be tested were dissolved in DMSO, either 2 or 10 mM stock solution, and then diluted with DMSO and water in a two-step process using a Tecan workstation. Cells were treated with diluted compounds for 24 hours (5.4 µL into 200 µL 1 well volume) to reach a final concentration of inhibitor desired to measure a compound concentration dependent response, typically, ten 3 fold dilution steps, starting at 10 µM are used to determine a concentration response curve. To prepare a cell lysate, the media from compound treated cells was removed, the cells were washed once with phosphate buffered saline (PBS) and then lysed for 5 minutes at room temperature in 50 µL of Phosphosafe reagent (Novagen Inc, Madison, Wis.) with protease inhibitors and PMSF. The cell lysate was collected and transferred to a new plate, which was then either coated to assay plates directly or frozen −80° C. until used in the ELISA procedure. If desired, the total protein concentration of samples is determined using 20 µL of the sample using the BCA method.

The ELISA portion of the assay was performed in a black Maxisorp 96-well plate that was coated overnight at 4° C. with 100 µL/well of the cell lysate (1:10 dilution of the lysate with PBS containing protease inhibitors, phosphatase inhibitors, and PMSF. The following day the wells were washed 3 times with 300 µL/well of Wash buffer (Tris-buffered saline with 0.1% Tween 20). The wells were blocked with 100 µL/well Blocking buffer (Tris buffered saline w/0.05% Tween 20 and 2.5% Bovine serum albumin). Each well was then washed two times with 300 µl/well of wash buffer. The anti O-GlcNAc antibody RL-2 (Abcam, Cambridge, Mass.), diluted 1:1000 in blocking buffer, was added at 100 µl/well. The plate was sealed and incubated at 37° C. for 2 hr with gentle shaking. The wells were then washed 3-times with 300 μl/well wash buffer. To detect the amount of RL-2 bound horse-radish peroxidase (HRP) conjugated goat anti-mouse secondary antibody (diluted 1:3000 in blocking buffer) was added at 100 μL/well. The plate was incubated for 60 min at 37° C. with gentle shaking. Each well was then washed 3-times with 300 μl/well wash buffer. The detection reagent was added, 100 μL/well of Amplex Ultra RED reagent (prepared by adding 30 μL of 10 mM Amplex Ultra Red stock solution to 10 ml PBS with 18 μL 3% hydrogen peroxide, $H_2O_2$). The detection reaction was incubated for 15 minutes at room temperature and then read with excitation at 530 nm and emission at 590 nm.

The amount of O-GlcNAcylated protein, as detected by the ELISA assay, was plotted for each concentration of test compound using standard curve fitting algorithms for sigmoidal dose response curves. The values for a four parameter logistic curve fit of the data were determined, with the inflection point of the curve being the potency value for the test compound.

Representative data from the cell-based assay described above are shown in Table 2.

TABLE 2

O-GlcNAcase Inhibitory Data and Cell Based Data for Selected Compounds

| Example | OGA KI (nM) | Cell based ELISA $EC_{50}$ (nM) |
|---|---|---|
| 1 | 10.8 | ND |
| 2 | 4.6 | 282.3 |
| 4 | 4.98 | 41.83 |
| 7 | 4.35 | 58.03 |
| 8 | 5.06 | 21.85 |
| 9 | 1.79 | 37.48 |
| 12 | 222 | ND |
| 13 | 100 | ND |
| 15 | 3.69 | 87.38 |
| 17 | 41.9 | ND |
| 20 | 0.82 | 8.987 |
| 21 | 3.31 | 8.993 |
| 25 | 4.50 | 23.27 |
| 27 | 4.14 | 42.06 |
| 28 | 8.83 | ND |
| 29 | 4.88 | 82.83 |
| 30 | 2.85 | 63.03 |
| 31 | 4.40 | 22.34 |
| 33 | 4.85 | 68.7 |
| 34 | 2.27 | 46.4 |
| 36 | 1.52 | 51.72 |
| 39 | 2.43 | 36.22 |
| 42 | 2.36 | 119.5 |
| 44 | 3.05 | ND |
| 45 | 1.97 | 127.6 |
| 46 | 1.44 | 94.83 |
| 47 | 20.4 | ND |
| 48 | 10.3 | 335.5 |
| 52 | 1.38 | 21.33 |
| 54 | 1.35 | 31.09 |
| 55 | 0.65 | 79.45 |
| 57 | 1.11 | 62.09 |
| 58 | 0.84 | 76.88 |
| 60 | 0.45 | 9.529 |
| 61 | 1.98 | 7.726 |
| 64 | 1.32 | 8.432 |
| 65 | 1.02 | 27.74 |
| 66 | 2.32 | 13.53 |
| 69 | 1.13 | 24.01 |
| 70 | 0.61 | 17.79 |
| 71 | 0.78 | 30.76 |
| 74 | 2250 | ND |
| 76 | 726 | ND |
| 79 | 3.77 | 172.9 |
| 80 | 1.49 | 78.52 |
| 85 | 3.11 | ND |
| 87 | 0.71 | 46.41 |
| 88 | 0.59 | 46.56 |
| 89 | 1.44 | 57.44 |
| 96 | 12.5 | ND |
| 102 | 1.06 | 40.11 |
| 104 | 4.29 | 62.36 |
| 105 | 43.6 | ND |
| 108 | 12.2 | 96.32 |
| 109 | 6.73 | 80.17 |
| 116 | 102 | ND |

Assay for Determination of Apparent Permeability ($P_{app}$)

Bi-directional transport was evaluated in LLC-PK1 cells in order to determine apparent permeability ($P_{app}$). LLC-PK1 cells can form a tight monolayer and therefore can be used to assess vectorial transport of compounds from basolateral to apical (B→A) and from apical to basolateral (A→B).

To determine $P_{app}$, LLC-PK1 cells were cultured in 96-well transwell culture plates (Millipore). Solutions containing the test compounds (1 μM) were prepared in Hank's Balanced Salt Solution with 10 mM HEPES. Substrate solution (150 μL) was added to either the apical (A) or the basolateral (B) compartment of the culture plate, and buffer (150 μL) was added to the compartment opposite to that containing the compound. At t=3 h, 50 μL samples were removed from both sides of monolayers dosed with test compound and placed in 96 well plates, scintillant (200 μL) or internal standard (100 μL labetolol 1 μM) was added to the samples and concentration was determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 μM) was used as the positive control. The experiment was performed in triplicate.

The apparent permeability, $P_{app}$, was calculated by the following formula for samples taken at t=3 h:

$$P_{app} = \frac{\text{Volume of Receptor Chamber (mL)}}{[\text{Area of membrane (cm}^2)][\text{Initial Concentration }(\mu M)]} \times \frac{\Delta \text{ in Concentration }(\mu M)}{\Delta \text{ in Time }(s)}$$

Where: Volume of Receptor Chamber was 0.15 mL; Area of membrane was 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). $P_{app}$ was expressed as $10^{-6}$ cm/s. The $P_{app}$ (LLC-PK1 cells) are the average of the $P_{app}$ for transport from A to B and $P_{app}$ for transport from B to A at t=3 h:

$$P_{app}(LLC-PK1 \text{ Cells}) = \frac{P_{app}(A \to B) + P_{app}(B \to A)}{2}$$

Representative data from the permeability assays described above are shown in Table 3.

TABLE 3

Permeability Data for Selected Compounds

| Example | Papp (×10−6 cm/sec) |
|---|---|
| 2 | 20.8 |
| 3 | 28.3 |
| 4 | 27.3 |
| 9 | 31.5 |
| 16 | 15.5 |
| 17 | 31.2 |
| 20 | 29.8 |
| 22 | 27.2 |
| 23 | 23.6 |
| 25 | 29.5 |
| 26 | 30.8 |
| 27 | 32 |
| 29 | 20.9 |
| 30 | 30.8 |
| 31 | 31.3 |
| 34 | 33.3 |
| 35 | 33.6 |
| 36 | 28.1 |
| 40 | 31.2 |
| 41 | 30.7 |
| 42 | 15.2 |
| 46 | 34.5 |
| 47 | 34 |
| 49 | 29.8 |
| 50 | 31.5 |
| 51 | 30.9 |
| 52 | 30.5 |
| 53 | 33.0 |
| 54 | 31.3 |
| 55 | 27.1 |
| 57 | 16.37 |
| 58 | 26.2 |
| 59 | 29.6 |
| 60 | 29.0 |
| 61 | 29.0 |
| 62 | 31.1 |
| 63 | 31.2 |
| 64 | 29.9 |
| 65 | 28.8 |
| 66 | 28.2 |
| 67 | 29.5 |
| 68 | 34.1 |
| 69 | 31.1 |
| 70 | 29.5 |
| 71 | 34.6 |
| 72 | 25.4 |
| 73 | 19.9 |
| 74 | 24.5 |
| 79 | 20.4 |
| 80 | 28.5 |
| 83 | 29.7 |
| 84 | 27.0 |
| 85 | 26.3 |
| 86 | 29.9 |
| 89 | 25.4 |
| 93 | 29.2 |
| 94 | 24.6 |
| 96 | 30.1 |
| 97 | 24.7 |
| 98 | 29.1 |
| 99 | 21.7 |
| 100 | 28.1 |
| 101 | 28.9 |
| 107 | 31.3 |
| 109 | 26.3 |

Table 4 shows O-GlcNAcase inhibitory activity and permeability for structurally similar compounds described in PCT/US11/059668 In comparing the data obtained for the compounds of the invention set forth in Tables 2 and 3 to data obtained for the compounds set forth in Table 4, it can be seen that the compounds of the invention retain high potency yet also exhibit enhanced permeability over the compounds set forth in Table 4.

TABLE 4

Comparative O-GlcNAcase Inhibitory and Permeability Data for Compounds Described in PCT/US11/059668

| Example | Name | Structure | OGA KI (nM) | Papp (X10−6 cm/sec) |
|---|---|---|---|---|
| 11 | (3aR,5S,6S,7R,7aR)-2-(dimethylamino)-5-((R)-2,2,2-trifluoro-1-hydroxyethyl)-5,6,7,7a-tetrahydro-3aH-pyrano[3,2-d]thiazole-6,7-diol | 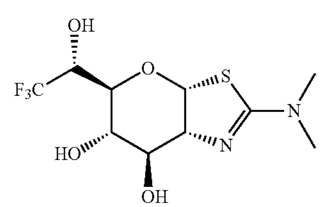 [SMILES: CN(C)C1=N[C@@H]2[C@@H](O)[C@H](O)[C@@H]([C@@H](O)C(F)(F)F)O[C@@H]2S1] | 0.19 | 1.6 |
| 62 | 3aR,5R,6S,7R,7aR)-2-(dimethylamino)-5-((S)-1-hydroxypropyl)-5,6,7,7a-tetrahydro-3aH-pyrano[3,2-d]thiazole-6,7-diol (Slower eluting isomer) | 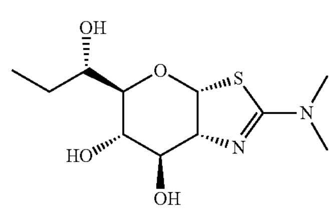 [SMILES: CC[C@H](O)[C@H]1O[C@@H]2SC(N(C)C)=N[C@@H]2[C@@H](O)[C@@H]1O] | 0.96 | 1.7 |

TABLE 4-continued

Comparative O-GlcNAcase Inhibitory and Permeability Data for Compounds Described in PCT/US11/059668

| Example | Name | Structure | OGA KI (nM) | Papp (X10-6 cm/sec) |
|---|---|---|---|---|
| 95 | (3aR,5S,6S,7R,7aR)-2-(methylamino)-5-((R)-2,2,2-trifluoro-1-hydroxyethyl)-5,6,7,7a-tetrahydro-3aH-pyrano[3,2-d]thiazole-6,7-diol | 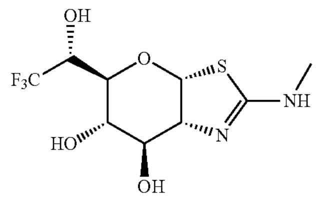 [SMILES: CNC1=N[C@@H]2[C@@H](O)[C@H](O)[C@@H]([C@@H](O)C(F)(F)F)O[C@@H]2S1] | 0.16 | <1.0 |
| 111 | (3aR,5R,6S,7R,7aR)-5-((S)-1-hydroxypentyl)-2-(methylamino)-5,6,7,7a-tetrahydro-3aH-pyrano[3,2-d]thiazole-6,7-diol(Slower eluting isomer) | 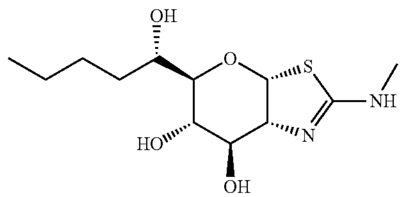 [SMILES: CCCC[C@H](O)[C@H]1O[C@@H]2SC(NC)=N[C@@H]2[C@@H](O)[C@@H]1O] | 4.26 | 2.7 |
| 158 | (3aR,5S,6S,7R,7aR)-2-(methylamino)-5-((S)-1,1,1-trifluoro-2-hydroxypropan-2-yl)-5,6,7,7a-tetrahydro-3aH-pyrano[3,2-d]thiazole-6,7-diol | 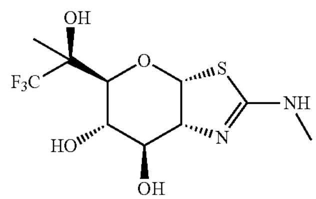 [SMILES: CNC1=N[C@@H]2[C@@H](O)[C@H](O)[C@@H]([C@](C)(O)C(F)(F)F)O[C@@H]2S1] | 1.29 | 2.9 |

What is claimed is:

1. A compound of Formula (I)

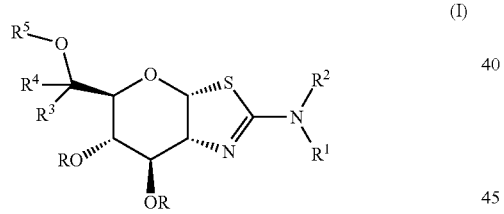

(I)

or a pharmaceutically acceptable salt thereof,
wherein:
each R is independently H or C(O)CH$_3$;
R$^1$ and R$^2$ are independently (a) hydrogen, (b) C1-6alkyl optionally substituted with 1 to 3 substituents selected from F, —OH, —OCH$_3$ and —CH$_3$ or (c)C1-6alkoxy optionally substituted with 1 to 3 substituents selected from F, —OH, —OCH$_3$ and —CH$_3$;
or R$^1$ and R$^2$ may be joined together with the nitrogen atom to which they are attached to form azetidine, pyrrolidine, piperidine or isoxazolidine;
R$^3$ is C1-10alkyl optionally substituted with 1 to 3 fluoro;
R$^4$ is hydrogen or C1-10alkyl optionally substituted with phenyl;
R$^5$ is
(A) C1-8alkyl optionally substituted with one substituent selected from the group consisting of:
(1) fluoro,
(2) morpholino,
(3) C3-6cycloalkyl,
(4) pyridinyl optionally substituted with C1-6alkyl,
(5) phenyl optionally substituted with 1 to 4 substituents selected from the group consisting of:
(a) fluoro, (b) hydroxy, (c) C1-6alkyl optionally substituted with 1 to 3 fluoro, (d) C1-6alkenyl, (e) C1-5alkoxy optionally substituted with fluoro, (f) phenyl, (g) phenyloxy, (h) benzyloxy and (i) C1-10alkylphenyl;
(B) phenyl optionally substituted with one substituent selected from the group consisting of:
(1) —NO$_2$, (2) —NH$_2$, (3) fluoro, (4) C1-6alkyl optionally substituted with fluoro, and (5) C1-6alkoxy optionally substituted with fluoro; and
(C) pyridinyl optionally substituted with a substituent selected from the group consisting of:
(1) fluoro, (2) C1-6alkyl optionally substituted with fluoro and (3) C1-6alkoxy optionally substituted with fluoro.

2. The compound of claim 1 or a pharmaceutically acceptable salt thereof, wherein R$^3$ is methyl or trifluoromethyl.

3. The compound of claim 1 of Formula (Ia):

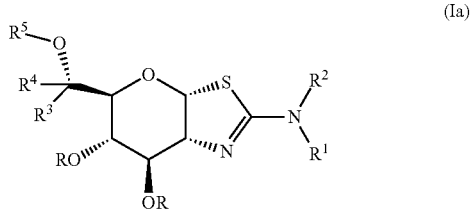

(Ia)

or a pharmaceutically acceptable salt thereof.

4. The compound of claim 1 of Formula (Ib):

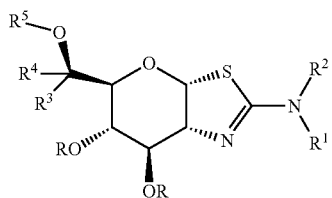

(Ib)

or a pharmaceutically acceptable salt thereof.

5. The compound of claim 1 or a pharmaceutically acceptable salt thereof, wherein:
$R^3$ is methyl or trifluoromethyl;
$R^4$ is hydrogen; and
$R^5$ is C1-6alkyl optionally substituted with one substituent selected from the group consisting of:
(1) fluoro,
(2) morpholino,
(3) C3-6cycloalkyl,
(4) pyridinyl optionally substituted with C1-6alkyl,
(5) phenyl optionally substituted with 1 to 4 substituents selected from the group consisting of:
(a) fluoro, (b) hydroxy, (c) C1-6alkyl optionally substituted with fluoro, (d) C1-6alkenyl, (e) C1-5alkoxy optionally substituted with fluoro, (f) phenyl, (g) phenyloxy, (h) benzyloxy and (i) C11-6alkylphenyl.

6. The compound according to claim 1 or a pharmaceutically acceptable salt thereof, wherein:
$R^3$ is methyl or trifluoromethyl;
$R^4$ is hydrogen; and
$R^5$ is phenyl optionally substituted with one substituent selected from the group consisting of: (1) —$NO_2$, (2) —$NH_2$, (3) fluoro, (4) C1-6alkyl optionally substituted with fluoro, and (5) C1-6alkoxy optionally substituted with fluoro.

7. The compound of claim 1 or a pharmaceutically acceptable salt thereof, wherein:
$R^3$ is methyl or trifluoromethyl;
$R^4$ is hydrogen; and
$R^5$ is pyridinyl optionally substituted with a substituent from the group consisting of: (1) fluoro, (2) C1-6alkyl optionally substituted with fluoro, and (3) C1-6alkoxy optionally substituted with fluoro.

8. The compound of claim 1, wherein the compound is selected from the group consisting of:
(3aR,5S,6S,7R,7aR)-2-(dimethylamino)-5-((S)-2,2,2-trifluoro-1-methoxyethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-methoxyethyl)-5,6,7,7a-tetrahydro-3aH-pyrano[3,2-d]thiazole-6,7-diol;
(3aR,5S,6S,7R,7aR)-2-(methylamino)-5-((S)-2,2,2-trifluoro-1-phenoxyethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-phenoxyethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-methoxyethyl)-5,6,7,7a-tetrahydro-3aH-pyrano[3,2-d]thiazole-6,7-diol;
(3aR,5S,6S,7R,7aR)-2-(ethylamino)-5-((R)-2,2,2-trifluoro-1-methoxyethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-nitrophenoxy)ethyl)-5,6,7,7a-tetrahydro-3aH-pyrano[3,2-d]thiazole-6,7-diol;
(3aR,5S,6S,7R,7aR)-5-((R)-1-(4-aminophenoxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(4-nitrophenoxy)ethyl)-5,6,7,7a-tetrahydro-3aH-pyrano[3,2-d]thiazole-6,7-diol;
(3aR,5S,6S,7R,7aR)-2-(dimethylamino)-5-((R)-1-methoxyethyl)-5,6,7,7a-tetrahydro-3aH-pyrano[3,2-d]thiazole-6,7-diol;
(3aR,5S,6S,7R,7aR)-2-(dimethylamino)-5-((S)-1-methoxyethyl)-5,6,7,7a-tetrahydro-3aH-pyrano[3,2-d]thiazole-6,7-diol;
(3aR,5S,6S,7R,7aR)-5-((R)-1-(4-(allyloxy)benzyloxy)-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-5-((R)-1-(4-hydroxybenzyloxy)-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol;
(3aR,5S,6S,7R,7aR)-2-(dimethylamino)-5-((R)-1-ethoxy-2,2,2-trifluoroethyl)-5,6,7,7a-tetrahydro-3aH-pyrano[3,2-d]thiazole-6,7-diol;
(3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-propoxyethyl)-5,6,7,7a-tetrahydro-3aH-pyrano[3,2-d]thiazole-6,7-diol;
(3aR,5S,6S,7R,7aR)-5-((R)-1-butoxy-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(pentyloxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(2-fluoroethoxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(3-fluoropropoxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(4-fluorobutoxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(5-fluoropentyloxy)ethyl)-5,6,7,7a-tetrahydro-3aH-pyrano[3,2-d]thiazole-6,7-diol;
(3aR,5S,6S,7R,7aR)-2-(dimethylamino)-5-((S)-2,2,2-trifluoro-1-(5-fluoropentyloxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(2-morpholinoethoxy)ethyl)-5,6,7,7a-tetrahydro-3aH-pyrano[3,2-d]thiazole-6,7-diol;
(3aR,5S,6S,7R,7aR)-5-((R)-1-(2-cyclohexylethoxy)-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-5-((R)-1-(cyclohexylmethoxy)-2,2,2-trifluoroethyl)-2-(dimethylamino)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(3-(4-fluorophenyl)propoxy)ethyl)-5,6,7,7a-tetrahydro-3aH-pyrano[3,2-d]thiazole-6,7-diol;

(3aR,5S,6S,7R,7aR)-2-(dimethylamino)-5-((S)-2,2,2-trif-luoro-1-(3-(4-fluorophenyl)propoxy)ethyl)-5,6,7,7a-tetrahydro-3aH-pyrano[3,2-d]thiazole-6,7-diol;

(3aR,5S,6S,7R,7aR)-5-((S)-1-(benzyloxy)-2,2,2-trifluo-roethyl)-2-(dimethylamino)-5,6,7,7a-tetrahydro-3aH-pyrano[3,2-d]thiazole-6,7-diol;

(3aR,5S,6S,7R,7aR)-5-((R)-1-(benzyloxy)-2,2,2-trifluo-roethyl)-2-(dimethylamino)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-methylbenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-1-(4-eth-ylbenzyloxy)-2,2,2-trifluoroethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(pyridin-3-ylmethoxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-vinylbenzyloxy)ethyl)-5,6,7,7a-tetrahydro-3aH-pyrano[3,2-d]thiazole-6,7-diol;

(3aR,5S,6S,7R,7aR)-5-((R)-1-(biphenyl-4-ylmethoxy)-2,2,2-trifluoroethyl)-2-(dimethylamino)-5,6,7,7a-tetra-hydro-3aH-pyrano[3,2-d]thiazole-6,7-diol;

(3aR,5S,6S,7R,7aR)-5-((R)-1-(4-benzylbenzyloxy)-2,2,2-trifluoroethyl)-2-(dimethylamino)-5,6,7,7a-tetra-hydro-3aH-pyrano[3,2-d]thiazole-6,7-diol;

(3aR,5S,6S,7R,7aR)-5-((R)-1-(2,3-difluorobenzyloxy)-2,2,2-trifluoroethyl)-2-(dimethylamino)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-((S)-1-phenylethoxy)ethyl)-5,6,7,7a-tetra-hydro-3aH-pyrano[3,2-d]thiazole-6,7-diol; (Less-polar epimer on TLC)

(3aR,5S,6S,7R,7aR)-2-(dimethylamino)-5-((R)-2,2,2-tri-fluoro-1-((R)-1-phenylethoxy)ethyl)-5,6,7,7a-tetra-hydro-3aH-pyrano[3,2-d]thiazole-6,7-diol;

(3aR,5S,6S,7R,7aR)-2-(dimethylamino)-5-((S)-2,2,2-trif-luoro-1-(2-methoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(2-methoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(3-methoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-methoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-methoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-methoxy-3-methylbenzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-(2-fluoroethoxy)benzyloxy)ethyl)-5,6,7,7a-tetrahydro-3aH-pyrano[3,2-d]thiazole-6,7-diol;

(3aR,5S,6S,7R,7aR)-5-((R)-1-(4-(benzyloxy)benzyloxy)-2,2,2-trifluoroethyl)-2-(dimethylamino)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-phenoxybenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((R)-2,2,2-tri-fluoro-1-(4-methoxy-3-(trifluoromethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-1-(3-ethyl-4-methoxybenzyloxy)-2,2,2-trifluoroethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-methoxy-3,5-dimethylbenzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(2-fluorobenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((S)-2,2,2-trif-luoro-1-(2-fluorobenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((S)-2,2,2-trif-luoro-1-(3-fluorobenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((S)-2,2,2-trif-luoro-1-(3-fluorobenzyloxy)ethyl)-5,6,7,7a-tetra-hydro-3aH-pyrano[3,2-d]thiazole-6,7-diol;

(3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-(trifluoromethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(3-(trifluoromethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(2-(trifluoromethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-(fluoromethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-(2-fluoroethyl)benzyloxy)ethyl)-5,6,7,7a-tetrahydro-3aH-pyrano[3,2-d]thiazole-6,7-diol;

(3aR,5S,6S,7R,7aR)-2-(dimethylamino)-5-((R)-2,2,2-tri-fluoro-1-(4-(3-fluoropropyl)benzyloxy)ethyl)-5,6,7,7a-tetrahydro-3aH-pyrano[3,2-d]thiazole-6,7-diol;

(3aR,5S,6S,7R,7aR)-2-(ethyl(methyl)amino)-5-((S)-2,2,2-trifluoro-1-methoxyethyl)-5,6,7,7a-tetrahydro-3aH-pyrano[3,2-d]thiazole-6,7-diol;

(3aR,5S,6S,7R,7aR)-2-(ethyl(methyl)amino)-5-((R)-2,2,2-trifluoro-1-methoxyethyl)-5,6,7,7a-tetrahydro-3aH-pyrano[3,2-d]thiazole-6,7-diol;

(3aR,5S,6S,7R,7aR)-2-(dimethylamino)-5-((S)-1,1,1-trif-luoro-2-methoxypropan-2-yl)-5,6,7,7a-tetrahydro-3aH-pyrano[3,2-d]thiazole-6,7-diol;

(3aR,5S,6S,7R,7aR)-2-(dimethylamino)-5-(1,1,1-trif-luoro-2-methoxypropan-2-yl)-5,6,7,7a-tetrahydro-3aH-pyrano[3,2-d]thiazole-6,7-diol;

(3aR,5S,6S,7R,7aR)-5-((R)-2-(benzyloxy)-1,1,1-trif-luoro-4-phenylbutan-2-yl)-2-(dimethylamino)-5,6,7,7a-tetrahydro-3aH-pyrano[3,2-d]thiazole-6,7-diol;

(3aR,5S,6S,7R,7aR)-2-(methylamino)-5-((S)-2,2,2-trif-luoro-1-methoxyethyl)-5,6,7,7a-tetrahydro-3aH-pyrano[3,2-d]thiazole-6,7-diol;

(3aR,5S,6S,7R,7aR)-5-((R)-1-ethoxy-2,2,2-trifluoro-ethyl)-2-(methylamino)-5,6,7,7a-tetrahydro-3aH-pyrano[3,2-d]thiazole-6,7-diol;

(3aR,5S,6S,7R,7aR)-2-(methylamino)-5-((R)-2,2,2-trif-luoro-1-propoxyethyl)-5,6,7,7a-tetrahydro-3aH-pyrano[3,2-d]thiazole-6,7-diol;

(3aR,5S,6S,7R,7aR)-5-((R)-1-(2-cyclohexylethoxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(2-fluoroethoxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(3-fluoropropoxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(3-(4-fluorophenyl)propoxy)ethyl)-5,6,7,7a-tetrahydro-3aH-pyrano[3,2-d]thiazole-6,7-diol;
(3aR,5S,6S,7R,7aR)-5-((R)-1-(benzyloxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-methylbenzyloxy)ethyl)-5,6,7,7a-tetrahydro-3aH-pyrano[3,2-d]thiazole-6,7-diol;
(3aR,5S,6S,7R,7aR)-5-((R)-1-(4-ethylbenzyloxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-(2-fluoroethyl)benzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-(3-fluoropropyl)benzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-fluorobenzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(2-fluorobenzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(3-fluorobenzyloxy)ethyl)-5,6,7,7a-tetrahydro-3aH-pyrano[3,2-d]thiazole-6,7-diol;
(3aR,5S,6S,7R,7aR)-5-((R)-1-(2,3-difluorobenzyloxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(2-(trifluoromethyl)benzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-(trifluoromethyl)benzyloxy)ethyl)-5,6,7,7a-tetrahydro-3aH-pyrano[3,2-d]thiazole-6,7-diol;
(3aR,5S,6S,7R,7aR)-5-((R)-1-(4-benzylbenzyloxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(ethylamino)-5-((R)-2,2,2-trifluoro-1-(4-methoxybenzyloxy)ethyl)-5,6,7,7a-tetrahydro-3aH-pyrano[3,2-d]thiazole-6,7-diol;
2-(methylamino)-5-(2,2,2-trifluoro-1-(4-methoxybenzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-methoxy-3-(trifluoromethyl)benzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-phenoxybenzyloxy)ethyl)-5,6,7,7a-tetrahydro-3aH-pyrano[3,2-d]thiazole-6,7-diol;
(3aR,5S,6S,7R,7aR)-5-((R)-1-(3-ethyl-4-methoxybenzyloxy)-2,2,2-trifluoroethyl)-2-(methylamino)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(4-methoxy-3,5-dimethylbenzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-((6-methylpyridin-3-yl)methoxy)ethyl)-5,6,7,7a-tetrahydro-3aH-pyrano[3,2-d]thiazole-6,7-diol;
(3aR,5S,6S,7R,7aR)-2-(dimethylamino)-5-((S)-2,2,2-trifluoro-1-(4-nitrophenoxy)ethyl)-5,6,7,7a-tetrahydro-3aH-pyrano[3,2-d]thiazole-6,7-diol;
(3aR,5S,6S,7R,7aR)-5-((R)-1-(4-aminophenoxy)-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(pyridin-2-yloxy)ethyl)-5,6,7,7a-tetrahydro-3aH-pyrano[3,2-d]thiazole-6,7-diol;
(3aR,5S,6S,7R,7aR)-2-(dimethylamino)-5-((S)-2,2,2-trifluoro-1-phenoxyethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-phenoxyethyl)-5,6,7,7a-tetrahydro-3aH-pyrano[3,2-d]thiazole-6,7-diol;
(3aR,5S,6S,7R,7aR)-5-((S)-1-(benzyloxy)ethyl)-2-(dimethylamino)-5,6,7,7a-tetrahydro-3aH-pyrano[3,2-d]thiazole-6,7-diol;
(3aR,5S,6S,7R,7aR)-2-(dimethylamino)-5-((S)-1-(4-methoxybenzyloxy)ethyl)-5,6,7,7a-tetrahydro-3aH-pyrano[3,2-d]thiazole-6,7-diol;
(3aR,5S,6S,7R,7aR)-5-((R)-1-methoxyethyl)-2-(methylamino)-5,6,7,7a-tetrahydro-3aH-pyrano[3,2-d]thiazole-6,7-diol; and
(3aR,5S,6S,7R,7aR)-5-((S)-1-methoxyethyl)-2-(methylamino)-5,6,7,7a-tetrahydro-3aH-pyrano[3,2-d]thiazole-6,7-diol;

or a pharmaceutically acceptable salt thereof.

9. A compound of the Formula (II):

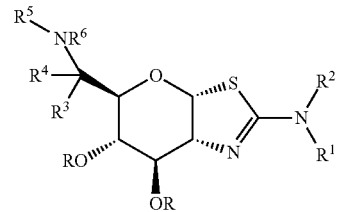

(II)

or a pharmaceutically acceptable salt thereof, wherein:

each R is independently H or C(O)CH$_3$;

R$^1$ and R$^2$ are independently (a) hydrogen, (b) C1-6alkyl optionally substituted with 1 to 3 substituents selected from F, —OH, —OCH$_3$ and —CH$_3$, or (c) C1-6alkoxy optionally substituted with F, —OH, —OCH$_3$ and —CH$_3$; or R$^1$ and R$^2$ may be joined together with the nitrogen atom to which they are attached to form azetidine, pyrrolidine, piperidine or isoxazolidine;

R$^3$ is C1-10alkyl optionally substituted from 1 to 3 fluoro;

R$^4$ and R$^5$ are independently hydrogen or C1-6 alkyl; and

R$^6$ is hydrogen, C1-6alkyl or C3-6cycloalkyl.

10. The compound of claim 9 of the Formula (IIa):

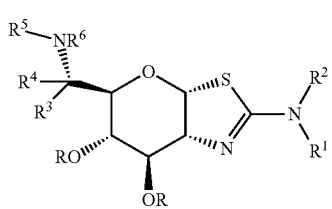

Formula (IIa)

or a pharmaceutically acceptable salt thereof.

11. The compound of claim 9 of the Formula (IIb):

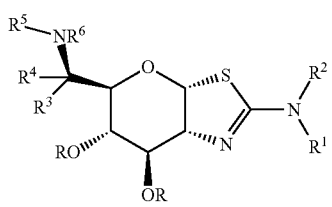

Formula (IIb)

or a pharmaceutically acceptable salt thereof.

12. The compound of claim 9, wherein the compound is selected from the group consisting of:
(3aR,5R,6S,7R,7aR)-5-((R)-1-(cyclopentylamino)ethyl)-2-(methylamino)-5,6,7,7a-tetrahydro-3aH-pyrano[3,2-d]thiazole-6,7-diol;
(3aR,5R,6S,7R,7aR)-5-((S)-1-(cyclopentylamino)ethyl)-2-(methylamino)-5,6,7,7a-tetrahydro-3aH-pyrano[3,2-d]thiazole-6,7-diol;
(3aR,5R,6S,7R,7aR)-5-((S)-1-amino-2,2,2-trifluoroethyl)-2-(dimethylamino)-5,6,7,7a-tetrahydro-3aH-pyrano[3,2-d]thiazole-6,7-diol;
(3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol;
(3aR,5R,6S,7R,7aR)-2-(dimethylamino)-5-((R)-2,2,2-trifluoro-1-(methylamino)ethyl)-5,6,7,7a-tetrahydro-3aH-pyrano[3,2-d]thiazole-6,7-diol;
(3aR,5R,6S,7R,7aR)-2-(dimethylamino)-5-((R)-1-(dimethylamino)-2,2,2-trifluoroethyl)-5,6,7,7a-tetrahydro-3aH-pyrano[3,2-d]thiazole-6,7-diol;
(3aR,5R,6S,7R,7aR)-5-((R)-1-aminoethyl)-2-(dimethylamino)-5,6,7,7a-tetrahydro-3aH-pyrano[3,2-d]thiazole-6,7-diol;
(3aR,5R,6S,7R,7aR)-5-((S)-1-aminoethyl)-2-(dimethylamino)-5,6,7,7a-tetrahydro-3aH-pyrano[3,2-d]thiazole-6,7-diol;
(3aR,5R,6S,7R,7aR)-2-(methylamino)-5-((S)-1-(methylamino)ethyl)-5,6,7,7a-tetrahydro-3aH-pyrano[3,2-d]thiazole-6,7-diol;
(3aR,5R,6S,7R,7aR)-2-(methylamino)-5-((R)-1-(methylamino)ethyl)-5,6,7,7a-tetrahydro-3aH-pyrano[3,2-d]thiazole-6,7-diol;
(3aR,5R,6S,7R,7aR)-5-((R)-1-(ethylamino)ethyl)-2-(methylamino)-5,6,7,7a-tetrahydro-3aH-pyrano[3,2-d]thiazole-6,7-diol;
(3aR,5R,6S,7R,7aR)-5-((S)-1-(ethylamino)ethyl)-2-(methylamino)-5,6,7,7a-tetrahydro-3aH-pyrano[3,2-d]thiazole-6,7-diol; and
(3aR,5R,6S,7R,7aR)-5-(1-(cyclopropylamino)ethyl)-2-(methylamino)-5,6,7,7a-tetrahydro-3aH-pyrano[3,2-d]thiazole-6,7-diol;
or a pharmaceutically acceptable salt thereof.

13. The compound of claim 1 or a pharmaceutically acceptable salt thereof, wherein the compound is isotopically labeled as $^{11}C$, $^{13}C$, $^{14}C$, $^{18}F$, $^{2}H$ or $^{3}H$.

14. The compound of claim 13 or a pharmaceutically acceptable salt thereof, wherein the compound is isotopically labeled with $^{11}C$.

15. A compound which is selected from the group consisting of:
(3aR,5S,6S,7R,7aR)-2-(dimethylamino)-5-((S)-1-methoxyethyl)-5,6,7,7a-tetrahydro-3aH-pyrano[3,2-d]thiazole-6,7-diol;
(3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-propoxyethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-(4-(trifluoromethyl)-benzyloxy)ethyl)-5,6,7,7a-tetrahydro-3aH-pyrano[3,2-d]thiazole-6,7-diol;
(3aR,5S,6S,7R,7aR)-2-(methylamino)-5-((R)-2,2,2-trifluoro-1-(3-fluoropropoxy)ethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-[$^{11}C$]methoxyethyl)-5,6,7,7a-tetrahydro-3aH-pyrano[3,2-d]thiazole-6,7-diol;
(3aR,5S,6S,7R,7aR)-2-(dimethylamino)-5-((R)-2,2,2-trifluoro-1-[$^{11}C$](4-methoxybenzyloxy)ethyl)-5,6,7,7a-tetrahydro-3aH-pyrano[3,2-d]thiazole-6,7-diol; and
[$^{11}C$](3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol;
or a pharmaceutically acceptable salt thereof.

16. The compound of claim 15 which is:
(3aR,5S,6S,7R,7aR)-2-(dimethylamino)-5-((S)-1-methoxyethyl)-5,6,7,7a-tetrahydro-3aH-pyrano[3,2-d]thiazole-6,7-diol;
or a pharmaceutically acceptable salt thereof.

17. The compound of claim 15 which is:
(3aR,5R,6S,7R,7aR)-5-((R)-1-amino-2,2,2-trifluoroethyl)-2-(dimethylamino)-5,6,7,7a-tetrahydro-3aH-pyrano[3,2-d]thiazole-6,7-diol;
or a pharmaceutically acceptable salt thereof.

18. The compound of claim 15 which is:
(3aR,5S,6S,7R,7aR)-2-(dimethylamino)-5-((R)-2,2,2-trifluoro-1-propoxyethyl)-5,6,7,7a-tetrahydro-3aH-pyrano[3,2-d]thiazole-6,7-diol;
or a pharmaceutically acceptable salt thereof.

19. The compound of claim 15 which is:
(3aR,5S,6S,7R,7aR)-2-(dimethylamino)-5-((R)-2,2,2-trifluoro-1-(4-(trifluoromethyl)benzyloxy)ethyl)-5,6,7,7a-tetrahydro-3aH-pyrano[3,2-d]thiazole-6,7-diol;
or a pharmaceutically acceptable salt thereof.

20. The compound of claim 15 which is:
(3aR,5S,6S,7R,7aR)-2-(methylamino)-5-((R)-2,2,2-trifluoro-1-(3-fluoropropoxy)ethyl)-5,6,7,7a-tetrahydro-3aH-pyrano[3,2-d]thiazole-6,7-diol;
or a pharmaceutically acceptable salt thereof.

21. The compound of claim 15 which is:
(3aR,5S,6S,7R,7aR)-2-(dimethylamino)-5-((R)-2,2,2-trifluoro-1-[$^{11}C$]methoxyethyl)-5,6,7,7a-tetrahydro-3aH-pyrano[3,2-d]thiazole-6,7-diol;
or a pharmaceutically acceptable salt thereof.

22. The compound of claim 15 which is:
(3aR,5S,6S,7R,7aR)-2-(dimethylamino)-5-((R)-2,2,2-trifluoro-1-[$^{11}$C](4-methoxybenzyloxy)ethyl)-5,6,7,7a-tetrahydro-3aH-pyrano[3,2-d]thiazole-6,7-diol;
or a pharmaceutically acceptable salt thereof.

23. The compound of claim 15 which is:
[$^{11}$C](3aR,5S,6S,7R,7aR)-2-(dimethylamino)-5-((S)-1-ethoxy-2,2,2-trifluoroethyl)-5,6,7,7a-tetrahydro-3aH-pyrano[3,2-d]thiazole-6,7-diol;
or a pharmaceutically acceptable salt thereof.

24. A pharmaceutical composition comprising a compound of claim 1 or a pharmaceutically acceptable salt thereof and a pharmaceutically acceptable carrier.

25. A pharmaceutical composition comprising a compound of claim 15 or a pharmaceutically acceptable salt thereof and a pharmaceutically acceptable carrier.

26. A method for treating a disease or disorder selected from the group consisting of consisting of Alzheimer's disease and related tauopathies, Amyotrophic lateral sclerosis, glaucoma, schizophrenia, Huntington's disease, Parkinson's disease, Progressive supranuclear palsy, Schizophrenia, Mild Cognitive Impairment (MCI), Neuropathy and cancer, in a human patient in need thereof which comprises administering to the patient a therapeutically effective amount of the compound of claim 1, or a pharmaceutically acceptable salt thereof.

27. The method of claim 26, wherein the patient has been diagnosed with a need for treatment of the disease or disorder prior to the step of administering the compound, or a pharmaceutically acceptable salt thereof.

28. A method of treating Alzheimer's disease in a human patient in need thereof which comprises administering to the patient a therapeutically effective amount of the compound of claim 1 or a pharmaceutically acceptable salt thereof.

29. A method of treating Parkinson's disease in a human patient in need thereof which comprises administering to the patient a therapeutically effective amount of the compound of claim 1 or a pharmaceutically acceptable salt thereof.

30. A method of treating Progressive supranuclear palsy in a human patient in need thereof which comprises administering to the patient a therapeutically effective amount of the compound of claim 1 or a pharmaceutically acceptable salt thereof.

* * * * *